(12) United States Patent
Hummer et al.

(10) Patent No.: US 11,721,192 B2
(45) Date of Patent: Aug. 8, 2023

(54) SYSTEM AND METHOD OF DETECTING CHEMICALS IN PRODUCTS OR THE ENVIRONMENT OF PRODUCTS USING SENSORS

(71) Applicants: Matthew Hummer, Atlantic Beach, FL (US); Gregory J. Hummer, Shaker Heights, OH (US)

(72) Inventors: Matthew Hummer, Atlantic Beach, FL (US); Gregory J. Hummer, Shaker Heights, OH (US)

(*) Notice: Subject to any disclaimer, the term of this patent is extended or adjusted under 35 U.S.C. 154(b) by 0 days.

(21) Appl. No.: 16/702,822

(22) Filed: Dec. 4, 2019

(65) Prior Publication Data
US 2020/0111342 A1  Apr. 9, 2020

Related U.S. Application Data

(63) Continuation-in-part of application No. 16/549,158, filed on Aug. 23, 2019, now abandoned, which is a continuation-in-part of application No. 15/951,500, filed on Apr. 12, 2018, now Pat. No. 10,555,505, which is a continuation-in-part of application No. 15/891,410, filed on Feb. 8, 2018, now Pat. No. 10,395,503, which is a continuation of application
(Continued)

(51) Int. Cl.
| | |
|---|---|
| *G08B 21/12* | (2006.01) |
| *H04B 1/3888* | (2015.01) |
| *H04M 1/72412* | (2021.01) |
| *H04M 1/21* | (2006.01) |
| *G01N 33/00* | (2006.01) |
| *G01N 33/497* | (2006.01) |
| *G08B 25/10* | (2006.01) |

(52) U.S. Cl.
CPC .......... *G08B 21/12* (2013.01); *H04B 1/3888* (2013.01); *H04M 1/72412* (2021.01); *G01N 33/0009* (2013.01); *G01N 33/4972* (2013.01); *G08B 25/10* (2013.01); *H04M 1/21* (2013.01)

(58) Field of Classification Search
CPC ...... G08B 21/12; G08B 25/10; H04B 1/3888; H04M 1/7253; H04M 1/21; H04M 2250/04; H04M 2250/12; G01N 33/0009; G01N 33/4972; G06K 19/0717; G06K 19/0723
See application file for complete search history.

(56) References Cited

U.S. PATENT DOCUMENTS

| | | |
|---|---|---|
| 7,176,793 B1 | 2/2007 | Hummer |
| 7,667,593 B1 | 2/2010 | Hummer |
| (Continued) | | |

FOREIGN PATENT DOCUMENTS

WO  WO-2017044917 A1 * 3/2017 ......... G06K 19/0717

OTHER PUBLICATIONS

Article Application of Nanotechnology in Pesticides Removal from Aqueous Solutions—A review, T. Taghizade Firozjaee et al., Int. J. Nanosci. Nanotechnol., vol. 14, No. 1, Mar. 2018, pp. 43-56.

*Primary Examiner* — Daryl C Pope
(74) *Attorney, Agent, or Firm* — Lippes Mathias LLP

(57) ABSTRACT

Systems and methods for detecting, monitoring or measuring chemical concentrations in products intended for consumption or the environment of products intended for consumption throughout the supply chain, beginning with producers, processors, packagers, transporters, distributors and ending with retailers and consumers.

20 Claims, 32 Drawing Sheets

Related U.S. Application Data

No. 15/235,981, filed on Aug. 12, 2016, now Pat. No. 9,922,525.

(60) Provisional application No. 62/722,383, filed on Aug. 24, 2018, provisional application No. 62/485,084, filed on Apr. 13, 2017, provisional application No. 62/297,385, filed on Feb. 19, 2016, provisional application No. 62/205,012, filed on Aug. 14, 2015.

(56) References Cited

U.S. PATENT DOCUMENTS

| | | |
|---|---|---|
| 7,911,336 B1 | 3/2011 | Hummer |
| D641,013 S | 7/2011 | Richardson et al. |
| 8,204,561 B2 | 6/2012 | Mongan et al. |
| 8,629,770 B2 | 1/2014 | Hummer et al. |
| 8,674,827 B2 | 3/2014 | Hummer |
| 8,930,341 B2 | 1/2015 | Amin et al. |
| 9,241,054 B1 | 1/2016 | Roberts |
| 9,400,269 B2 | 7/2016 | Kambhampati |
| 9,466,057 B2 | 10/2016 | Beeson |
| 9,922,525 B2 | 3/2018 | Hummer |
| 2002/0093426 A1* | 7/2002 | Jackson ............ G06Q 30/0209 340/572.7 |
| 2004/0119591 A1 | 6/2004 | Peeters |
| 2005/0088299 A1* | 4/2005 | Bandy ................ G01N 33/0075 340/539.16 |
| 2006/0049714 A1 | 3/2006 | Liu |
| 2009/0153334 A1* | 6/2009 | Burns .................... B65D 51/20 340/572.8 |
| 2013/0049932 A1* | 2/2013 | Baym .................... A23L 35/00 340/10.1 |
| 2013/0049934 A1* | 2/2013 | Baym .................... G06K 19/02 340/10.1 |
| 2013/0271286 A1 | 10/2013 | Quan |
| 2014/0015643 A1* | 1/2014 | Shankman ......... G06K 19/0723 340/10.1 |
| 2014/0349707 A1 | 11/2014 | Bang |
| 2014/0377130 A1 | 12/2014 | Edwards |
| 2015/0180525 A1 | 6/2015 | Chen |
| 2015/0326061 A1 | 11/2015 | Davison |
| 2015/0359208 A1 | 12/2015 | Reckhaus |
| 2016/0077047 A1* | 3/2016 | Khamis .............. G01N 27/4146 506/3 |
| 2017/0360010 A1 | 12/2017 | Wilson-Rich |
| 2018/0038815 A1 | 2/2018 | Gu et al. |
| 2018/0103206 A1 | 4/2018 | Olson |
| 2018/0195987 A1* | 7/2018 | Hur ........................ G08B 21/14 |
| 2020/0051015 A1* | 2/2020 | Davis .................... G06Q 50/28 |

\* cited by examiner

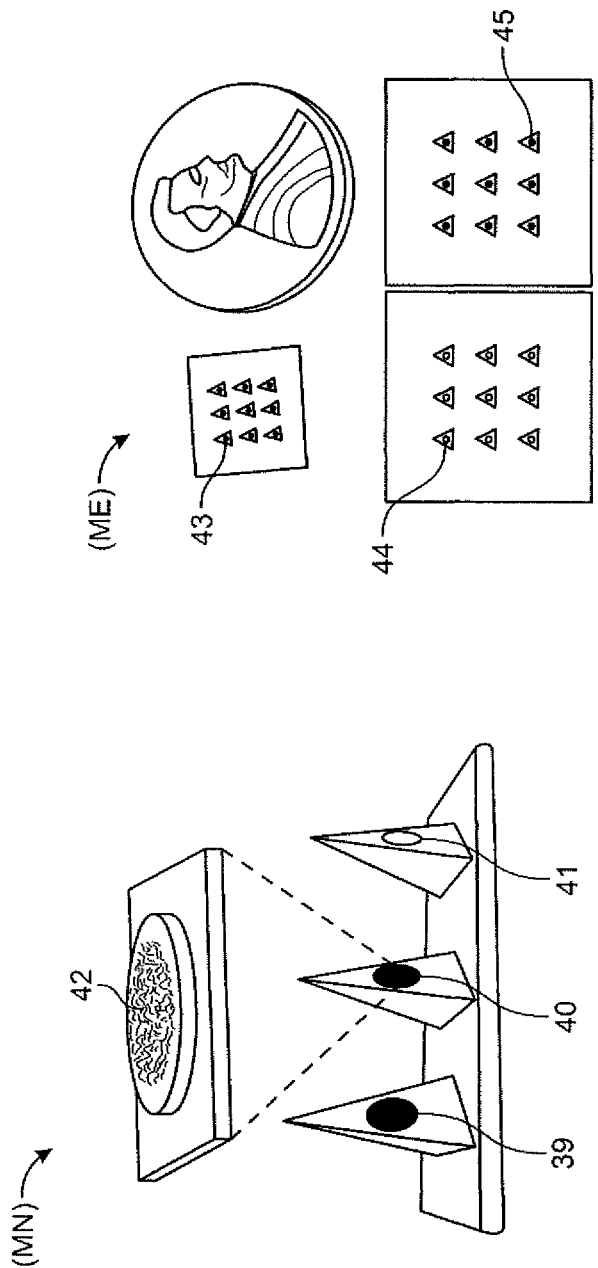

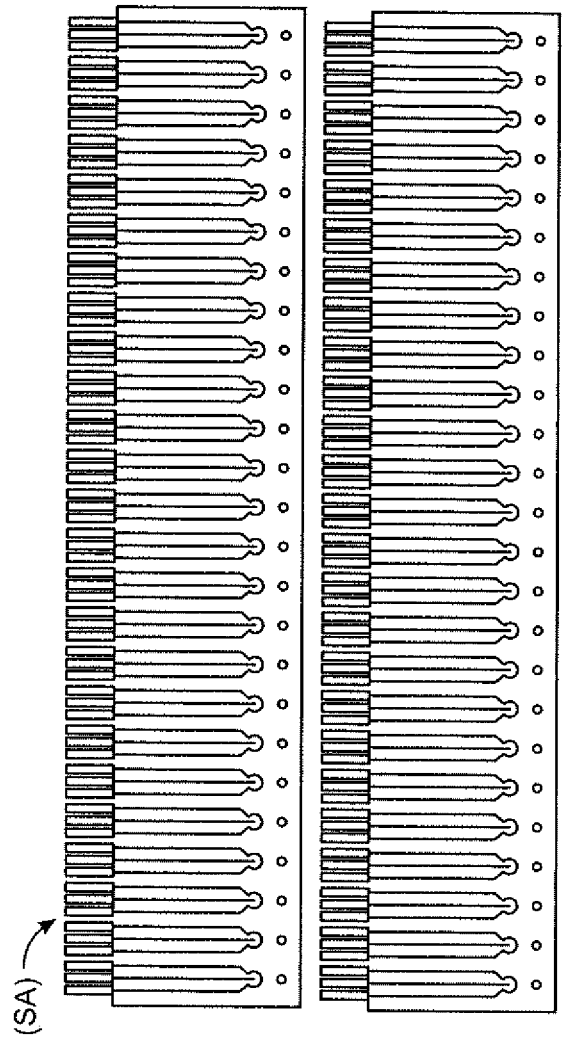
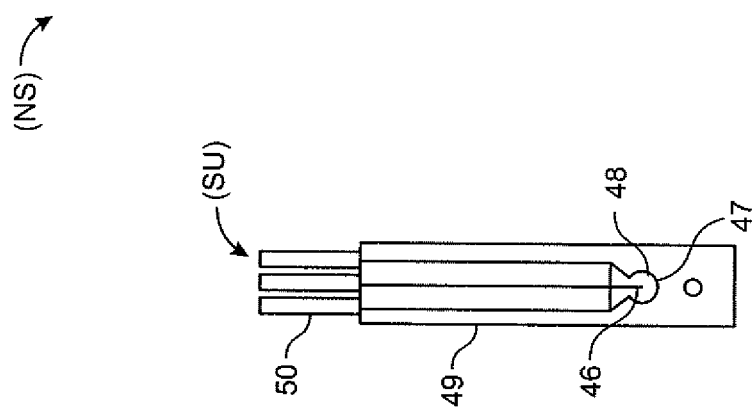
FIG. 3B(i)
FIG. 3B(ii)
FIG. 3B

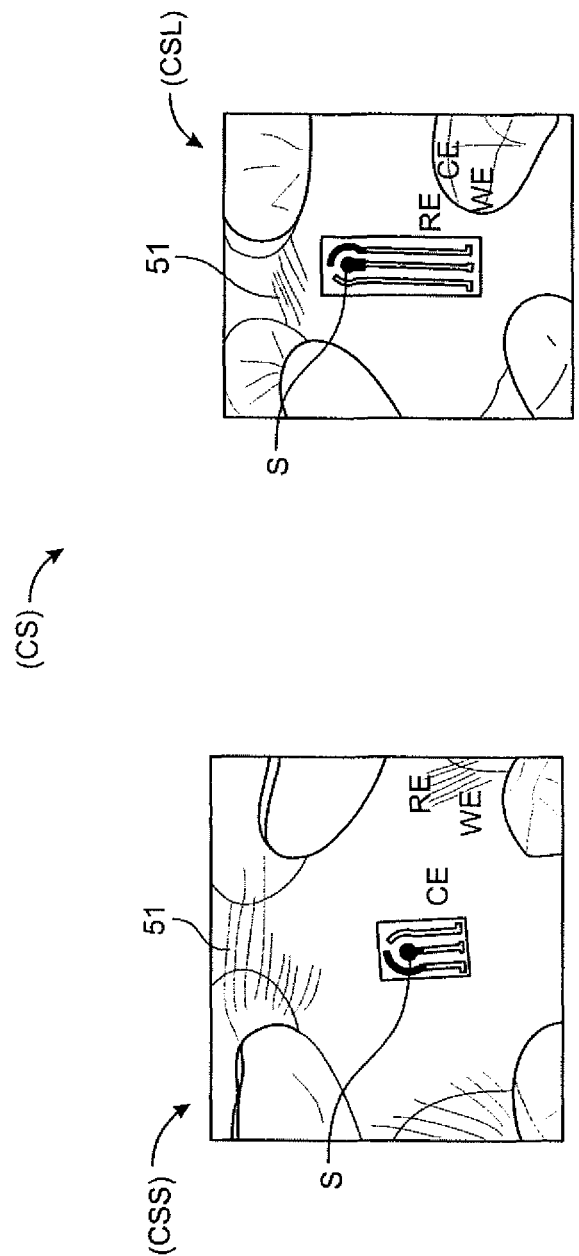

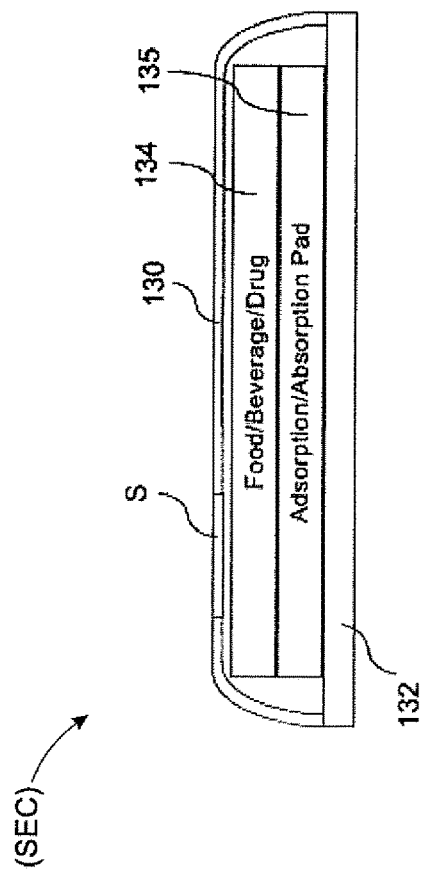
FIG. 17A (SOP)
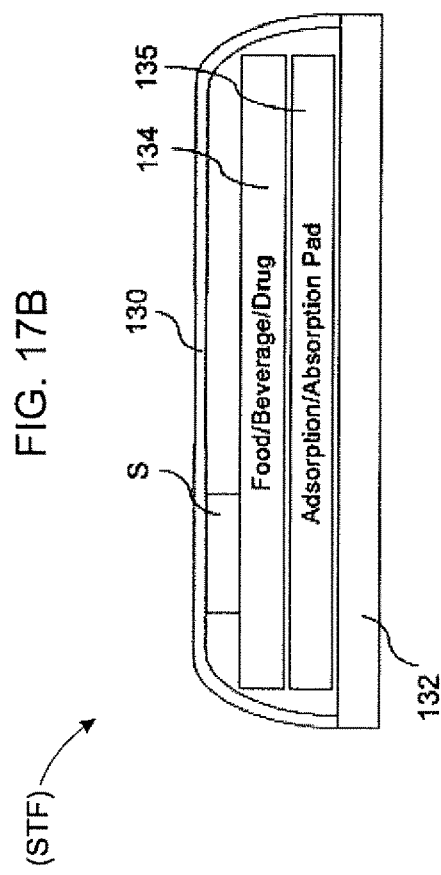
FIG. 17B (SEC)
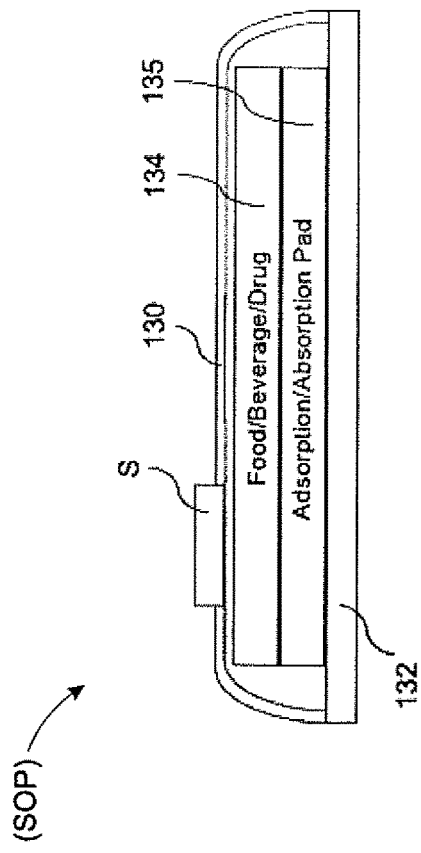
FIG. 17C (SNF)
FIG. 17D (STF)

SYSTEM AND METHOD OF DETECTING CHEMICALS IN PRODUCTS OR THE ENVIRONMENT OF PRODUCTS USING SENSORS

CROSS REFERENCE TO RELATED PATENTS AND APPLICATIONS

The present application is a continuation-in-part of U.S. patent application Ser. No. 16/549,158, filed Aug. 23, 2019, which application claims the benefit of U.S. Provisional Patent Application No. 62/722,383, filed Aug. 24, 2018, and is a continuation-in-part of U.S. patent application Ser. No. 15/951,500, filed Apr. 12, 2018, now abandoned, which application claims the benefit of U.S. Provisional Patent Application No. 62/485,084, filed on Apr. 13, 2017, and is a continuation-in-part of U.S. patent application Ser. No. 15/891,410, filed on Feb. 8, 2018, now U.S. Pat. No. 10,395,503, issued Aug. 27, 2019, which is a continuation of U.S. patent application Ser. No. 15/235,981, filed Aug. 12, 2016, now U.S. Pat. No. 9,922,525, issued Mar. 20, 2018, which claims the benefit of U.S. Provisional Patent Application Ser. No. 62/297,385, filed Feb. 19, 2016 and U.S. Provisional Patent Application Ser. No. 62/205,012, filed Aug. 14, 2015, which applications are hereby incorporated by reference.

FIELD

The present exemplary embodiment relates to devices, systems and methods for detecting chemicals and other factors. It finds particular application for products intended for consumption and the environment of products intended for consumption throughout the global supply chain, beginning with farmers, producers, packagers, transporters and distributors and ending with retailers and consumers.

BACKGROUND

Ensuring safe and nutritious consumable products for all is one of the most important public health challenges of our time. The safety of the products that we consume not only directly influences our health, but also is critical to the sustainability of the supply chain and broader environment and planet earth. However, ensuring a safe and secure supply has become more challenging than ever due to the sheer size and growing complexity and demands of today's global supply chains.

Among the major sources of contamination are water, air, dust, equipment, sewage, insects, rodents, and people. Contamination of raw materials can also occur from the soil, sewage, live animals, external surfaces, and the internal organs of meat animals and plants themselves. Additional contamination of animal products originates from diseased animals. Contamination from chemical sources can occur through accidental mixing of chemical supplies with products. Ingredients can contribute to additional microbial/macrobial or chemical contamination.

SUMMARY

This disclosure presents devices, systems and methods of detecting, tracking, monitoring and measuring chemicals, analytes and other unwanted factors in products intended for consumption or the environment of products intended for consumption throughout the global supply chain. The present application describes aspects of the invention in connection with food/beverage/drug. However, it should be appreciated that aspects of the invention are application to anything intended for consumption which includes, for example, food/beverage/drug, as well as any other product consumed or otherwise used by a person or animal. The disclosure presents various embodiments for addressing all the major sources of contamination among other sources of unwanted chemicals or other factors in consumable products. The disclosure also presents systems and methods for conducting various analysis of consumable products, many of which can be required by government agencies that regulate food, beverage, drug among other consumer products. Such analyses can include but are not limited to nutritional analysis, vitamin analysis, trace metal analysis, toxin analysis, allergen analysis, residue analysis, contamination analysis, melamine analysis, authenticity analysis, pesticide analysis among other analyses related to consumable products.

In general, the embodiments and methods presented entail attaching or embedding sensors to carried materials, packaging, wrapping, lining, bottles, cans, containers and equipment and even products themselves. Disclosed embodiments also include attaching or embedding sensors to various systems used to produce, grow, harvest, process, store, transport, distribute and sell products. The sensors are designed for real-time detection, monitoring and measuring as well as generating alerts when predetermined profiles of chemicals, analytes or other factors are detected.

Aspects of the present disclosure include a monitoring system for any type of product intended to be consumed in any type of setting, particularly a setting related to the global supply chain. In the exemplary embodiment, the monitoring system is deployed in various settings including, but not limited to systems for producing, farming, irrigating, pollinating, applying pesticides, harvesting, sorting, separating, processing, cleaning, packaging, bottling, canning, transporting, distributing, displaying and selling consumable products. However, it should be appreciated that the present exemplary embodiment is amenable to like applications particularly where chemicals can be detected in consumable products or the environment of consumable products.

Monitoring systems in accordance with the present disclosure can detect chemicals harmful to humans including those related to spoilage, contamination, pesticides, toxins, endotoxins, mycotoxins, pathogens, foodborne illness, viruses, bacteria and other types of chemical or biological material or unwanted elements. Other target chemicals or analytes include biogenic amines such as ammonia, dimethylamine, trimethylamine, cadaverine and histamine among other amines. Other targets can include heavy metals, adulterants, antibiotics among other unwanted factors such as fungi or moisture in foods or beverages or drugs or other consumable products.

The deployments of the monitoring systems are structured around four phases of the supply chain with the first phase being the farm or site where food/beverage/drug is produced or grown or caught or harvested. In this phase sensors detect threats to quality, safety and security during the production phase, including pesticides, spoilage, contamination, toxins, mycotoxins, pathogens, bacteria and other foodborne illness, biological materials or unwanted elements at the source (i.e. production facility, crop fields, fisheries, grazing fields, chicken coops etc. . . . ). The monitoring systems can be placed not only on materials and equipment that support the production process, but also placed on the food (e.g. plant or animal), beverage or drug or other consumable products.

The second phase includes processing, sorting, cleaning, separating and packaging or bottling/canning products whereby the product passes through a highly structured system and process ending with the appropriate packaging or boxing so it can be preserved, transported, stored and sold. In some situations, the highly structured system and process can be automated, requiring limited human oversight and handling.

The third phase includes transporting products whereby the product can be moved by multiple modes of transportation, encountering various types shipping and handling conditions (e.g. temperature, humidity, moisture etc.). In this phase the monitoring system monitors levels of spoilage and contamination throughout the journey among other chemical, biological material or other unwanted factors. The devices also monitor and track location as well as other factors that can include temperature, pH, moisture, humidity, light, pressure, shock, nutrient availability among other factors related to consumable products. The devices can be programmed to track spoilage conditions relative to a baseline average associated with a particular food or beverage or drug type and or particular shipping and handling condition. For foods, beverages, drugs and other products, temperature and location tracking are particularly important. The sensors can also be programmed in any such matter that aligns to a certain business decision criterion or any other matter deemed appropriate or important.

The fourth phase includes monitoring for harmful chemicals, including spoilage, contamination, toxins, endotoxins, mycotoxins, foodborne illness and pesticides when the product is under custody of the distributor, retailer or consumer. The present disclosure sets forth various methods of affixing and attaching sensor devices to individual packages or containers or wrappings or containers of products. The disclosure also sets forth various methods for affixing or attaching or embedding sensors in larger cases or containers or shelfing or racks or cold storage for storing, displaying and selling products. In this phase, the sensors could be programmed to signal alerts when spoilage or contamination is detected or reach certain levels associated with safe or unsafe consumption. The sensors can also be programmed to indicate optimal consumption time among other valuable data and information related to producers, distributors, transporters, retailers and consumers. In the fourth phase, the sensor devices can be of various types that wirelessly communicate with associated receivers that can be in the form of a personal communication device, remote terminal, smart infrastructure, smart equipment, among other types of suitable receivers.

Aspects of the present disclosure include sensor devices, systems and methods for producing data related to product freshness and contamination in all four phases of the global food supply chain. These data are collected, integrated, structured, processed and analyzed. They can be harnessed to create analytics dashboards that guide decisions related to optimal use of resources and assets; setting product prices that maximize sales revenue; accurate product ordering; efficient inventory management and for adopting appropriate food safety and security processes and protocols. In some instances, decision making can be automated and informed by data produced by the sensor devices and systems, requiring very little human intervention or oversight (e.g. a tasking system for store operators, stockers, pickers or other personnel or automated shopping assistant). Also, in instances where it is clear that a shipment or package will spoil prior to arrival, stakeholders including producers, shippers, distributors and retailers will be made aware, prompting an automatic re-order, discount or rebate associated with the spoiled food product.

The associated data can also be used to help identify the cause of spoilage and pinpoint when it occurred and the shipping and handling conditions causing it. This information can guide action aimed at preventing future loss from spoilage. Similarly, with contamination and foodborne illness, the data will pinpoint the location, providing more accuracy of the impact of the contamination. Such information will help avoid blanket recalls, minimizing the costs incurred by safety responses to illness outbreaks or other damage.

The data produced by the monitoring system can be made public or kept private. The data can be shared with others involved in the supply chain or may not be shared with others. In instances where the data is made public, the data can be augmented with data from other sources, including other sensor devices and data collection systems. The monitoring devices, systems and methods can also be driven by consumers, whereby the consumers have direct access to data related spoilage levels and possible contamination of products that they consider purchasing or end up purchasing.

Since identifying and tracking spoilage, pesticides, contamination and food-borne illness imposes heavy costs not only the private sector, but also the public sector, real-time monitoring of associated chemicals in accordance with aspects of the present disclosure can provide useful data and lower associated costs. Such data can be used not only to minimize food-borne illness that imposes an estimated annual cost of $15.2 billion a year but can also be used to lessen food waste that has an estimated annual cost of $1 trillion a year. Specifically, the data can be used to pinpoint where and when spoilage and contamination occurs and the shipping and handling conditions causing it. Predictive analysis can be used to anticipate and correct for spoilage, contamination and shrink by prioritizing shipments, automating the order process, smart re-routing among other shipping and handling tactics, product inventory management strategy and general resource allocation. The data can also be can be used to improve and verify compliance with government regulation including the Sanitary Transportation Act (SFTA) and Food Safety Modernization (FSMA) among other regulations, rules and guidelines related to food/beverage/drug safety and security.

The sensor system can comprise an array of monitor/detectors that are connected to an analyzer and memory, which can contain algorithms and can be downloaded from a central source, allowing the monitor/detector to detect and differentiate multiple chemicals or other factors in various phases including through physical contact or in gas phase or vapor phase or liquid phase among other types of phases. The sensors communicate with the CPU/memory and then report their findings via a standard wireless connection, near-field or other wireless connection including radio-frequency identification device (RFID) that can be encrypted for security purposes. Wired transmission of data can also be utilized in certain instances. The system can also include an active/passive power source and active/passive flow induction according to the present disclosure.

The present disclosure sets forth various types of sensors deployed on the outside of packages, on the inside of packages, attached to packages, embedded in packages, attached to carried material inside packages or attached to or embedded in consumable products or the environment of consumable products. The disclosed sensors are especially suitable for enclosed areas, semi-enclosed areas, open-air areas or surface areas that contact products or contact the environment of products. The sensors comprise of various materials including needles, wires, polymers or other conductive or suitable material. Sensor types comprise of biosensors, capacitive sensors, piezoresistive sensors, photodetectors, temperature sensor (e.g. thermocouples, thermistor, resistive temperature detectors), humidity sensors, moisture sensors, pressure sensors, light sensors, vibration sensors, image sensors, optical sensors, nano-sensors or gas sensors. A typical electrochemical monitor/detector has at least one electrode that can be invasive, minimally invasive or non-invasive. The detectors can be configured to sample an environment or sample fluid or other substance from the product itself or an environment associated with the product. Such sensors can be printed on various substrates or carried materials including cellophane or other types of covering or wrapping or package. Detectors can be aided by various fluids with sanitizing, cleaning and conductive properties (e.g. electrolyzed water, hydroxychloride among other suitable solutions). Another type of sensor can be configured to actively or passively sense an environment of enclosed areas, semi-enclosed areas, open-air areas or surface areas that come into contact with the product or the environment of the product. It should be appreciated that aspects of the present disclosure can be deployed in any suitable location or environment where monitoring of drugs or beverages or food or food byproducts is desirable.

For surface areas, sensors can be printed on or embedded in the surface areas themselves or on coverings for the surface area that can be in the form of plastic, paper, advanced material or other suitable materials used for lining and covering surface areas. Conveyors can be coated with materials that have embedded or attached sensors. Slicers, separators and other types of equipment that penetrate food can be outfitted with sensors that act as probes and sample the food when operating according to their normal function of slicing, plucking, probing, separating etc. Sorters and sifters can also be outfitted with sensors on surface areas that contact food or the food environment. Trays and other forms of handlers can be lined with paper or plastic that have embedded or attached sensors. Sensors can also be printed on trays or embedded in trays.

An exemplary application of the present disclosure includes deploying sensors inside or affixed to display cases or serving cases that are fully enclosed, partially enclosed or open-air. The cases can require controlling temperature, humidity or protection from other environmental elements or unwanted factors. In these display cases, sensors including those that function in various forms including through contact or gas phase or vapor phase or liquid phase and can be deployed according to the present disclosure. Sensors can be placed directly on the product; they can also be placed on serving trays or linings of serving trays within the case or on sides of the case or covering of the case among other areas of the case.

Sensors with active/passive flow induction or concentrators can also be used in cases. The flow inductors or concentrators push and/or pull air across the monitor/detector for enhanced detection, or otherwise induct air so as to more effectively expose the monitor/detector to contaminants/chemicals. These sensors can be placed on stands or other suitable infrastructure or equipment within the cases. For monitoring products that requires ice or other cooling agents, sensors that function in liquid can be strategically placed to sample chemicals in the ice/cooling agent or water melted from ice/cooling agent that was at one point in contact with the product being monitored or the environment of the product being monitored. Sensors can also be tagged directly to foods that reside on display shelves or in cases for chemical monitoring.

Open-air racks or stands that are used to display products can also be outfitted with sensors in accordance with aspects of the present disclosure. Sensors can be deployed on any portion of the equipment that comes into contact with the product or the environment of the product. Sensors with flow induction or concentrators can also be deployed to push and/or pull air or substance that has come into contact with the product across the sensors for chemical detection, or otherwise induct air or substance so as to more effectively expose the monitor/detector to potential contaminants/chemicals.

Aspects of the present disclosure can assist retailers in managing assets (e.g. cold storage, display cases, display stands etc.) by appropriately regulating temperature, humidity among other factors related to the quality, safety and security of products. Specifically, the application provides indication of whether the asset is performing in-line with desired outcomes of keeping food fresh and free from spoilage. For example, in certain instances, operators may find that setting the temperature of the cooling systems at a higher temperature may be just as effective at preserving food and preventing spoilage as setting the temperature at lower levels, thus saving energy. Furthermore, real-time readings of spoilage can be correlated with temperature and humidity settings of related assets. The data can be used to adjust, re-adjust and calibrate equipment based on the desired optimal outcomes to enhance efficiency.

The present disclosure also sets forth various methods of affixing or embedding the sensor in containers or boxes as well as affixing or embedding the sensors to linings or inner coatings of containers or boxes. The lining can span the entire container such that it forms a seal from the container wall, or the lining can span part of the container such that it forms a partial seal from the container wall. The sensors can also be deployed in inner walls or linings of open-air containers (e.g. bins, crates, dumpsters or open-end boxes etc.). Various sensor types can be used including biosensors, capacitive sensors, piezoresistive sensors, photodetectors, temperature sensors, humidity sensors, image sensors, optical sensors or gas sensors.

Another exemplary application for certain aspects of the present disclosure is an Expanded Polystyrene (EPS) Box. EPS boxes are used primarily to transport, store, display and sell foods, including but not limited to seafood, meat, produce among other consumable products. In this particular embodiment, a sensor can either resemble tags that are intended to remain affixed to food for the duration of the monitoring period or sensors attached to or embedded in an interior surface (e.g., the base/inner wall/cover) of the EPS box. Additional materials, such as adhesives, glue, gels, bands, clips, clamps, pins among other materials can be used to ensure contact between the sensor and the food being monitored. The sensors detect chemicals in various forms including through direct contact or vapor phase or gas phase or liquid phase.

Other methods for deploying the sensors inside of EPS boxes, include placing the sensor inside the box, free from any attachment to the box. Another method could include placing the sensor inside the box on a tether that limits movement of the detection device within the box. Another method could include embedding the sensors in the box. The sensor tags can also be attached directly to the food being monitored or they can also be attached to or embedded in an inner base/wall/cover of the EPS box. The placement of the sensor tag can be such that the tag has direct contact with the product being monitored or direct contact with the environment of the product being monitored; such an environment can include fluid, air, vapor or surface areas among other environments. Tags can also be attached to or embedded in removable linings, bags and other types of wrappings inside of EPS boxes.

Sensors designed to detect chemicals in liquid can be deposited inside of EPS boxes in a manner by which they can be submersed in liquid. Specific methods and designs include placing in a sump or other depression of the EPS designed to collect liquid. For example, an EPS box can be configured with a channel, well or other type of indentation in the box where fluid collects, and sensors can be placed to be submerged in liquid. The channels can either be isolated in one location or span area of the box. A second indentation could exist where the sensor electronics and power source can be placed as part of the sensor or system or apart from the sensor or system. These components are sealed and protected from harmful factors including fluid, humidity, extreme temperature and other factors proven to affect electrical or electronic elements or components. The electronics are enclosed in a fluid-resistant case or pouch or envelope prior to being embedded in the EPS box. For this particular application wires can be used to connect the sensors to the electronics and power source. The wires are placed in the channels along with the sensor devices.

Sensor devices can also be attached to or embedded in packs of ice or other types of cooling agents that produce liquids. The sensors can also have a greater density than the density of the fluid or can be tethered to an area of the box where fluid is most likely to collect.

An exemplary application for certain aspects of the present disclosure are pads that absorb gas or vapor or adsorb fluid or do both. Sensors are attached to or embedded in the pads and are configured to contact the product or contact fluids from the product. An exemplary embodiment well suited for such application includes a printed sensor strip comprising of a sensor device and a detection device. Portions of the strip can be enclosed in a housing, case or envelope resistant to various factors such as fluid, extreme temperature, pressure, shock among other factors known to impact the functionality of electrical or electronic elements or components.

An exemplary pad can consist of multiple layers or a single layer. In one embodiment the pad has at least three layers, where the base layer is the largest by surface area. The middle layer is the thickest and contains a hydrogel. The top layer can be the thinnest of all the three layers and can be coated with gel, paste, fluid or other material that improves functionality of the sensors and preserves the product.

Another exemplary application for certain aspects of the present disclosure include seals, caps, wrapping or covering for food, whereby sensors are attached or embedded in the wrapping. One configuration is such that the sensor stays in contact with the product, fluid from the product or the environment of the product. Another configuration does not require that the sensor stay in contact with the product.

In instances where the sensors are attached or embedded in seals, covers, caps or wrappings, additional package coverings, including stickers, cardboard sleeves among other materials can be used to hold elements or components of the sensor in place on the outside or inside of the package. These coverings can be designed to be removable in instances where the sensor elements or components are regularly removed and reused. In addition to having built-in methods to ensure the electronics are securely fastened to sensors, magnets between a printed circuit board and the sensor electrodes can be used to ensure connection between the board and sensor devices. Other such devices that ensure connection between electronic components and the sensors can also be used.

Disclosed embodiments relating to the sensors attached to or embedded in coverings can be deployed for foods that include dairy. For example, sensors can be attached or embedded in container seals and linings of such products like milk, yogurt, cheese among other related food products that typically have protective seals of some sort.

In accordance with another aspect, a method of monitoring area for the presence of or concentration level of one or more chemicals, the method comprises providing a plurality of sensors, each sensor including a detector component operative to generate data in response to the presence of one or more chemicals, communication circuitry and an active/passive power source operatively coupled to the detector component and the communication circuitry for supplying power thereto, the communication circuitry configured to transmit data generated by the detector component corresponding to the presence or absence of one or more chemicals to an associated receiver, associating each sensor with a location within the area being monitored, monitoring each location with its associated sensor over a period of time, and transmitting data generated by each sensors to a receiver. Other conditions of the area including temperature, humidity, moisture, light, pressure, vibration, shock among other factors may also be monitored and transmitted.

Each sensor can be configured to sense a concentration of the one or more chemicals. The method can further include approximating a location of ingress of the one or more chemicals into the area (or network of same) based at least in part on data generated by two or more sensors. The method can also include comparing the location and detected concentration of one or more chemicals of the two or more sensors to approximate the location of ingress of the one or more chemicals.

In some embodiments, the sensors can be configured to sense a concentration of the one or more chemicals and generate data indicative of the sensed concentration. The sensors can be configured to periodically report a sensed concentration over a period of time. The method can further include comparing the sensed concentration to a threshold concentration and generating an alert if the sensed concentration exceeds the threshold concentration. The method can also include providing an active/passive power source including an antenna configured to receive energy wirelessly and supply the received energy to at least one of the detector components or the communication circuitry. Radio-frequency identification devices (RFID) can also be used as a passive power source.

BRIEF DESCRIPTION OF THE DRAWINGS

FIGS. 3A-3C present exemplary monitor/detector in accordance with the present disclosure;

FIGS. 17A-17D illustrate exemplary deployments of sensors for packages, wrapping or containers in accordance with the present disclosure;

DETAILED DESCRIPTION

Figure 1:
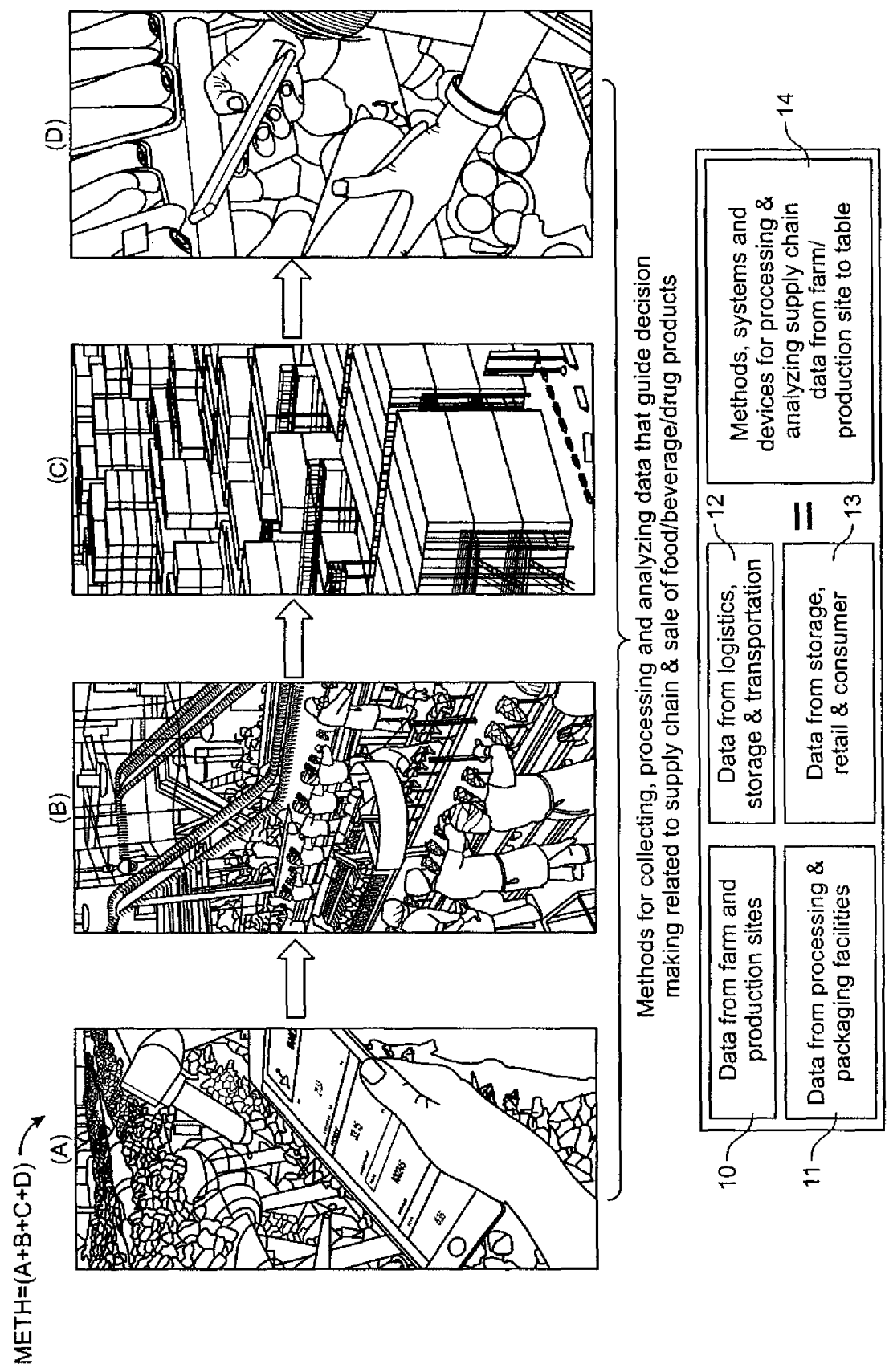
FIG. 1 illustrates the various phases of the supply chain and methods for collecting, processing and analyzing data.

The following description and examples illustrate some exemplary embodiments of the present disclosure in detail. Those of skill in the art will recognize that there are numerous variations and modifications of this invention that are encompassed by its scope. Accordingly, the description of a certain exemplary embodiment should not be deemed to limit the scope of the present disclosure.

Definitions

In order to facilitate an understanding of the preferred embodiments, a number of terms are defined below.

The term "analyte" as used herein is a broad term and is used in its ordinary sense, including, without limitation, to refer to a substance or chemical constituent in a biological fluid (for example, blood, interstitial fluid, cerebral spinal fluid, lymph fluid or urine) that can be analyzed. Analytes can include naturally occurring substances, artificial substances, metabolites, and/or reaction products. In some embodiments, the analyte for measurement by the sensing regions, devices, and methods are glucose, hypoxanthine, diamine, histamine, trimethylamine among others associated with spoilage, contamination and pathogens. However, other analytes are contemplated as well, including but not limited to acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, glucose-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, Plasmodium vivax, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free (3-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; glucose-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxy-progesterone; hypoxanthine phosphoribosyl transferase; immunoreactive trypsin; lactate; lead; lipoproteins ((a), B/A-1, β); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, Dracunculus medinensis, Echinococcus granulosus, Entamoeba histolytica, enterovirus, Giardia duodenalisa, *Helicobacter pylori*, hepatitis B virus, herpes virus, HIV-1, IgE (atopic disease), influenza virus, Leishmania donovani, leptospire, measles/mumps/rubella, *Mycobacterium leprae, Mycoplasma pneumoniae*, Myoglobin, Onchocerca volvulus, parainfluenza virus, Plasmodium falciparum, poliovirus, *Pseudomonas aeruginosa*, respiratory syncytial virus, rickettsia (scrub typhus), Schistosoma mansoni, Toxoplasma gondii, Trepenoma pallidium, Trypanosoma cruzi/rangeli, vesicular stomatis virus, Wuchereria bancrofti, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins and hormones naturally occurring in blood or interstitial fluids can also constitute analytes in certain embodiments. The analyte can be naturally present in the biological fluid, for example, a metabolic product, a hormone, an antigen, an antibody, and the like. Alternatively, the analyte can be introduced into the body, for example, a contrast agent for imaging, a radioisotope, a chemical agent, a fluorocarbon-based synthetic blood, or a drug or pharmaceutical composition, including but not limited to insulin; ethanol; cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbiturates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-dihydroxyphenylacetic acid (DOPAC), homovanillic acid (HVA), 5-hydroxytryptamine (5HT), and 5-hydroxyindoleacetic acid (FHIAA).

The term "nanoparticles" include particles between 1 and 100 nanometres (nm) in size with a surrounding interfacial layer. The interfacial layer is an integral part of nanoscale matter, fundamentally affecting all of its properties. The interfacial layer typically consists, in one example, of ions, inorganic and organic molecules. Organic molecules coating inorganic nanoparticles are known as stabilizers, capping and surface ligands, or passivating agents. In nanotechnology, a particle is defined as a small object that behaves as a whole unit with respect to its transport and properties. Particles are further classified according to diameter.

The term "graphene" includes an allotrope of carbon in the form of a single layer of atoms in a two-dimensional hexagonal lattice in which one atom forms each vertex. It is the basic structural element of other allotropes, including graphite, charcoal, carbon nanotubes and fullerenes. It can also be considered as an indefinitely large aromatic molecule, the ultimate case of the family of flat polycyclic aromatic hydrocarbons. Graphene has a special set of properties which set it apart from other allotropes of carbon. In proportion to its thickness, it is about 100 times stronger than the strongest steel. Yet its density is dramatically lower than any steel, with a surfacic mass of 0.763 mg per square meter. It conducts heat and electricity very efficiently and is nearly transparent. Graphene also shows a large and non-linear diamagnetism, even greater than graphite, and can be levitated by Nd—Fe—B magnets.

The term "biogenic amine" includes a biogenic substance with one or more amine groups. Biogenic amines are basic nitrogenous compounds formed mainly by decarboxylation of amino acids or by amination and transamination of aldehydes and ketones. Biogenic amines are organic bases with low molecular weight and are synthesized by microbial, vegetable and animal metabolisms. In food and beverages, they are formed by the enzymes of raw material or are generated by microbial decarboxylation of amino acids. There are two major categories of biogenic amines, Monoamines and Polyamines. Notable examples of Monoamines include histamine, serotonin, norepinephrine, epinephrine, dopamine, phenethylamines, tryptamines, trimethylamine, indoleamines and melatonin. Notable examples of Polyamines include agmatine, cadaverine, putrescine, spermine and spermidine.

The term "pathogen" includes anything that can produce disease. A pathogen may also be referred to as an infectious agent, or simply a germ. There are several pathways through which pathogens can invade a host. The principal pathways have different episodic time frames, but soil has the longest or most persistent potential for harboring a pathogen. Types of pathogens include prions, viruses, bacteria, fungi, algae and other parasites. Pathogen hosts include bacteria, plants, animals and humans. Specific pathogens include *Bacillus cereus, Campylobacter, Clostridium perfringens* toxin, *Escherichia coli*, Hepatitis A, *Listeria monocytogenes*, Norovirus, *Salmonella, Staphylococcus aureus* toxin, *Vibrio paprahaemolyticus*.

The term "toxin" includes a poisonous substance produced within living cells or organisms. Toxins can be small molecules, peptides, or proteins that are capable of causing disease on contact with or absorption by body tissues interacting with biological macromolecules such as enzymes or cellular receptors. Toxins vary greatly in their toxicity, ranging from usually minor (such as a bee sting) to almost immediately deadly (such as botulinum toxin). Types of toxins can include Hemotoxin, which causes destruction of red blood cells and Phototoxin, which causes dangerous photosensitivity. On a broader scale, toxins may be classified as either exotoxins, which are excreted by an organism, or endotoxins, which are released mainly when bacteria are lysed. The term "biotoxin" is used to explicitly confirm the biological origin of the toxin. Biotoxins can be further classified as fungal biotoxins, microbial toxins, plant biotoxins or animal biotoxins.

The term "contamination" includes the presence of a constituent, impurity, or some other undesirable element that spoils, corrupts, infects, makes unfit, or makes inferior a material, physical body, natural environment, workplace, etc. In chemistry, the term "contamination" usually describes a single constituent, but in specialized fields the term can also mean chemical mixtures, even up to the level of cellular materials. All chemicals contain some level of impurity. Contamination may be recognized or not and may become an issue if the impure chemical is mixed with other chemicals or mixtures and causes additional chemical reactions. In environmental chemistry, the term "contamination" is in some cases virtually equivalent to pollution, where the main interest is the harm done on a large scale to humans, organisms, or environments. An environmental contaminant may be chemical in nature, though it may also be a biological (pathogenic bacteria, virus, invasive species) or physical (energy) agent. Another type of environmental contaminant can be found in the form of genetically modified organisms (GMOs), specifically when they come in contact with organic agriculture. This sort of contamination can result in the decertification of a farm. In food chemistry and medicinal chemistry, the term "contamination" is used to describe harmful intrusions, such as the presence of toxins or pathogens in food or pharmaceutical drugs.

The term "spoilage" includes the process where a food/beverage/drug product becomes unsuitable to ingest by the consumer. The cause of such a process is due to many outside factors as a side-effect of the type of product it is, as well as how the product is packaged, stored or transported. Due to spoilage, one-third of the worlds' food produced for the consumption of humans is lost every year. Bacteria and various fungi are the cause of spoilage and can create serious consequences for the consumers.

The term "bacteria" includes a large domain of prokaryotic microorganisms. Typically a few micrometres in length, bacteria have a number of shapes, ranging from spheres to rods and spirals. Bacteria were among the first life forms to appear on earth and are present in most of its habitats. Bacteria inhabit soil, water, acidic hot springs, radioactive waste and the deep biosphere of the earth's crust. Bacteria also live in symbiotic and parasitic relationships with plants and animals. Most bacteria have not been characterized, and only about 27 percent of the bacterial phyla have species that can be grown in the laboratory.

The term "fungi" includes a form of spoilage that includes mold and yeast. Fungi are caused by acidifying, fermenting, discoloring and disintegrating processes and can create fuzz, powder and slimes of many different colors, including black, white, red, brown and green.

The term "other factor" can include but is not limited to temperature, location, speed, flow (e.g. air, liquid or other substance), pH, nutrients (e.g. nutrient availability), moisture, humidity, light, pressure, vibration, radiation, shock, among other factors that can be monitored or measured by detection devices throughout the supply chain of food/beverage/drug. Other types of analysis that can be conducted by the monitoring system include nutritional analysis, vitamin analysis, trace metal analysis, natural toxins and allergens analysis, residue and contamination analysis, melamine analysis, authenticity testing or analysis, pesticide analysis or acrylamide testing or analysis.

The term "host" as used herein is a broad term and is used in its ordinary sense, including, without limitation, to refer to seafood and meat such as fish, mammals, birds and other categories of vertebrates and non-vertebrates.

The phrase "continuous (or continual) analyte sensing" as used herein is a broad term and is used in its ordinary sense, including, without limitation, to refer to the period in which monitoring of analyte concentration is continuously, continually, and or intermittently (regularly or irregularly) performed, for example, about every 3 to 20 minutes.

The term "electrochemically reactive surface" as used herein is a broad term and is used in its ordinary sense, including, without limitation, to refer to the surface of an electrode where an electrochemical reaction takes place. For example, a working electrode measures hydrogen peroxide produced by the enzyme-catalyzed reaction of the analyte detected, which reacts to create an electric current. Glucose analyte can be detected utilizing glucose oxidase, which produces H2O2 as a byproduct. H2O2 reacts with the surface of the working electrode, producing two protons (2H+), two electrons (2e−) and one molecule of oxygen (O2), which produces the electronic current being detected.

The term "electronic connection" as used herein is a broad term and is used in its ordinary sense, including, without limitation, to refer to any electronic connection known to those in the art that can be utilized to interface the sensing region electrodes with the electronic circuitry of a device, such as mechanical (for example, pin and socket) or soldered electronic connections.

The term "electrical connection" includes an electromechanical device used to join electrical terminations and create an electrical circuit. Most electrical connectors have a gender (e.g. the male component, called a plug, connects to the female component, or socket). The connection may be removable (e.g. as for portable equipment), require a tool for assembly and removal, or serve as a permanent electrical joint between two points. An adapter or connector can be used to join dissimilar connectors.

The term "adapter" includes a device that converts attributes of one device or system to those of an otherwise incompatible device or system. Some modify power or signal attributes, while others merely adapt the physical form of one connector to another.

The term "connector" includes an electromechanical device used to join electrical terminations and create an electrical circuit. Most electrical connectors have a gender (e.g. the male component, called a plug, connects to the female component, or socket). The connection may be removable (as for portable equipment), require a tool for assembly and removal, or serve as a permanent electrical joint between two points. An adapter can be used to join dissimilar connectors.

The term "printed electronics" includes a set of printing methods used to create electrical devices on various substrates. Printing typically uses common printing equipment suitable for defining patterns on material, such as screen printing, flexography, gravure, offset lithography, and inkjet. By electronic industry standards, these are low cost processes. Electrically functional electronic or optical inks are deposited on the substrate, creating active or passive devices, such as thin film transistors; capacitors; coils; resistors. Printed electronics is facilitating widespread, very low-cost, low-performance electronics for applications such as flexible displays, smart labels (e.g. for food/beverage/drug), decorative and animated posters, and active clothing that do not require high performance.

The term "interferant" and "interferants," as used herein, are broad terms and are used in their ordinary sense, including, without limitation, to refer to species that interfere with the measurement of an analyte of interest in a sensor to produce a signal that does not accurately represent the analyte measurement. In one example of an electrochemical sensor, interferants are compounds with oxidation potentials that overlap with the analyte to be measured.

The terms "operable coupled" and "operably connected" and "operably linked" as used herein are broad terms and are used in their ordinary sense, including, without limitation, to refer to one or more components linked to one or more other components. The terms can refer to a mechanical connection, an electrical connection, or a connection that allows transmission of signals between the components. For example, one or more electrodes can be used to detect the amount of analyte in a sample and to convert that information into a signal; the signal can then be transmitted to a circuit. In such an example, the electrode is "operably linked" to the electronic circuitry.

The term "baseline" as used herein is a broad term and is used in its ordinary sense, including, without limitation, is the component of an analyte sensor signal that is not related to the analyte concentration. In one example of a hypoxanthine sensor, the baseline is composed substantially of signal contribution due to factors other than hypoxanthine (for example, interfering species, non-reaction-related hydrogen peroxide, or other electroactive species with an oxidation potential that overlaps with hydrogen peroxide). In some embodiments wherein a calibration is defined by solving for the equation y=mx+b, the value of b represents the baseline of the signal.

The term "algorithm," as used herein, is a broad term and is used in its ordinary sense, without limitation, to refer to a computational process (for example, programs) involved in transforming information from one state to another, for example, by using computer processing, The term "regression," as used herein, is a broad term and is used in its ordinary sense, including, without limitation, to refer to finding a line for which a set of data has a minimal measurement (for example, deviation) from that line. Regression can be linear, non-linear, first order, second order, or the like. One example of regression is least squares regression.

The term "calibration," as used herein, is a broad term and is used in its ordinary sense, including, without limitation, to refer to the process of determining the relationship between the sensor data and the corresponding reference data, which can be used to convert sensor data into meaningful values substantially equivalent to the reference data. In some embodiments, namely, in continuous analyte sensors, calibration can be updated or recalibrated over time as changes in the relationship between the sensor data and reference data occur, for example, due to changes in sensitivity, baseline, transport, metabolism, or the like.

The terms "interferants" and "interfering species," as used herein, are broad terms and are used in their ordinary sense, including, without limitation, to refer to effects and/or species that interfere with the measurement of an analyte of interest in a sensor to produce a signal that does not accurately represent the analyte concentration. In one example of an electrochemical sensor, interfering species are compounds with an oxidation potential that overlap that of the analyte to be measured, thereby producing a false positive signal.

The term expanded polystyrene (EPS) includes a rigid and tough, closed-cell foam with a normal density range of 11 to 32 $kg/m^3$ and made of pre-expanded polystyrene beads. Due to its technical properties such as low weight, rigidity, formability as well as its insulation and anti-flammable properties, EPS can be used in a wide range of applications, helping to boost sales that are estimated to be more than $15 billion U.S. dollars by 2020. Among the many applications of EPS are food containers, including those used for food retail and food services. At the food retail level, EPS boxes are used predominantly to transport, store and display seafood and meats, but are also used for fruits and vegetables. EPS vary in size and thickness, depending on the use and are often custom designed and manufactured for certain foods and the respective voyage. The boxes can be reusable but are more often disposed of after a single use.

The term "self-healing material" is defined as including autonomously self-healing or a healing process that occurs without human intervention. Self-healing polymers may, however, activate in response to an external stimulus (e.g. light, temperature change, humidity change, moisture change etc.) to initiate the healing processes. Self-healing materials are artificial or synthetically created substances which have the built-in ability to automatically repair damage to themselves without any external diagnosis of the problem or human intervention. Generally, materials will degrade over time due to fatigue, environmental conditions, or damage incurred during operation. Cracks and other types of damage on a microscopic level have been shown to change thermal, electrical, and acoustical properties of materials, and the propagation of cracks can lead to eventual failure of the material. In general, cracks are hard to detect at an early stage, and manual intervention is required for periodic inspections and repairs. In contrast, self-healing materials counter degradation through the initiation of a repair mechanism which responds to the micro-damage. Some self-healing materials are classed as smart structures and can adapt to various environmental conditions according to their sensing and actuation properties. Although the most common types of self-healing materials are polymers or elastomers, self-healing covers all classes of materials, including metals, ceramics, and cementitious materials. Healing mechanisms vary from an intrinsic repair of the material to the addition of a repair agent contained in a microscopic vessel.

The term "ripening" includes a process primarily in fruits that causes them to become more palatable. In general, fruit becomes sweeter, less green (typically "redder"), and softer as it ripens. Even though the acidity of fruit increases as it ripens, the higher acidity level does not make the fruit seem tarter. This is attributed to the Brix-Acid Ratio.

The term "ripening agent" includes an agent that speeds up the ripening process. The agents allow many fruits to be picked prior to full ripening, which is useful, since ripened fruits do not ship well. For example, bananas are picked when green and artificially ripened after shipment by being gassed with ethylene. Calcium carbide is also used in some countries for artificially ripening fruit. When calcium carbide comes in contact with moisture, it produces acetylene gas, which is quite similar in its effects to the natural ripening agent, ethylene. Acetylene acts like ethylene and accelerates the ripening process. Industrial-grade calcium carbide may also contain traces of arsenic and phosphorus which makes it a human health concern. Climacteric fruits are able to continue ripening after being picked, a process accelerated by ethylene gas. Non-climacteric fruits can ripen only on the plant and thus have a short shelf life if harvested when they are ripe.

The term "polymer hydrogel" includes a network of polymer chains that are hydrophilic, sometimes found as a colloidal gel in which water is the dispersion medium. A three-dimensional solid result from the hydrophilic polymer chains being held together by cross-links. Because of the inherent cross-links, the structural integrity of the hydrogel network does not dissolve from the high concentration of water. Hydrogels are highly absorbent (they can contain over 90% water) natural or synthetic polymeric networks. Common uses of hydrogel include: tissue engineering, cell culture, sense changes in pH, temperature, or concentration of metabolite, drug delivery, absorption, desloughing and debriding of necrotic and fibrotic tissue, biosensors, disposable diapers, contact lenses, medical electrodes and glue.

The term "spectral imaging" includes imaging that uses multiple bands across the electromagnetic spectrum. While an ordinary camera captures light across three wavelength bands in the visible spectrum, red, green and blue (RGB), spectral imaging encompasses a wide variety of techniques that go beyond RGB. Spectral imaging may use the infrared, the visible spectrum, the ultraviolet, x-rays, or some combination of the above. It may include the acquisition of image data in visible and non-visible bands simultaneously, illumination from outside the visible range, or the use of optical filters to capture a specific spectral range. It is also possible to capture hundreds of wavelength bands for each pixel in an image. Hyperspectral imaging is another subcategory of spectral imaging, which combines spectroscopy and digital photography. In hyperspectral imaging, a complete spectrum or some spectral information (such as the Doppler shift or Zeeman splitting of a spectral line) is collected at every pixel in an image plane. A hyperspectral camera uses special hardware to capture hundreds of wavelength bands for each pixel, which can be interpreted as a complete spectrum. In other words, the camera has a high spectral resolution.

The term hydroxychloride (HOCL) includes the chemical white blood cells produce and use to combat pathogens. HOCL destroys bacteria, yeasts, fungus, mold and viruses.

The term "gender" of connectors and fasteners includes the pairing or mating of electrical or mechanical elements or components. The "female" connector is generally a receptacle that receives and holds the "male" connector. On occasion, the terms "male" and "female" are respectively referred to as the A and B ends, though the names of some standards conflict with this as they contain the letters A or B within the name. Sometimes the less ambiguous terms plug and socket or jack are used, particularly in reference to electrical connectors.

The term "materials or equipment or devices" that contact food or the environment of food can includes: boxes, bags, bins, cases, crates, containers, countertops, conveyors, displays, freezers, dumpsters, packages, processors, racks, refrigerators, shelves, stands, slicers, separators, trays, wrappings and other types of enclosed, semi-enclosed, open-air or surface areas are used in the process of producing food; selling food and otherwise handling a wide variety of food and inputs to food. Other types of materials can include agriculture production infrastructure and equipment such as irrigation ditches, flow conduits, water distribution mechanisms, wells, honeybee and other social insect colonies and equipment that encounters crops and the environment that nurtures their growth. The materials can also include surface areas whereby food passes for harvesting, processing, separating, slicing, cleaning and packaging. Examples include conveyors, slicers, sifters, separators, trays, countertops and other food cleaning, processing and preparation surface areas. The materials also include those used for storing, distributing, transporting, displaying and selling food. Furthermore, materials include anything that touches food or the environment of food.

The term "food" includes any substance consumed to provide nutritional support to an organism. Food is usually of plant or animal origin, and contains essential nutrients, such as carbohydrates, fats, proteins, vitamins, or minerals. The substance is ingested by an organism and assimilated by the organism's cells to provide energy, maintain life, or stimulate growth. It should be appreciated for ease of use and the purpose of this disclosure in its entirety the term "food" is to include beverages, drinks, supplements, vitamins or drugs, all of which are referred to as "food" throughout the disclosure.

The term "beverage" includes a liquid intended for human consumption. In addition to their basic function of satisfying thirst, drinks play important roles in human culture. Common types of drinks include plain drinking water, milk, coffee, tea, hot chocolate, juice and soft drinks. In addition, alcoholic drinks such as wine, beer, and liquor, which contain the drug ethanol are known as beverages.

The term "drug" is any substance that causes a change in an organism's physiology or psychology when consumed. Drugs are typically distinguished from food and substances that provide nutritional support. However, for the purposes of this disclosure, drugs, drinks and beverages are commonly referred to throughout as "food".

The term "vacuum packing" and can be defined as a method of packaging that removes air from the packaging prior to sealing. This method involves (manually or automatically) placing items in a plastic film package, removing air from inside, and sealing the package. Shrink film is sometimes used to have a tight fit to the contents. The intent of vacuum packing is usually to remove oxygen from the container to extend the shelf life of foods and, with flexible package forms, to reduce the volume of the contents and package. Vacuum packing reduces atmospheric oxygen, limiting the growth of aerobic bacteria or fungi, and preventing the evaporation of volatile components. It is also commonly used to store dry foods over a long period of time, such as cereals, nuts, cured meats, cheese, smoked fish, coffee, and potato chips. On a more short-term basis, vacuum packing can also be used to store fresh foods, such as vegetables, meats, and liquids, because it inhibits bacterial growth.

The term "shrink wrap" also known as "shrink film" includes a material made up of polymer plastic film. When heated is applied, it shrinks tightly over whatever it is covering. Heat can be applied with a handheld heat gun (electric or gas) or the product film can pass through a heat tunnel on a conveyor. The most commonly used shrink wrap is polyolefin. It is available in a variety of thicknesses, clarities, strengths and shrink ratios. The two primary films can be either crosslinked, or non-crosslinked. Other shrink films include PVC, polyethylene, polypropylene, and several other compositions. Coextrusions and laminations are available for specific mechanical and barrier properties for shrink wrapping food. For example, five layers might be configuration as EP/EVA/copolyester/EVA/EP, where EP is ethylene-propylene and EVA is ethylene-vinyl acetate copolymer.

The term "corrective action" includes any measures or action taken in response in-part from data or information gathered by the monitor/detector component of the sensor as well as other components or elements of the sensor. Corrective action could include but is not limited to: altering conditions for growing, producing, harvesting, processing, packaging, transporting, distributing, storing or selling food/beverage/drug.

Turning to the FIGURES, FIG. 1 illustrates methods for collecting, processing and analyzing data related to food/beverage/drug using detection devices and detection systems (METH). The data can relate to chemicals, biological materials, analytes and other factors associated with food/beverage/drug throughout the four phases of the supply chain (A+B+C+D=METH). The supply chain beginning with farmers, producers, hunters, gathers and fishers (A), followed by processing, packaging and bottling/canning (B), followed by the logistics, transportation, distribution (C); and the final phase is selling at the retail level to a consumer (D). FIG. 1 also presents exemplary applications for data collection using devices and systems in accordance with the present disclosure to detect, monitor or measure chemicals, analytes, biological materials or other factors in food/beverage/drug or environments associated with food/beverage/drug throughout the four stages of the supply chain (A+B+C+D=METH).

Phase (A) focuses on collecting data from farms or production sites. Such data can include factors such as the use of pesticides, contaminants, antibiotics, additives, adulterants as well as other chemicals associated with quality, standards, safety and security, Specific factors can include the presence of pathogens, viruses, bacteria, fungi, illness and unwanted adulterants or additives (10). On farms or production sites, sensors can be deployed on or in crops, plants, soil, water sources, stands located throughout growing fields, as well as farming infrastructure or equipment along with broader agriculture ecosystems and environments. A specific example according to the present disclosure is placing sensors inside of colonies of social insects, including pollinators such as honey bees. The sensors are not only capable of chemical detection, but also capable of monitoring and measuring other factors related to agriculture production, which can include temperature, humidity, moisture, light, pressure, nutrient availability, vibration, pH among other factors associated with the production of agricultural products.

Phase (B) focuses on collecting data from processing, packaging or bottling/canning facilities. Such data can include chemicals, biological materials and other factors associated with food/beverage/drug standards, safety and security such as: pathogens, bacteria, toxins, endotoxins, mycotoxins, viruses, heavy metals, pasteurization, fermentation and other unwanted chemicals, adulterants, additives or other factors (11). In processing and packaging plants or bottling and canning facilities, sensors are placed in enclosed, semi-enclosed, open-air or surface areas that come into contact with food/beverage/drug directly or indirectly. Such areas can include, but are not limited to: countertops, conveyors, slicers, separators, sifters, grinders, processors, bins, crates, bowls, drums, trays, stands, tanks, pipes, flow conduits, containers, vats and other cleaning, processing, preparation or pasteurization and fermentation areas.

Phase (C) focuses on collecting data from the logistics, storage, transportation and distribution portion of the supply chain. Such data can include chemicals, biological material, analytes and other factors associated with food standards, safety and security (12). Throughout the transportation supply chain, sensors are placed in enclosed, semi-enclosed, open-air or surface areas that come into contact with food/beverage/drug directly or indirectly. Such areas include but are not limited to: cargo containers, trailers, carts, cans, cartons, food containers, boxes, bins, bottles, cold storage, packaging, bags, wrapping among other materials or equipment used for transporting, storing, distributing food/beverage/drug or moving food/beverage/drug from one place to another.

Phase (D) focuses on collecting data at the retail and consumer levels of the supply chain. Similar to the other phases, the data are related to food/beverage/drug standards, safety and security (13). At the retail and consumer levels, sensors are placed in enclosed, semi-enclosed, open-air or surface areas that come into contact with food/beverage/drug directly or indirectly. Such areas include, but are not limited to: bins, bottles, crates, containers, cans, trays, boxes, packages, bags, wrapping, cases among other equipment, materials or devices used to store, display, sell and consume food/beverage/drug.

Data from all four phases (A+B+C+D) are gathered, processed, analyzed and displayed in analytic dashboards that help guide decision making related to capital, plant and equipment as well as food/beverage/drug safety and security protocols (14). The four phases of the food/beverage/drug supply chain (A+B+C+D) are exemplary in nature. Aspects of the present disclosure can be implemented in virtually any setting where food/beverage/drug is produced, processed, transported, displayed, sold and consumed. This includes, but is not limited to distributors, retailers and stores but also restaurants, events, cafeterias and other venues where food/beverage/drug is sold or consumed. In the four exemplary supply chain phases (A+B+C+D), data associated with pesticides, antibiotics, adulteration, additives, biological materials, spoilage and contamination is the focus, but the applications can be extended to any type of chemical, biological material, analyte or other factor related to food/beverage/drug. FIG. 1 illustrates several exemplary applications and locations for the sensors, but it should be appreciated that sensors can also be placed in other locations not specified in this disclosure. It should also be appreciated that the data collected from the four phases (A+B+C+D) can be shared among public and private sector stakeholders with the purpose of improving food/beverage/drug standards, safety and security, specifically minimizing outbreak of foodborne/beverage illness. The data can be shared within a country and also can be shared among countries since supply chains are global in nature. The data can be augment or enhanced with additional data and visualized using analytics tools. These data can be shared with industry stakeholders as well as the broader food/beverage/drug consuming public. Sharing such data would limit the impact of contamination outbreak and allow the food consuming public to gain confidence in supply chains, especially in such instances where food/beverage/drug types are identified as contamination. In general, the objective of the present disclosure is to not only track and trace spoilage and contamination for resource optimization and sustainability purposes for stakeholders of food/beverage/drug, but also to provide assurance to consumers that the food/beverage/drug they purchase and consume are free from threats to safety and security and are of the highest quality.

Figure 2:
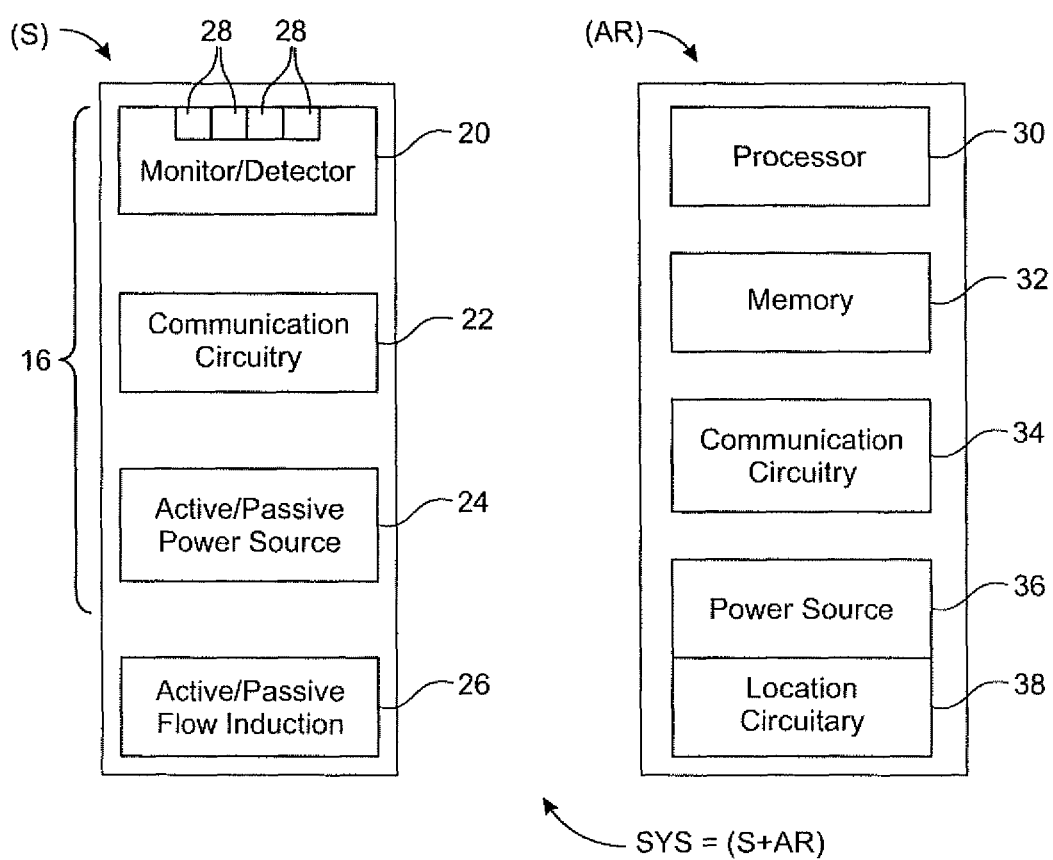
FIG. 2 is a block diagram of an exemplary system in accordance with the present disclosure.

FIG. 2 presents a general configuration of an exemplary system for detecting, monitoring or measuring chemicals, analytes and other factors in food/beverage/drug or the environment of food/beverage/drug throughout the supply chain. The system comprising of two major components, each of which have several sub-components. The first major component is a sensor (S) and the second major component is an associated receiver (AR). Therefore, the system for detecting, monitoring or measuring chemicals, analytes and other factors in food/beverage/drug or the environment of food/beverage/drug throughout the supply chain can be known as (SYS=S+AR).

It should be appreciated that the two major components, the sensor (S) and the associated receiver (AR) can consist of various forms and include a wide variety of additional components or elements as is conventional. The sensor (S) can be of macro, micro, meso or nanosized, all of which are referred to throughout as nanosensors, for detecting materials harmful to human beings in food or beverages or drugs or in the environment of food or beverage or drug, all of which can be referred to throughout as food. Some of the sensor types, transmit a corresponding resonance frequency, while other types produce a digital output of data. Sensor (S) types can include temperature, humidity, moisture, pH, light, pressure, vibration, proximity, location, level, accelerometer, gyroscope, chemical, gas, smoke, water quality, infrared, image, motion, optical among sensors for detecting other factors associated with food/beverage/drug. The associated receiver (AR) can be in the form of a personal communication device, cell phone, smartphone, remote terminal or wearable devices that can include smart watches, peripheral devices, glasses, clothing among other types of on-body or in-body or embedded electronics. Other forms of an associated receiver (AR) can include any type of equipment that has electrical or electronic elements or components and is capable of receiving data. Traditional equipment such as: farming equipment, processing equipment, packaging equipment, bottling equipment, transportation equipment, distribution equipment, storage equipment, retail equipment (e.g. cases, containers, racks shelves, signs etc.) can all be modified or outfitting with associated receivers (AR). As such, infrastructure or equipment that receives data or transmission signal can be known as "smart infrastructure" or "smart equipment" referred to throughout this disclosure.

With reference to FIG. 2, the monitoring system (16), as part of the system for detecting, monitoring or measuring chemicals, analytes or other factors (SYS), generally includes a monitor/detector component (20). One monitor/detector component (20) that is particularly well-suited for purposes of the present disclosure is set forth in U.S. Pat. No. 8,629,770 to Hummer et al. and U.S. Pat. No. 7,176,793 to Hummer and U.S. Pat. No. 9,922,525 to Hummer et al, all of which are incorporated herein by reference in their entireties. Other types of monitor/detector components can also be used in accordance with the present disclosure and are set forth in FIGS. 3A-3C.

The monitoring system (16) also includes communication circuitry (22) and an active/passive power source (24). The communication circuitry (22) can include at least one of a near field communication device, radio-frequency identification device, Bluetooth communication device, WIFI communication device, or any other suitable communication circuitry for establishing communications with the associated receiver (AR). The power source (24) can be a power supply such as a battery (lithium or other) mounted or printed or otherwise contained in the monitoring system (16). The battery can also be printed and be part of the monitor/detector (20). The power source (24) can also be an antenna configured to receive energy wirelessly and supply the received energy to one or both of the monitor/detector component (20) and/or communication circuitry (22) such that no onboard battery is required for operation of the monitor system (16). A specific embodiment can include radio-frequency identification that uses electromagnetic fields to automatically identify and track tags placed inside or attached to or embedded in objects that contain electronically stored information about the presence of chemicals in food. These passive tags collect energy from nearby RFID reader's interrogating radio waves. The tags communicate with associated receivers (AR), which can be an element or component of "smart infrastructure" or "smart equipment". Another arrangement includes a power source (24) in the form a connector configured to couple with a port of an associated receiver (AR) such as personal communication device, smart infrastructure, smart equipment, wearable or on-body or in-body or embedded electronic to receive power from a power source of the associated receiver (AR). Exemplary embodiments of sensors (S) connecting to forms of "smart infrastructure" or "smart equipment" are disclosed in FIGS. 15A-15D, whereby the "smart equipment" not only serves as an associated receiver (AR), but also supplies the communication circuitry (22) and the power source (24) of the monitoring device (16). As such, the monitor/detector (20) is a removeable/replaceable unit of the smart infrastructure or smart equipment that can be in the form of a rack, shelf, stand, sign among other types of infrastructure or equipment.

An active/passive flow induction device (26) can be provided for ensuring adequate and or continuous flow of vapor or air or liquid or other substance to the monitor/detector (20). Such devices can include concentrators in the form of fans, pumps, channel flow paths, micropumps, louvers, vents, housing, pouch, case, envelope etc. An active induction device (26) can be separately removable and replaceable within the monitoring system (16) and can include its own power supply. Alternatively, an active induction device can be configured to receive power from the power supply (24).

It should be appreciated that the active/passive flow induction (26) does not have to be part of the sensor (S). For example, in applications where flow induction is not necessary for the monitor/detector (20) to operate properly it should not be included. It should also be appreciated and understood that the active/passive flow induction (26) can be in the form of a housing or pouch or case or envelope or other material resistant to fluid among other factors as disclosed in FIGS. 8C and 11C.

The monitor/detector component (20) comprise a plurality of detectors or sensors (28). The detectors or sensors (28) can be individually replaceable or can be replaced as a unit. Replacement of the sensors may be necessary due to sensor degradation. In other situations, a user may wish to detect certain chemicals, analytes or other factors and will choose which sensors to install in the system (16). The entire monitor system (16) can be removed and replaced as a unit or at least one element or component of the monitoring system (16) can be removed and replaced. At least one component or element of the monitoring system (16) can be of a printed element or component. Such methods of printing electronics can include inkjet, silk-screen or other methods of electrophotography printing.

The sensors (28) may detect harmful or unwanted materials such as chemicals, biological material, gases, analytes or other factors associated with standards, safety and security of food/beverage/drug. Such materials can include volatile organic compounds (VOCs), hazardous air pollutants (HAPs), organophosphates, toxins, endotoxins, mycotoxins, pathogens, foodborne illness, viruses and bacteria among other factors related to food/beverage/drug. The sensors (28) could be configured for generating a signal which is indicative of the presence or level of biogenic amines such as ammonia, dimethylamine, trimethylamine, hypoxanthine, putrescine, cadaverine, dopamine and histamine. Such amines play an important role in the degradation pathways of amino acids in biological systems. For this reason, they are widely recognized as indicators of spoilage in foods/beverage/drug, particularly fish and other types of meat and seafood. Other types of sensors that can be used include colorimetric gas sensors, chemiresistor sensors, electronic noses, electronic tongues, chemical field-effect transistor, fluorescent chloride, hydrogen sulfide, nondispersive infrared, glass electrode, zinc oxide nanorod, catalytic bead or a hygrometer. Other types can include those that detect, monitor or measure enzymatic activity or macrobial or microbial activity, oxidation or external tainting.

It should be appreciated that the monitor system (16) is configured to communicate with the associated receiver (AR). That is, the monitor system (16) collects data and transmits or otherwise shares the collected data with the associated receiver (AR) for processing. The processing of the data generated by the monitor/detector (20) can also be completed on-board of the monitoring system (16). Measurement hardware known as a potentiostat is one method of on-board processing. A potentiostat is the electronic hardware required to control a three-electrode cell and run most electroanalysis. A voltammetry circuit or potentiostat comprises an electric circuit which controls the potential across the cell by sensing changes in its resistance, varying accordingly the current supplied to the system (e.g a higher resistance will result in a decreased current, while a lower resistance will result in an increased current, in order to keep the voltage constant). Other types of electronic hardware, such as a bipotentiostat and polypotentiostat can be used. A potentiostat for single working electrode can also be used. These types of electronic hardware are fundamental to electrochemical analysis related to redox chemistry and other chemical phenomena. Components and elements of poteniostats are disclosed in FIG. 4.

The associated receiver (AR) of the illustrated embodiment include a processor (30), a memory (32), a communication circuitry (34), a power source (36). The associated receiver (AR) can also include location circuitry (38) (e.g. global positioning system, assured positioning, navigation and timing or inertia/acceleration sensors among others that track location). It should be appreciated that the location tracking can be performed by other elements and components of the system (SYS), therefore location circuitry (38) should be considered an optional element or component of the associated receiver (AR). It should also be appreciated that the associated receiver (AR) can include a wide variety of additional components as is conventional. Such additional components can include a display device, input device, various sensors, various antennas, peripheral devices, etc. In some examples, the processor and memory can be on-board the sensors (S) or onboard the monitoring system (16). To this end, suitable software for analyzing the data is stored in the on-board processor and memory of the monitor/detector (20) as well as the processor (30) and memory (32) of the associated receiver (AR).

It should be appreciated that the sensor (S) and associated receiver (AR), although shown as separate components, can be provided in a common housing or single unit or single strip or single printed element if desired. In such case, the associated receiver (AR) could then transmit an alert, alarm or other signal indicative of a detected chemical, chemical concentration or other factor thereof to another associated device or associated receiver.

Software stored in memory (32) can be in the form of an application, or "app," that is downloaded from an app store or the like. The app can be provided with various resonance frequencies or "signatures" of chemicals or other factors. The signatures can be compared to the data to determine whether the chemical signature was detected by the monitoring device (16) or more broadly the sensor (S) or monitoring system (SYS). The app can be configured to be automatically updated with new signatures as the need to detect particular chemicals arise. That is, it is possible to provide new and/or additional chemical signatures for the app to check against the data to detect specific chemicals.

The app can further include features such as adjustable thresholds. For example, for some chemicals that are routinely present in certain amounts or concentrations and/or not generally considered dangerous or problematic below certain levels, the application can be configured to detect or trigger an alarm when a threshold amount is met or exceeded. For some chemicals which are considered dangerous or problematic in any amount, the thresholds would not generally be adjustable.

The app can be further configured to, once a chemical is detected, share the detection information. For example, the application can be configured to use the communication circuitry (34) to broadcast an alert (or generate a notification) via any suitable communications network (e.g., WIFI, NFC, Bluetooth, cell, radio-frequency identification, etc.). The alert may be directly sent to others, for example, the personal communication device of an asset operator, or sent to the cloud computing or a server (or through a network) and then on to devices within a range of a given location of a sensor (S) or the system (SYS). In another embodiment, a tasking software or automation element could use the data generated from the system (SYS) to initiate or assign a specific task related to the data generated from the system (SYS). In general, the objective of the system (SYS) is to create a new data standard revolving around spoilage and contamination. Such data standard will serve as the basis for decision making or action related to resources for controlling food or beverages or drugs. FIGS. 3A-3D illustrate three exemplary electrochemical sensors that can serve as a monitor/detector. FIG. 3A presents one embodiment known as microneedle (MN), which can be a type of biosensor that requires contact or interaction between a bioreagent layer or enzyme and a target analyte. This interaction produces a unique signature or resonance frequency that is transmitted rapidly in a single step. The microneedle (MN) can be invasive, minimally invasive or non-invasive. These three categorizations of microneedle (MN) are determined by whether the working electrode penetrates a food or beverage or drug or host. FIG. 3B presents another embodiment comprises of three electrodes including a working electrode, reference electrode and a counter electrode. The exemplary sensor known as a nanosensor (NS) can include a layer of particles, e.g. macro, micro-, mesa- or nano-sized particles of active carbon or porous carbon, which may be in the form of nanotubes, graphene or other type of nano-particle. The nanosensor (NS) is capable of operating in air, gas, vapor, liquid or through contact. FIG. 3C presents another embodiment similar to the embodiment presented in FIG. 3B; the difference being that the sensor is printed on a carrier material such as cellophane or other types of flexible wrapping or packaging or covering or a seal or cap. One method for producing or fabricating sensors on a carrier material that is particularly well-suited for purposes of the present disclosure is set forth in U.S. Pat. No. 8,674,827 to Hummer et al. The cellophane sensor (CS) has unique properties allowing for full functionality on a flexible carried material.

Turning to FIG. 3A(i) and FIG. 3A(ii), which present the microneedle (MN) sensor and the microneedle electrodes (ME). FIG. 3A(i) shows the microneedle (MN) consisting, in one example, of three electrodes including a counter electrode (39) a working electrode (40) and a reference electrode (41). The working electrode is used to conduct electrochemical response based on interaction between enzymes and compounds (42). For example, when detecting organophosphates, organophosphorus and organophosphorus hydrolase interact to produce a unique chemical signature/resonance frequency measured using square-wave voltammetry and wireless data transmission. Other types of voltammetry can be used, including linear sweep, staircase, square-wave, cyclic, anodic stripping, cathodic stripping, adsorptive stripping, alternating current, polarography, rotated electrode, pulse, differential pulse, stripping and chronoamperometry.

FIG. 3A(ii) presents embodiments related to the microneedle electrodes (ME). The microneedle electrodes (ME) can be hollow microneedle pillars with holes or solid microneedles with no holes. Hollow microneedles can consist in a 2×2, 3×3, 4×4, 5×5 or any number with the microneedle array (43) and can be smaller than the size of a penny. The microneedle platform (44) can have an 800 μm height, and vertical circular openings of 425 μm diameter. The platform (44) can also have other heights and openings. The openings can be packed with a substance, then polished and coated with a solution for the working and counter electrodes and filled with a substance for the reference electrode (45). The microneedles are connected with wires and conductive silver epoxy to forge electrical contact. The microneedles (MN) can be prepared using visible light dynamic mask microstereolightography and fabricated using photosensitive acrylate-based, biocompatible polymer, such that the (MN) are fully biocompatible and compliant with FDA and USDA standards, which is particularly important for food/beverage/drug applications.

FIGS. 3B(i) and 3B(ii) present yet another exemplary electrochemical sensor. FIG. 3B(i) presents a single sensor unit (SU) and FIG. 3B(ii) presents a sensor array (SA), which is multiple sensor units (SU). The single sensor unit (SU) consists, in one example, of three electrodes, including a counter electrode (46), a working electrode (47) and a reference electrode (48). The working and counter electrodes can consist of particles of active or porous carbon or nanoparticles; the reference electrode can be a silver/silver chloride electrode. The sensors can be printed on a carried material or substrate (49) (e.g. flexible, thin film, thick film or other materials based on detection objectives and operating environment, particularly temperature, humidity, moisture and pH). Printing methods can include silk-screen or ink-jet printing or other methods of electrophotography on various substrates (49) including polyester, polymeric materials, alumina, ceramic materials, glass and semi-conductive materials such as silicon, silicon oxide and other covered subetrates. The sensor unit (SU) can also include conducting pads (50) for coupling the electrodes to associated circuitry (e.g. processor, communication circuitry, power source etc.) of the monitoring device (16). A sensor with similar properties is well suited and is set forth in U.S. Pat. No. 8,629,770 to Hummer et al. and U.S. Pat. No. 7,176,793 to Hummer, both of which are incorporated herein by reference in their entireties.

Other types of monitor/detector components can also be used such as microelectrochemical systems (MEMS), nano-electromechanical systems (NEMS), electrochemical amperometric, metal oxide semiconductor, infrared sensor (nondispersive), thermal sensor (pellitor), photoionization (PID), chemiresistor, graphene, hybrid and nanostructures, Quartz Microbalance, field-effect transistor (FET), biosensors, capacitive sensors, piezoresistive sensors, photodetectors, temperature sensors, humidity sensors, gas sensors, chemical sensors among other types of sensors that can detect, monitor or measure factors related to food/beverage/drug.

FIG. 3B(ii) illustrates an exemplary sensor array (SA). The sensor array (SA) includes a plurality of individual sensor units (SU), as shown in detail in FIG. 3B(i). The sensor units (SU) that make up the sensor array (SA) can be programmed to detect the same chemical at the same concentration level; detect the same chemical at different concentration levels; detect different chemicals at the same concentration level or detect different chemicals at different concentration levels.

It should be appreciated that a sensor unit (SU) or sensor array (SA) can be individually replaceable or can be replaced as a unit. Replacement of the sensor units (SU) and/or sensor array (SA) may be necessary due to sensor degradation. In other situations, a user may wish to detect certain chemicals and will choose which sensors to install in the system.

The sensor unit (SU) may detect a wide range of chemicals or materials or gasses or biological material or analytes. In the exemplary embodiment, the sensor unit (SU) is configured to detect chemicals, compounds or analytes associated with spoilage and contamination that include biogenic amines (histamine, tryptamine, tyramine, phenylethylamine, putrescine, cadaverine, agmatine, spermidine, spermine, xanthine and ammonia).

FIGS. 3C(i) and 3C(ii) present another exemplary electrochemical sensor, the cellophane sensor (CS). FIG. 3C(i) illustrates a small sensor most suitable for detecting chemicals, analytes or other factors in food/drug/beverage that have a small surface area (CSS) and FIG. 3C(ii) illustrates a large sensor most suitable for detecting chemicals, analytes or other factors in food/drug/beverage that have a large surface area (CSL).

Both sensors, known as cellophane sensor (CS) can be in the form of a biosensor, which relies on an electrochemical interaction between the bioreagent and the target chemical or analyte. The cellophane sensor (CS) can also be in the form of a sensor unit (SU) or sensor array (SA) as disclosed in FIG. 3B, which may or may not rely on an electrochemical interaction between the bioreagent and the target chemical or analyte. As previously disclosed, the cellophane sensor (CS) is printed on or embedded in a carrier material such as cellophane or similar flexible food wrapping (51), cover, cap or seal. This sensor can be fabricated on a variety of flexible and non-flexible substrates for detection of chemicals in vapor or gas or liquid in or on surface areas. The sensor can be printed using methods such as silk-screen or ink-jet or other electrophotography methods. Printing modifications such as using stress-enduring inks on flexible electrodes can also be part of the present disclosure. The sensors can be printed in various sizes, including small, illustrated in FIG. 3C(i) and large illustrated in FIG. 3C(ii). Printing size can be determined in-part by whether the electrodes cover the surface areas of foods/beverages/drugs being monitored for chemicals. The cellophane sensors can have three electrodes: a counter electrode (46), a working electrode (47) and reference electrode (48). The cellophane sensors can also have any number of electrodes and can be printed to resemble package marking such that it is not readily apparent that the sensors are attached or embedded in packaging.

Figure 4:
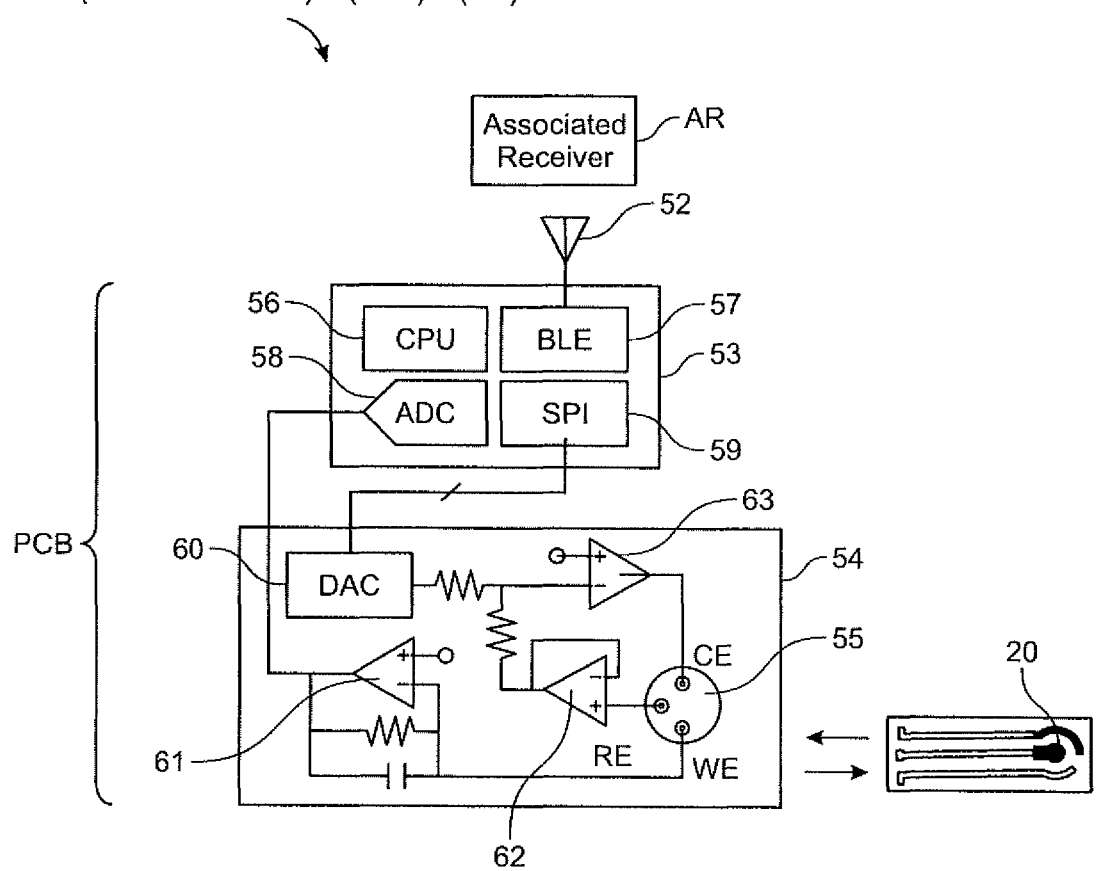
FIG. 4 is a block diagram of units, components and elements of an exemplary system in accordance with the present disclosure.

FIG. 4 presents a schematic block diagram of an exemplary system for detecting, monitoring or measuring chemicals, analytes and other factors in food/beverage/drug or the environment of food/beverage/drug throughout the supply chain (SYS). The system comprising of three major components, each of which have several sub-components or sub-elements. The first major component of the system (SYS) is the monitor/detector (20) and the second major component of the system (SYS) is a printed circuit board (PCB) and the third major component is the associated receiver (AR). Therefore, the exemplary system for detecting, monitoring or measuring chemicals, analytes and other factors in food/beverage/drug or the environment of food/beverage/drug throughout the supply chain can be known as (SYS=MONITOR/DETECTOR+PCB+AR).

The monitor/detector component can comprise of single detector or a plurality of detectors (28) that detect, monitor or measure chemicals, biological materials, analytes and other factors associated with food/beverage/drug. The detectors can be individually replaceable or can be replaced as a unit. The monitor/detector (20) is operatively coupled to the printed circuit board (PCB) through any means necessary. A connector (55) can be used to join the electrodes of the monitor/detector with the printed circuit board (PCB). Other relevant connection methods include the secure digital card (SDC) disclosed in FIG. 8B and the connector assembly (CON) disclosed in FIG. 11B.

The printed circuit board (PCB) comprises an antenna (52), a microcontroller (53) and a voltammetry circuit (54). It should be appreciated that the printed circuit board (PCB) can include a wide variety of additional components and elements as conventional and that any combination thereof can be printed on a carried material (126) as disclosed in FIG. 16B or a substrate (49) as disclosed in FIG. 19. Methods of printing can include, but are not limited to silk-screen, ink-jet or other methods of electrophotography.

The microcontroller (53) can include various sub-components or sub-elements such as a processor in the form of a central processing unit (56), communication circuitry in the form of Bluetooth low energy (57) or similar method of wireless communication, analogue to digital converter (58) and a serial peripheral interface (59). The microcontroller can be operatively coupled to the voltammetry circuit (54) through the analogue to digital converter (58) and a serial peripheral interface (59). The voltammetry circuit (54) can include sub-components and sub-elements such as: a data acquisition system (60), a potentiostatic control circuit for the working electrode (61), potentiostatic control circuit for the reference electrode (62) and a potentiostatic control circuit for the counter electrode (63). It can also be the case that the monitor/detector (20) comprises of a single working electrode, in which case there would be only a single potentiostatic control circuit for the working electrode (61).

It should be appreciated that the printed circuit board (PCB) can be developed on a polyimide substrate or similar material with flexible, yet durable properties. The circuit board can also be precision-printed (e.g. 3D printed, screen-printed or ink-jet printed) on surfaces with flexible properties such as rubber, silicone, polyurethane or some other similar material (e.g. packaging, wrapping, covers, caps, labels, stickers, seals, adhesives etc.).

The square-wave voltammetry circuit (54) can be capable of applying scanning potential square-wave voltammetry excitation waveform and is controlled by a microcontroller unit (53). The microcontroller unit (53) integrates an analogue to digital converter (58) for measuring current from the working electrode (47) and the Bluetooth low energy (57), which is connected to a small antenna chip (52) for wireless communication with a Bluetooth low energy host device or associated receiver (AR). It should also be appreciated that the printed circuit board (PCB) can also include an active/passive power source (24). Active power sources can include a battery in the form of either a photovoltaic cell or solar cell and passive sources can include an antenna (52) for receiving electromagnetic energy.

Figure 5:
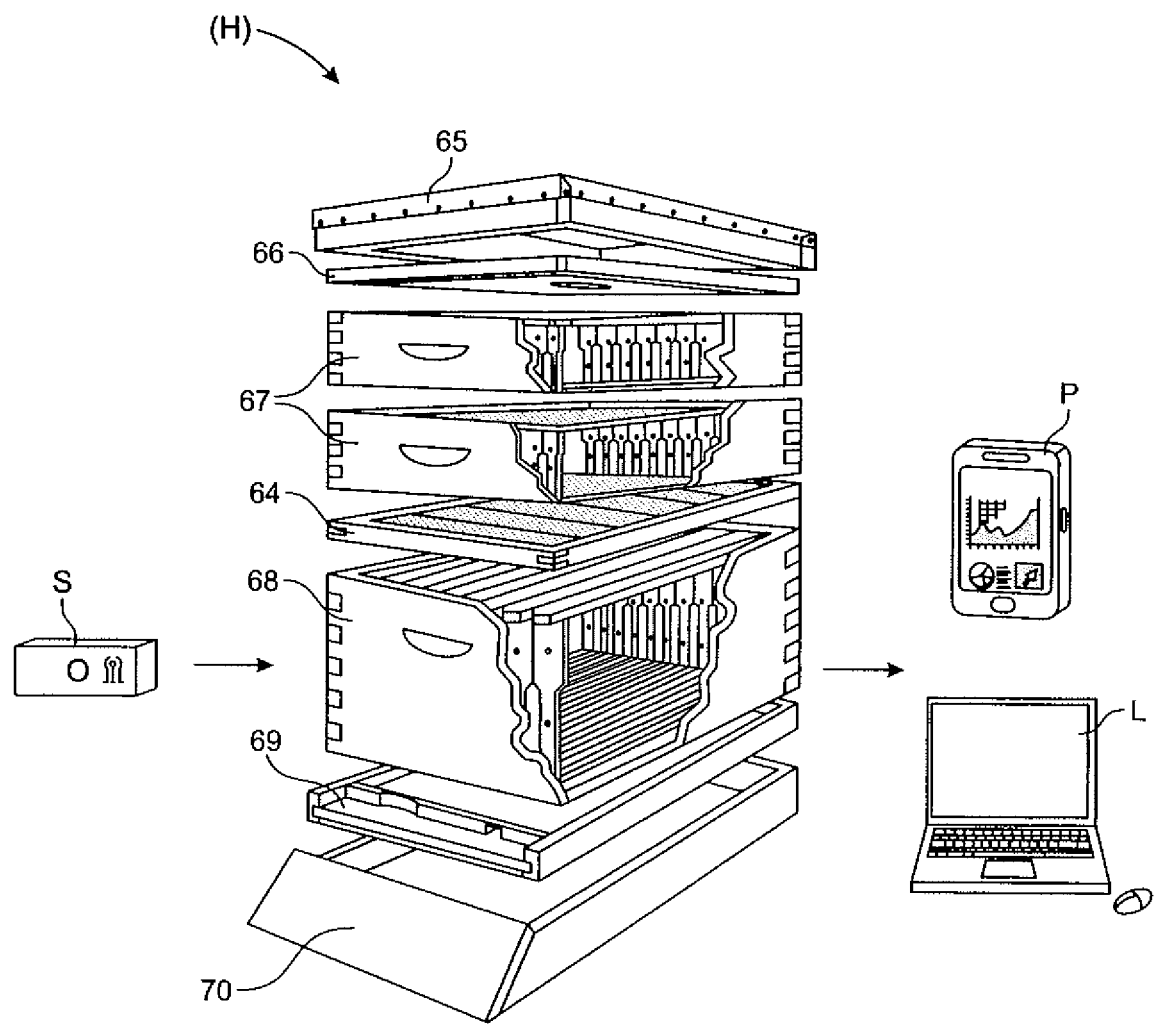
FIG. 5 is a perspective view of a portion of a system for monitoring an insect environment in the form of a beehive or bee colony.

FIG. 5 illustrates an exemplary system for detecting, monitoring or measuring chemicals, biological materials, analytes and other factors in food or the environment of food throughout the supply chain (SYS) as part of Phase (A) in the method (METH=A+B+C+D) disclosed in FIG. 1. The system (SYS) in accordance with the present disclosure is in connection with embodiments set forth in U.S. patent application Ser. No. 15/914,025 to Hummer et al., of which is incorporated herein by reference to its entireties.

FIG. 5 presents an exemplary insect environment in the form of a colony or hive (H). The hive (H) includes a sensor (S) and more broadly a system for detecting, monitoring or measuring chemicals, analytes and other factors in food or the environment of food throughout the supply chain (SYS). The sensor (S) is capable of measuring and monitoring chemicals, analytes and other factors such as: temperature, humidity, moisture, pH, light, vibration, pressure, sound, motion or insect activity within the hive (H). These factors, among others, can be correlated to an insect population and conditions in the surrounding agriculture environment. The sensor can be placed inside the hive (H) or attached to the side of the hive (H). It should be appreciated, that the placement of the sensor can vary based on the time of year, the type of chemicals being detected, monitored or measured and the state of the hive (H) In winter months, and with colonies experiencing loss, the sensors can be placed in the Queen Excluder (39). Sensors (S) can also be placed in the outer cover (65), inner cover (66), honey supers (67), deep super (68), bottom board (69) and even the stand (70). In addition to being placed inside the hive, the sensor (S) can be attached to the side of the hive, operating as a "hive-side system". The sensor (S) is configured to transmit sensed data relating to, among other things, the presence of certain chemicals or concentration levels of certain chemicals within the hive (H) to an associated receiver (AR). Exemplary types of the associated receiver (AR) are illustrated and can include a smart phone or cell phone (P) or other form of mobile communication device including laptop (L) or any other type of suitable receiver. In general, the data will be transmitted wirelessly from the sensor (S) or the system (SYS) to the one or more receivers. Wired connections can also be used.

Figure 6:
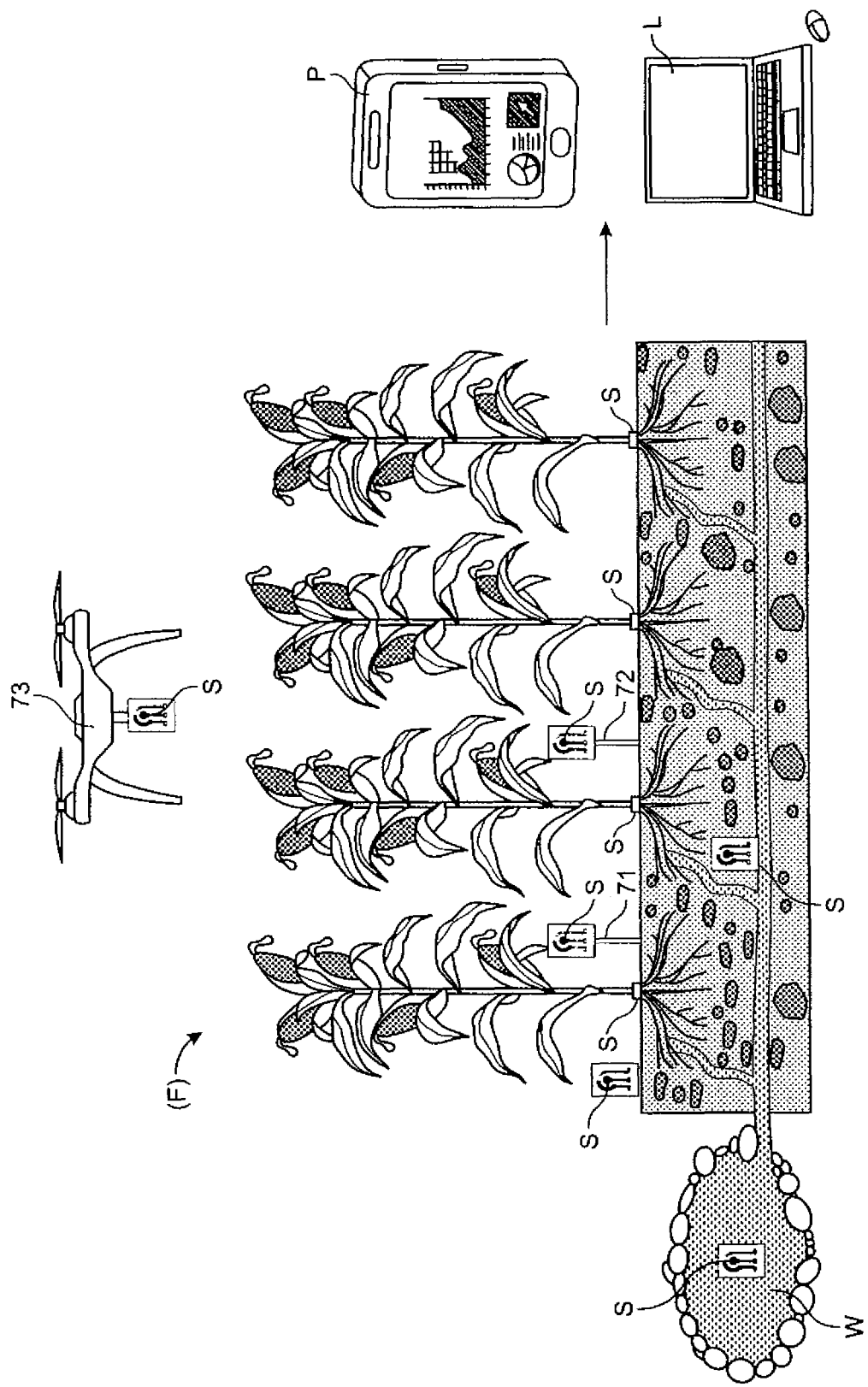
FIG. 6 is a perspective view of another portion of a system for monitoring an environment external to the beehive in the form of a crop field and its surrounding ecosystem.

FIG. 6 is an exemplary environment external to the insect environment in the form of a crop field (F). FIG. 6 presents another exemplary system and method for detecting, monitoring or measuring chemicals, analytes and other factors in food or the environment of food throughout the supply chain (SYS) as part of Phase (A) in the method (METH=A+B+C+D) disclosed in FIG. 1.

It should be appreciated to assume that bees from the hive (H) are expected to interact with the crops in the crop field (F), specifically to perform pollination of the crops. One or more sensors (S) are located in the crop field in various locations for sensing, monitoring, measuring, among other things, the presence of one or more chemicals or the concentration level of one or more chemical within the crop field (F), specifically those chemicals related to food contamination, bacteria, pathogens, toxins, pesticides, spoilage among other factors related to food production. The sensor (S) can be placed under ground or above ground. The sensor (S) can also be attached or embedded in crops themselves. The sensor (S) that operates in liquid can also be deployed in natural water sources or man-made water sources (W), including but not limited to irrigation wells, ditches, pools as well as associated flow conduits such as hoses, lines, sprinklers as well as other infrastructure, mechanisms and equipment that harness, control or store fluid. In some applications, a large network of sensors (S) can be deployed throughout the crop field (F) at various locations, including in areas where fluids are located (water wells, irrigation ditches and pools along with various types of flow conduits). The sensors can also be placed on stationary units (71) and mobile units (72) in the crop field (F). Other units can be considered, but not limited to farming equipment, irrigation infrastructure, unmanned vehicles, autonomous vehicles, remotely piloted vehicles, drones or robots (73) as well as other types of farming equipment. In the illustrated example, the sensor (S) in the hive (H) and the crop field (F) can be the same. In other embodiments, the sensor (S) can be different. The sensor (S) in the crop field (F) are configured to transmit sensed data to an associated receiver (AR) such as a smartphone/cell phone (P) or other mobile computing device like a laptop (L), or any other suitable associated receiver (AR) that can be affixed to farming infrastructure or equipment deemed "smart infrastructure" or "smart equipment". In general, the data will be transmitted wirelessly from the sensor (S) to the one or more associated receivers (AR), but wired connections are also possible. It should be appreciated that the sensor (S) in the hive (H) and in the crop field (F) can be configured to communicate with a common associated receiver (AR), such that data from all sensors (S) in the hive (H) and in the field (F) can be processed and analyzed by the common associated receiver (AR) or other devices for processing and analyzing data.

Figure 7A:
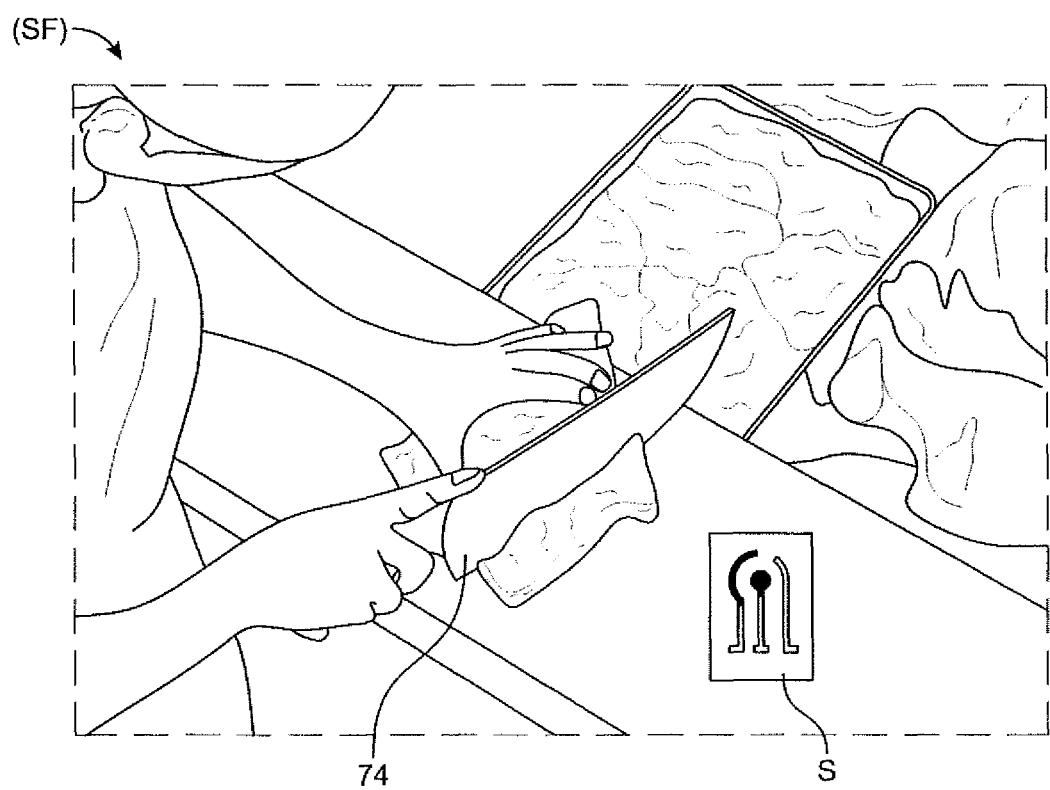
FIGS. 7A-7D illustrate exemplary sensors deployed for processing and packaging.
Figure 7B:
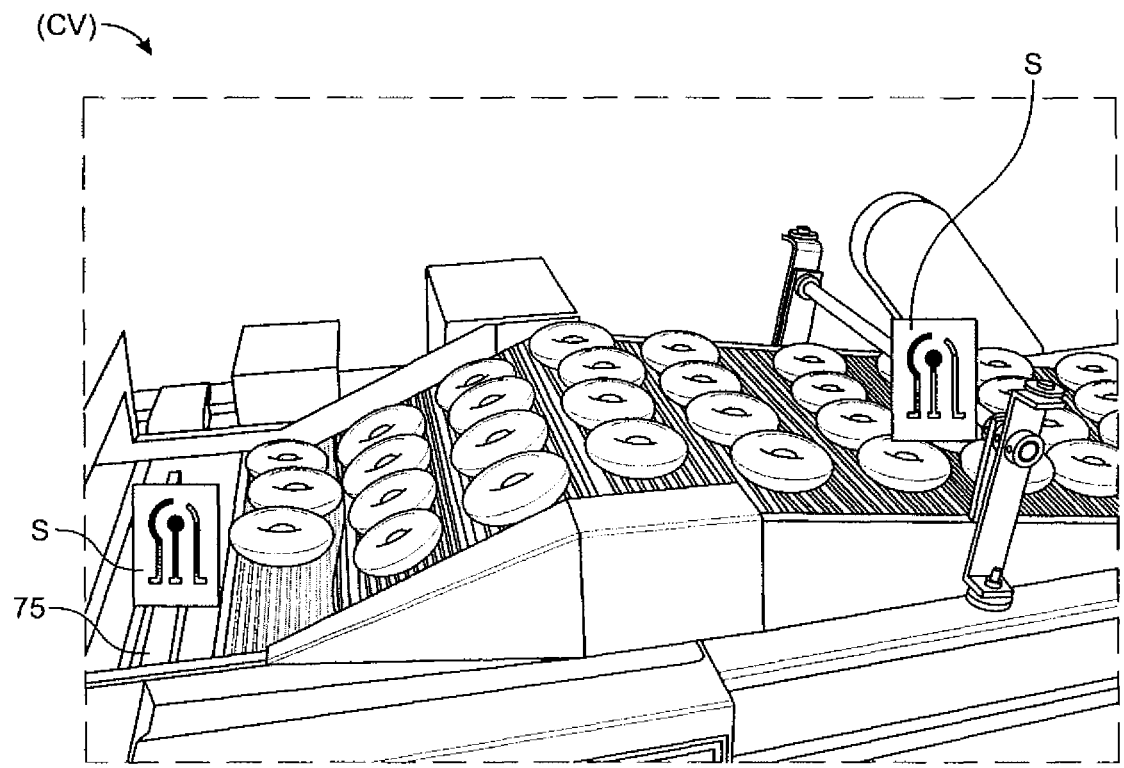
Figure 7C:
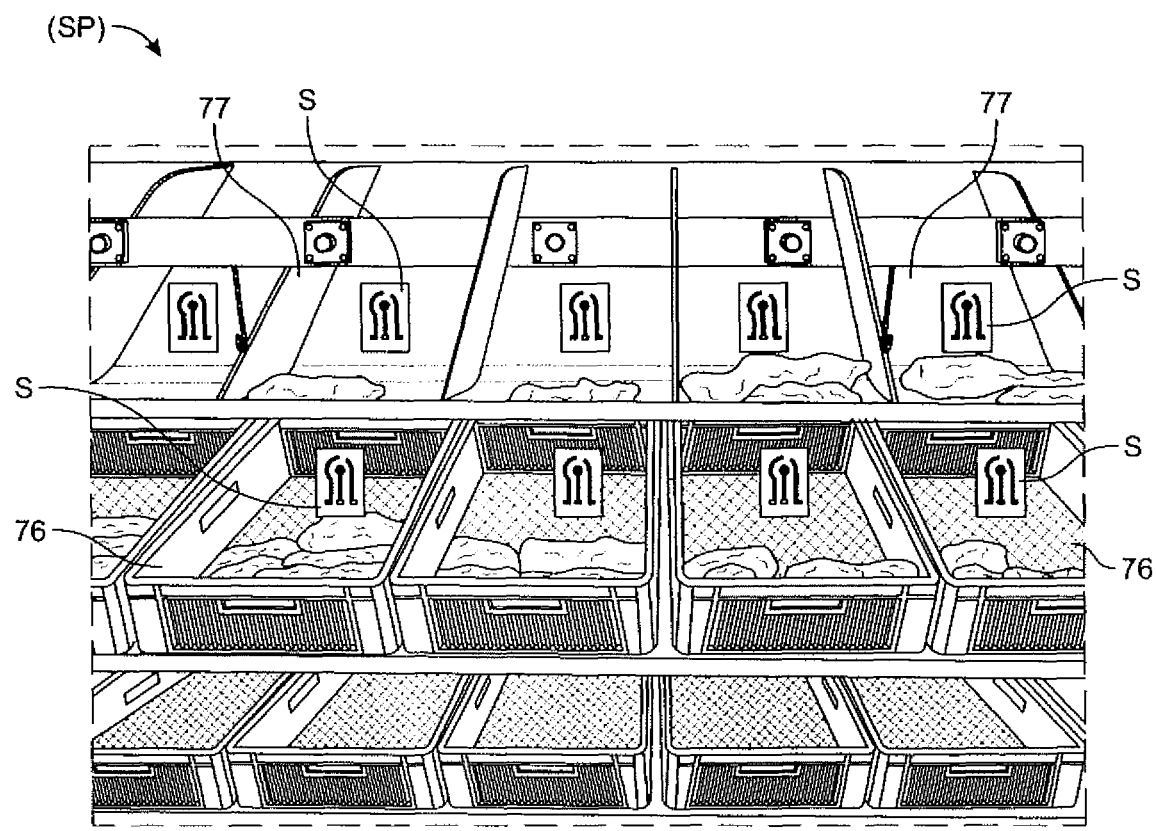
Figure 7D:
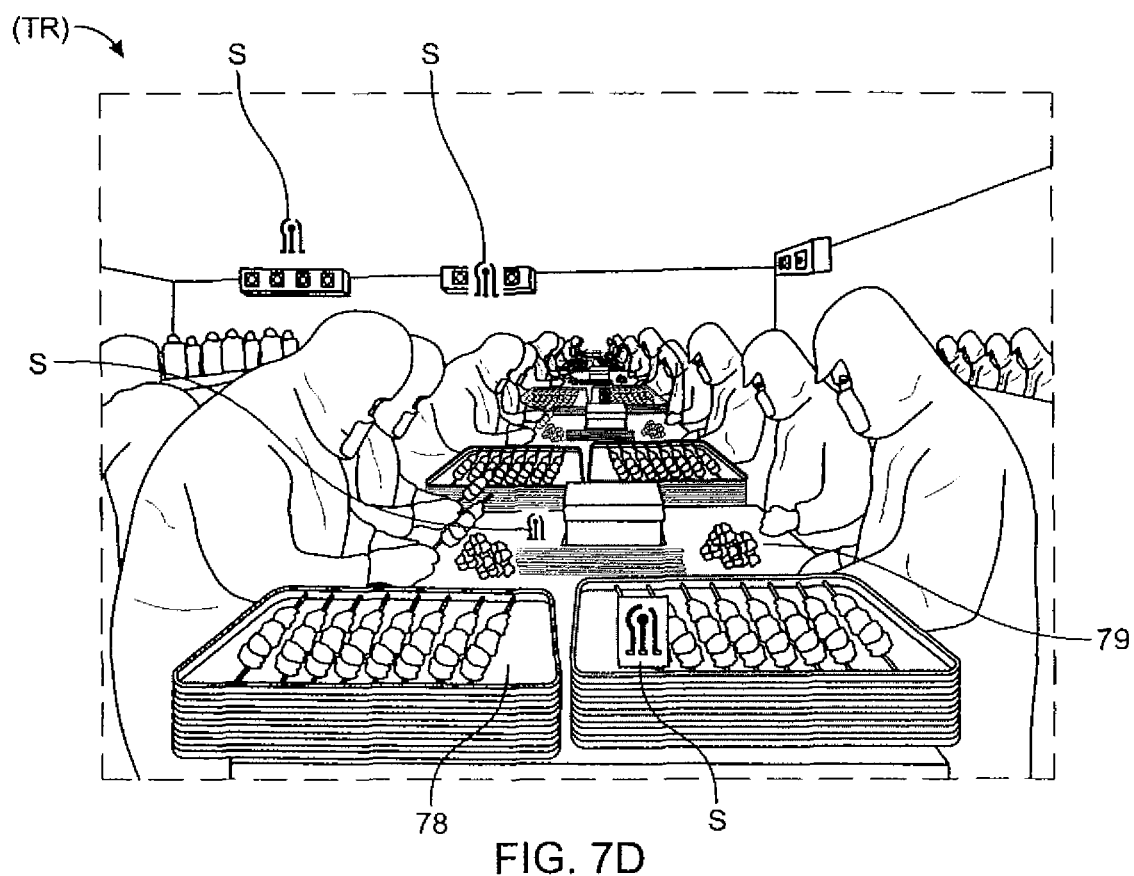

FIGS. 7A-7D provide illustrations of exemplary systems and methods for detecting, monitoring or measuring chemicals, analytes and other factors in food/beverage/drug or the environment of food/beverage/drug throughout the supply chain (SYS) as part of Phase (B) in the method (METH A+B+C+D) disclosed in FIG. 1. FIGS. 7A-7D relate primarily to surface areas that directly or indirectly come into contact with food/beverage/drug or the environment of food/beverage/drug. It should be appreciated that the disclosed embodiments can also apply to enclosed areas, semi-enclosed and open-air areas. FIG. 7A illustrates an exemplary sensor (S) on or around devices and surface areas that are involved with slicing food (SF). FIG. 7B illustrates an exemplary sensor (S) on or around devices and surface areas that are involved with transporting or moving food/beverage/drug through a process such as conveyors (CV). FIG. 7C illustrates an exemplary sensor (S) on or around devices and surface areas that are involved with sorting or separating food/beverage/drug (SP). FIG. 7D illustrates an exemplary sensor (S) on or around devices and surface areas that are involved with carrying, transporting or storing food/beverage/drug such as trays (TR). FIG. 7D also illustrates another application of the exemplary system (SYS), whereby the sensor (S) can be placed in a position whereby air or vapor or liquid flows through or in or out of a room, facility or enclosed area.

Turning to FIG. 7A, a sensor (S) is integrated into linings or covers of surface areas used in the process of slicing foods (SF). A type of sensor (S) that is particularly useful for linings or covers or caps or seals includes those disclosed in FIGS. 3C(i) and 3C(ii). The process of slicing may be manual as shown in FIG. 7A or it may also be automated. The sensors (S) can also be deployed directly to the surface areas themselves (e.g. printed directly on surface areas that directly or indirectly come into contact with food). Sensor (S) can be embedded in the device or equipment used for slicing, such that when the slicer or knife (74) touches food it is able to collect data related to the food. Such devices or equipment used for slicing include: knifes (74) as well as other sharp or dull objects used to slice or separate or probe foods. It should be appreciated and understood that the present embodiment pertains to any type of device or instrument used to slice or separate or probe food. In the process of slicing or separating or probing food, the sensor (S) collects data on chemical composition.

FIG. 7B presents exemplary sensors (S) deployed on surface areas such as tracks (75), or rollers or belts other components of conveyors (CV) that can be part of enclosed areas, semi-enclosed or surface areas used for phase (B) of the supply chain. The sensor (S) can be attached to or embedded in linings or covers or caps or lids or seals as previously disclosed. The sensors (S) can also be deployed in areas that continually come into contract with food, which allow for measurements of chemical concentrations or other factors. Other methods, including deploying optical or infrared or image (e.g. spectral, multispectral, hyperspectral etc.) sensors for detecting chemicals or other factors associated with spoilage and contamination can also be included in this embodiment. In the exemplary embodiment, sensors (S) are placed above food moving through the conveyor. As the food moves through the conveyor the image sensor (S) detect chemicals, biological material associated with food safety and security.

FIG. 7C illustrates sensors (S) being deployed in or on or around sorting bins or crates and other types of separators and processors (SP). The sensors (S) are attached or embedded to the inside of bins (76) or separators (77). The sensors (S) can also be attached to or embedded in linings or covers or caps or lids as previously disclosed. It should be appreciated and understood that various types of sensors could be used in the present embodiment. For example, gas sensors or chemical sensors can be used for enclosed areas or semi-enclosed areas or even open-air areas, while optical, infrared or image sensors can be used as well. One sensor (S) that is particularly well-suited for enclosed areas or semi-enclosed areas of the present disclosure is set forth in U.S. Pat. No. 8,629,770 to Hummer et al. and U.S. Pat. No. 7,176,793 to Hummer, both of which are incorporated herein by reference in their entireties.

FIG. 7D presents embodiments where sensors (S) are deployed in or on trays (78) or other types of surface areas or countertops (79) used to process, sort, package, transport or store food/beverage/drug, particularly in phase (B) of the supply chain (TR). The sensors (S) can also be attached to or embedded in linings or covers or caps or lids or seals as previously disclosed. For surface area or countertop (79) applications, the areas can be coated with layers of gels, liquids, and other formulas that improve function of sensors (S). The gels, liquids and other formulas also function as sterilizing agents. One fluid especially relevant to the present disclosure includes hydroxychloride or zinc chloride or hypochlorous acid (HOCL).

Sensors (S) can also be placed in-front of or on or in or behind or nearby flow vents, fans, heating, ventilation, and air conditioning systems or similar systems or equipment that harnesses, controls or moves air, vapor, liquid or other material. The sensors (S) are strategically placed to receive air flow from mechanisms that push or pull air across the sensors (S).

Figures 8A, 8B:
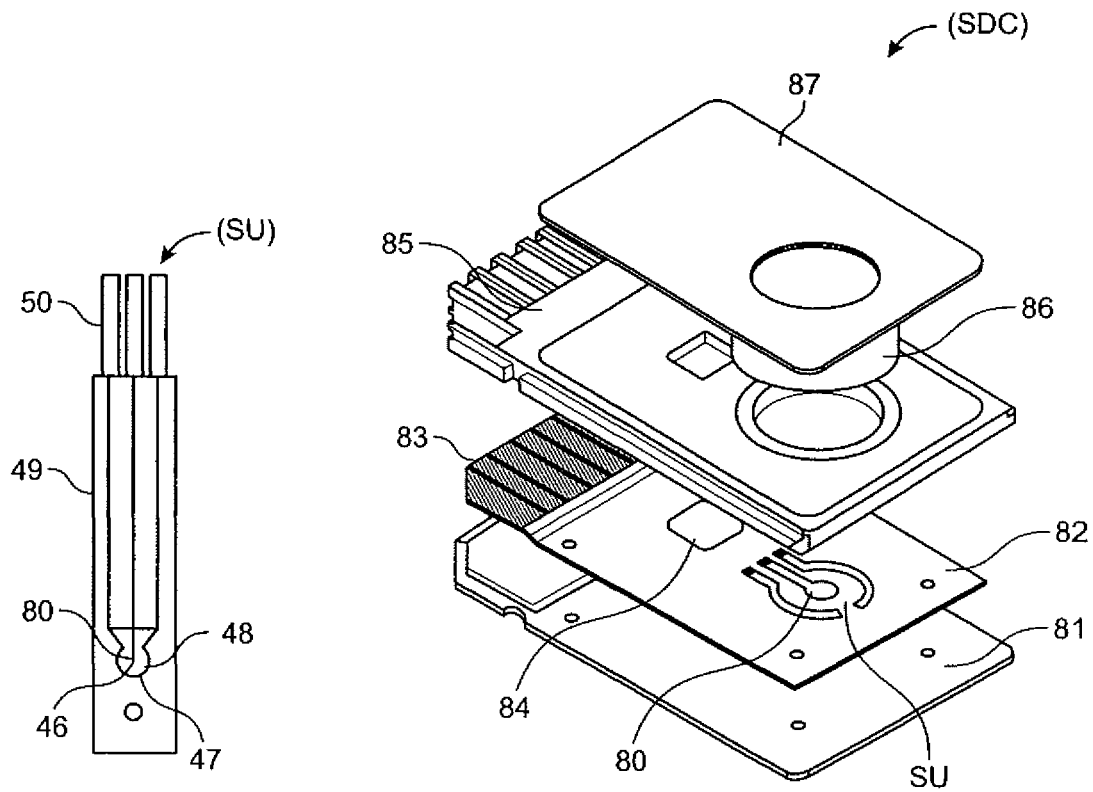
FIGS. 8A-8D present perspectives of units, components and elements for an exemplary sensor in accordance with the present disclosure.
Figures 8C, 8D:
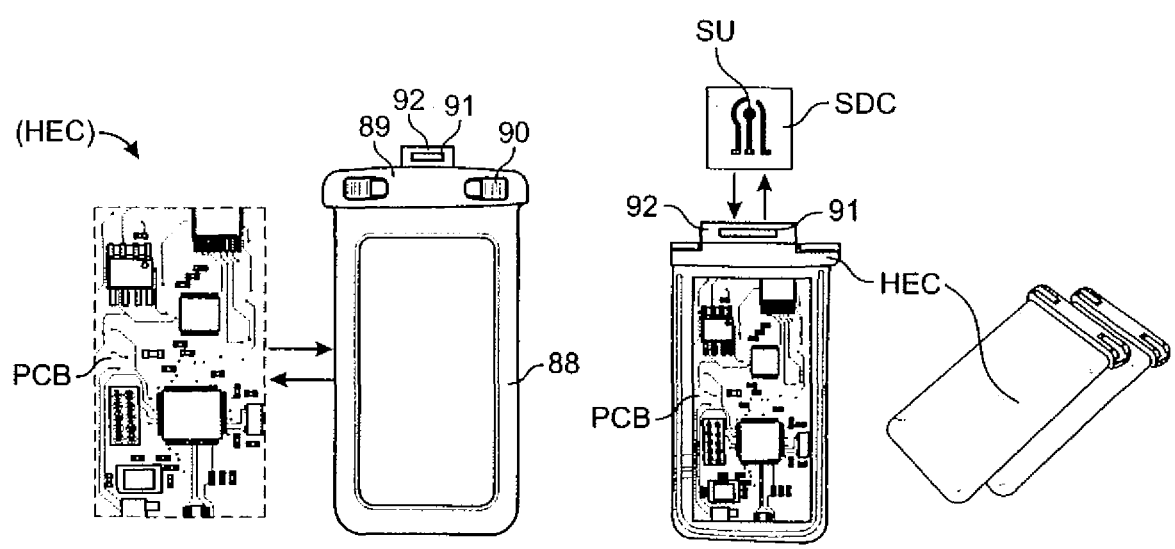

FIGS. 8A-8D present an exemplary sensor for detecting, monitoring or measuring chemicals, analytes and other factors in food or the environment of food/beverage/drug throughout the supply chain (SYS) in the method (METH=A+B+C+D) disclosed in FIG. 1. FIGS. 8A-8D present features that allow components or elements of the sensor (S) to be removed and replaced. The sensor components or elements can be replaced as a single unit or as individual units. FIG. 8A presents an exemplary sensor unit (SU) as disclosed in FIG. 3B(i). FIG. 8B presents an exemplary sensor housing module in the form of a secure digital card (SDC). FIG. 8C presents an exemplary housing for the associated sensor electronics and connectors (HEC). FIG. 8D presents all the units, components or elements of the exemplary reusable sensor device (RSD).

The sensor units (SU) can include those disclosed in FIG. 3B(i) but can also include other types of detectors including those capable of measuring temperature, humidity, moisture, pH level, Brix (e.g. glucose concentration), nutrient availability, concentration of nutrient availability and other factors relevant to food/beverage/drug. Each sensor unit (SU) includes a substrate (49) (e.g., flexible, stretchable, thin film, thick film and/or other materials appropriate for given application and chemical detection), a counter electrode (46) a working electrode (47) and a reference electrode (48). The working electrode (47) can include biocatalytic reagent layer that can be optimized for imparting the sensitivity needed for detecting low concentrations of chemicals. Conducting pads (50) are provided for coupling the electrodes to associated circuitry (e.g., processor, communication circuitry, etc.). The working electrode (47) can include an electrochemical transducer layer including a catalyst to selectively catalyze a corresponding analyte in order to cause a reaction that is detectable by the electrode assembly. For example, the transducer can include a glucose oxidase (GOx) modified Prussian Blue electrodes along with an insulating layer. The electrically conductive contacts of the electrode interface assembly are configured to electrically coupled to one or more electrical circuitry to transmit a sensor signal indicative of the reaction to detect the analyte. The electrodes of the sensors can also be covered with a gel (80) or electrolyte or hydrogel or ionic gel. The gel doubles as a fluid sampling platform and as a storage reservoir for electrochemical sensing. The sensor electrodes can be operated to perform amperometric, potentiometric or voltammetric techniques that produce an electrical signal at the sensor electrodes, e.g., associated with an electrochemical or redox reaction.

FIG. 8B illustrates an exemplary housing module for a monitor/detector in the form of secure digital card (SDC). The secure digital card (SDC) can be 3D printed or precision printed. Features of the housing secure digital card (SDC) include: various sensitivity in air, vapor, gas, liquid or through contact; easy calibration; low-power operation; easy connector interface; combined chemical detection and temperature logging; programmable logging rate and sensor traceability.

The secure digital card (SDC) has a base layer (81) that forms the outermost layer of the secure digital card (SDC). The card has a second layer (82) that contains a connector interface. The secure digital card can include up to nine pins (83) but can also include more pins if needed. The pins (83) relate to various signals including, but not limited to: SWCLK/SWDIO, nSSEL, SWCLK, MISO, MOSI, VDD, VSS and nRESET. SCLK is used to synchronize the communication between the printed circuit board (PCB) or host system and the secure digital card (SDC). Instructions addresses or data present on the MOSI pin are latched on the rising edge of the clock input, while data on the MISO pin is updated after the falling edge of the clock input. MISO is used to transfer data out from the secure digital card (SDC) into the printed circuit board (PCB) or host system. During a read cycle, data is shifted out on this pin after the falling edge of the serial clock (SCLK) when the secure data card (SDC) is selected. This signal is high impedance when the secure digital card (SDC) is not selected. MOSI is used by the (PCB) or host system to transfer data into the secure digital card (SDC). It receives instructions, addresses and data. Data is latched on the rising edge of the serial clock (SCLK) when the secure digital card (SDC) is selected. VDD can be the power supply for the secure digital card (SDC). VSS can be the signal and power ground reference for the (SDC). A low level on nRESET that puts the secure digital card (SDC) in the RESET state, whereas a high level allows for normal system operation. The signal is typically pulled or driven high and is typically not necessary for system operation as the secure digital card (SDC) automatically generates internal reset upon application of valid VDD voltage. A low level on nSSEL selects the secure digital card (SDC), while a high level deselects the module. When the device is deselected, MISO goes into the high-impedance state, allowing multiple components to share the same SPI bus. After power-up, a high-to-low transition on nSSEL is required prior to any sequence being initiated. SWCLK and SWDIO are reserved for manufacturing and calibration application. For normal system operation they should be pulled or driven high.

Several other components of the secure digital card (SDC) are included to allow the sensor to function better, including enhance sensitivity, selectivity and speed. A connector (84) allows the other components to properly fit and fasten to the cover (85) of the second layer (82), which contains the sensor (SU). Another layer (86) can cover the sensor (SU), however with a space between the second layer (82) and the other layer (86). In some instances, gel (80) can be applied to cover the sensor electrodes. The space allows flow of air or liquid or contact for the sensor to function properly. Another base cover (87) forms the other outer most layer of the secure digital card (SDC).

FIG. 8C illustrates an exemplary housing module for electronics and connectors associated with the sensor (HEC). The primary housing (88) comprising of materials resistant to factors in an environment where the sensor (S) could be deployed. Such factors can include, but are not limited to fluid, moisture, humidity, temperature, pH, corrosive chemicals, ionization, pressure, radiation, shock, stress, impact, explosion or other factors known to prompt failure in electronic or electrical components or create hazardous events. Resistant materials can include, but are not limited to composites, advanced materials, carbon fiber reinforced plastics or other types of plastics, silicones, atomically thin materials, polyurethane, rubber among other materials used to shield or protect electronic or electrical elements or components. Such materials can be biocompatible, such that the primary housing (88) can interact with biological systems, including food/beverage/drug according to FDA and USDA regulation. The primary housing (88) further comprising of a seal (89) or similar mechanism used to enclose sensor elements or components such as the printed circuit board (PCB), (e.g. communication circuitry (22) active/passive power source (24) processor (30), memory (32) or location circuitry (38) among other components of the monitoring system (SYS) so they are not damaged. In the exemplary embodiment, a printed circuit board (PCB) as disclosed in FIG. 4, is enclosed in a primary housing (88) and sealed or protected from harmful elements. The seal (89) can be set to open or closed using fasteners or loops or pins or switch-like mechanisms (90). The fasteners or switches (90) can be set to open, whereby the exemplary printed circuit board (PCB) can be removed from the primary housing (88) and reused in another primary housing (88) or reusable sensor device (RSD). The fasteners (90) can also be set to closed, whereby the exemplary circuit board (PCB) is enclosed, protected and secured in the primary housing (88) so it can be operably coupled or connected to a monitor/detector (20) via a connector (91) that can mate with a secure digital card (SDC) or connector assembly (CON).

The seal (89) can be designed so a connector (91) extends from the primary housing (88), allowing the connector (91), to mate with the secure digital card (SDC), resulting in a secure and factor resistant electrical and electronic connection between the printed circuit board (PCB) and the secure digital card (SDC) through the connector (91). It should be appreciated and understood that the connection between the secure digital card (SDC) and the printed circuit board (PCB) or other elements or components of the sensor (S) can also occur inverted from the previously disclosed fashion or inside the primary housing (88) as shown in FIG. 9B. In this embodiment, the secure digital card (SDC) is inserted into the primary housing (88) whereby the secure digital card (SDC) mates with the printed circuit board (PCB) inside of the primary housing (88). In this embodiment, a connector (91) can be used to operably couple the secure digital card (SDC) and the printed circuit board (PCB). However, it can also be the case that a connector (91) is not necessary and the secure digital card (SDC) and printed circuit board (PCB) mate directly or can be printed as a single unit.

This embodiment, like the others, ensures a secure connection between the secure digital card (SDC) and the printed circuit board (PCB) that is resistant to unwanted factors. Typically, the secure digital card (SDC) is designated the "male" connector and the connector (92) of the printed circuit board (PCB) is designated the "female" connector. In embodiments where a connector (92) is not required, the printed circuit board (PCB) is designated the "female" connector. However, the inverse can also be included in designs and features of the present embodiment. It should be appreciated that any number of housings resistant to unwanted factors can be used in the present disclosure. In the present embodiment, a secondary housing (92) resistant to unwanted factors can be used to protect the electrical or electronic connection between the secure digital card (SDC) and the printed circuit board (PCB) or other elements or components of the sensor (S).

While the foregoing embodiments illustrate an exemplary housing for a monitor/detector (20) in the form of a secure digital card (SDC) and an exemplary housing for associated sensor electronic and electrical elements or components (HEC), along with how the two housings mate to create a secure electrical and electronic connection, it should be appreciated that the secure digital card (SDC) can be connected to associated electronic elements or components, such that a housing of any type, notably one resistant to unwanted factors, enables a secure connection or operable coupling between the monitor/detector (20) or secure digital card (SDC) and other elements and components of the sensor (S), notable the printed circuit board (PCB).

With reference to FIG. 8D, the various units or components of an exemplary reusable sensor device (RSD) are illustrated. The reusable sensor device comprises of major components, a sensor unit (SU) enclosed in housing in the form of a secure digital card (SDC) and a printed circuit board (PCB) enclosed in a housing for associated sensor electronics and connectors (HEC). Each of the major components of the reusable sensor device (RSD) can be removed and replaced as individual major components. Individual elements of the major components can also be removed and replaced.

The exemplary embodiments presented in FIGS. 8A-8D have been described with reference to the preferred embodiments. Obviously, modifications and alterations will occur to others upon reading and understanding the preceding detailed description of the reusable sensor device (RSD). It is intended that the exemplary embodiment be construed as including all such modifications and alterations insofar as they come within the scope of the appended claims or the equivalents thereof.

Figure 9C:
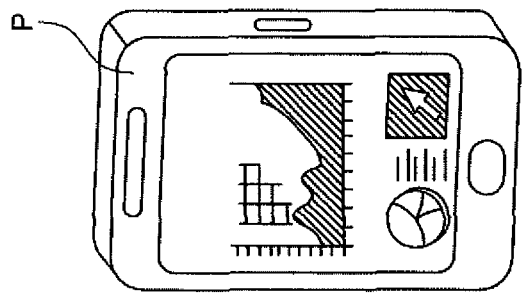
FIGS. 9A-9C present units, component or elements of an exemplary system in accordance with the present disclosure.
Figure 9B:
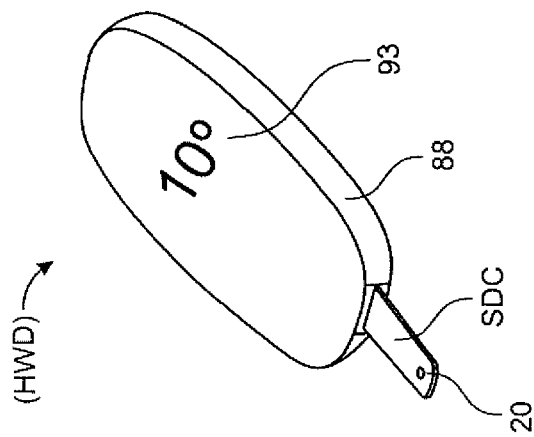
Figure 9A:
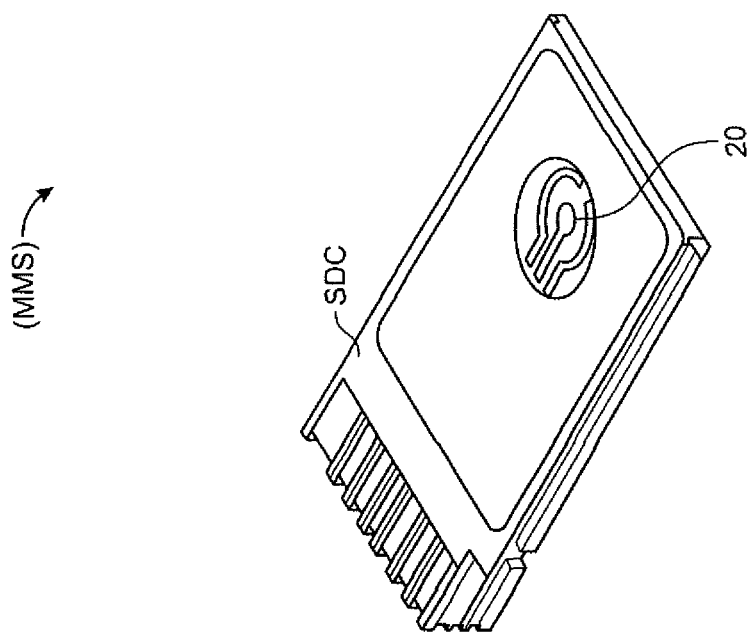

FIGS. 9A-9C provide illustrations of exemplary devices, systems and methods for detecting, monitoring or measuring chemicals, analytes and other factors in food/beverage/drug or the environment of food/beverage/drug throughout the supply chain (SYS) as part of the method (METH=A+B+C+D) disclosed in FIG. 1. FIGS. 9A-9C present an exemplary system (SYS) known as a mobile monitoring system (MMS). The mobile monitoring system (MMS) comprising of three major components, a secure digital card (SDC), a factor resistant housing with display (HWD) and an associated receiver in the form of a smartphone (P). FIG. 9A illustrates an exemplary factor-resistant housing in the form of a secure digital card (SDC). FIG. 9B illustrates an exemplary housing that is resistant to unwanted factors and has a display (HWD). FIG. 9C illustrates an exemplary associated receiver in the form of a smartphone (P).

FIG. 9A presents a factor-resistant housing for monitor/detector in the form of secure digital card (SDC). The secure digital card (SDC) comprises of a monitor/detector (20) enclosed in the various components and elements of the secure digital card (SDC) as disclosed in FIG. 8B. It should be appreciated and understood that various modifications to the present disclosure can be made in order to ensure the sensor housing is fully resistant to unwanted factors in an environment where a secure digital card (SDC) is deployed.

FIG. 9B illustrates an exemplary factor-resistant housing with a display (HWD). The housing (HWD) comprises of a monitor/detector (20) enclosed in a secure digital card (SDC), primary housing (88) and a display (93). All components of the housing with display (HWD) are highly resistant to unwanted factors that could potentially impact the operability of the mobile monitoring system (MMS). Such factors can include, but are not limited to fluid, moisture, humidity, temperature, pH, corrosive chemicals, ionization, pressure, radiation, shock, stress, impact, explosion or other factors known to prompt failure in electronic or electrical components or create hazardous events.

It should be understood that the exemplary embodiment has the secure electrical or secure electronic connection between the secure digital card (SDC) and the printed circuit board (PCB) occurring within the primary housing (88). Such that the printed circuit board (PCB) has a female connector located within the factor-resistant housing (88) and the secure digital card (SDC) has a male connector. The male connector of the secure digital card (SDC) is inserted or mated with the female connector of the printed circuit board (PCB) located within the factor-resistant housing (88). It should be appreciated that other conventional connections or any type of connections between a housing of a monitor/detector component and a housing of other components and elements of the sensor can be used.

FIG. 9C illustrates an exemplary associated receiver (AR) in the form of a smartphone (P). However, it should be appreciated that any other suitable receiver can be used, including "smart infrastructure" or "smart equipment".

Figure 10A:
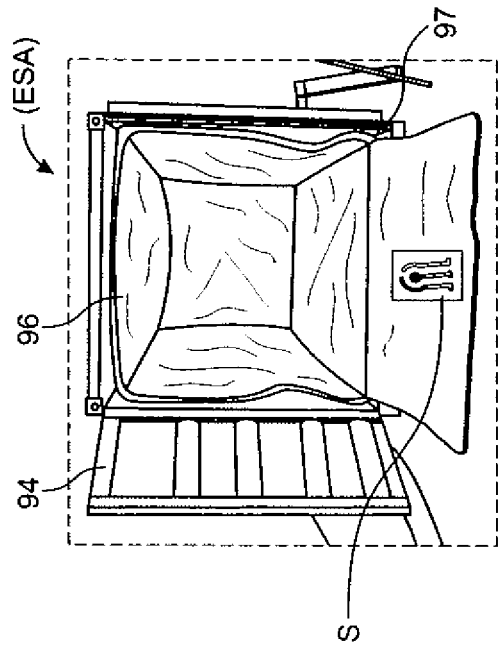
FIGS. 10A-10D illustrate exemplary deployments of sensors inside of containers.
Figure 10B:
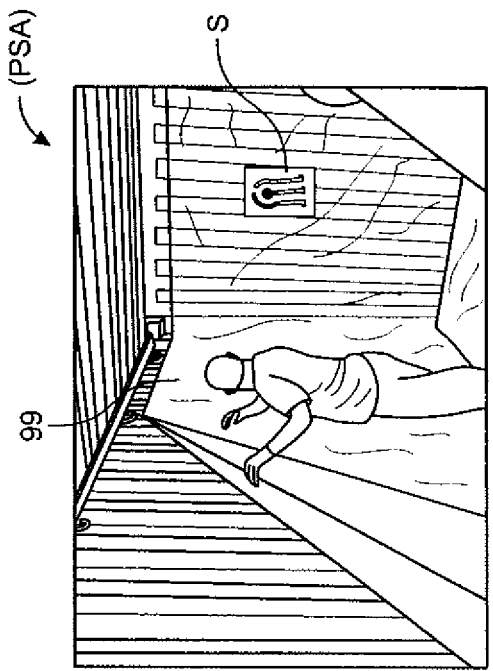
Figure 10C:
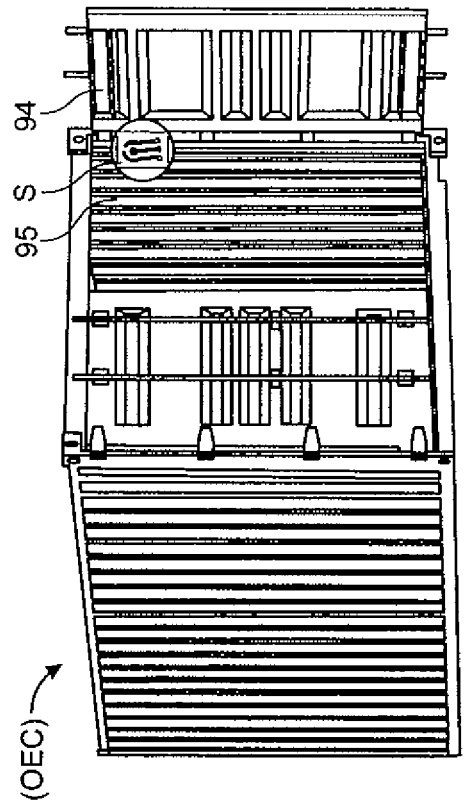
Figure 10D:
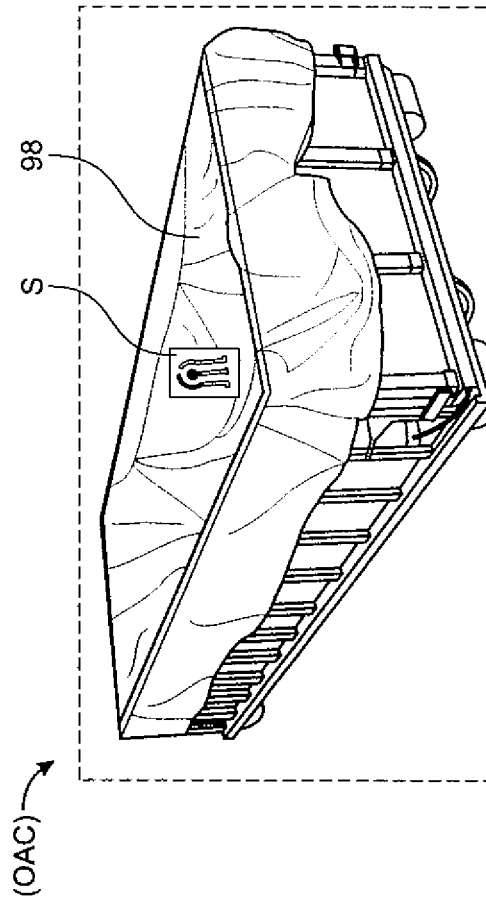

FIGS. 10A-10D provide illustrations of exemplary devices, systems and methods for detecting, monitoring or measuring chemicals, analytes and other factors in food/beverage/drug or the environment of food/beverage/drug throughout the supply chain (SYS) as part of Phase (C) in the method (METH=A+B+C+D) disclosed in FIG. 1. FIGS. 10A-10D illustrate how the sensors (S) can be applied in various forms of enclosed, semi-enclosed or open-air containers. While FIGS. 10A-10D include illustrations of cargo containers, it should be appreciated and understood that the exemplary embodiment includes containers of all types, shapes and sizes ranging from the largest containers containing may food/beverage/drug items to the smallest containers containing individual food/beverage/drug items. FIG. 10A illustrates mounting the sensor (S) near a door or other type of mechanism, component or element for opening and closing an enclosed container (OEC). FIG. 10B illustrates adhering the sensor (S) to a lining that covers the entire surface area of an enclosed container (ESA). FIG. 10C. illustrates attaching or embedding the sensor (S) to a lining of an open-air container (OAC). FIG. 10D illustrates adhering or embedding the sensor (S) to a lining that covers part of the surface area of an enclosed container (PSA).

Turning to FIG. 10A, containers, particularly cargo containers often travel by multiple modes of transportation including, by ship, air, train and truck. When packing containers, shippers and transporters have a regulatory responsibility to avoid pressure on container openings such as doors or lids or tops or covers or seals or other types of openings for enclosed containers (OEC) by leaving space, which allows air or other substance to flow. The inside of a container opening or door (94) or nearby a container opening or door (95) are among several places where the sensor (S) can be placed. At this location as well as others (ceiling, walls and floors), the sensor (S) can include an active/passive air flow induction (26). Active flow inductions can include fan concentrators, pumps etc. where air, liquid or other substance can be pushed or pulled across the monitor/detector component (20) or plurality of detectors (28). Passive flow inductions can include vents, channels, housings, pouches, envelopes etc.

One monitor/detector component (20) that is particularly well-suited for purposes of the present disclosure is set forth in U.S. Pat. No. 8,629,770 to Hummer et al. and U.S. Pat. No. 7,176,793 to Hummer, both of which are incorporated herein by reference in their entireties. Other types of components, methods and systems for sensors (S) in containers can also be used in accordance with the present disclosure. Methods for affixing the sensors (S) for the present disclosure is set forth in U.S. Pat. No. 7,911,336 to Hummer, U.S. Pat. No. 8,674,827 to Hummer and U.S. Pat. No. 7,667,593 to Hummer. U.S. Pat. No. 7,911,336, all of which are incorporated herein by reference in their entireties.

FIG. 10B presents embodiments for attaching or embedding a monitoring system (16) or sensor (S) or system (SYS) to the linings of containers, particularly linings that cover the entire surface area of a container (ESA). It should be appreciated and understood that linings that cover the entire surface area of a container (96) are similar in function and properties to bags and should be included in the present embodiment. The linings or bags (96) equipped with sensor (S) can have openings that are entirely sealable or partially sealable or not sealable. The linings or bags (96) can be sealed with fasteners, hooks, loops, zippers, tabs, ties, clips, clamps, strings, draw strings among other types of mechanisms, components or elements that entirely seal or partially seal a bag (97).

The linings or bags (96) can be reusable and washable (e.g. hand wash or machine wash), as such the sensors (S) can be appropriately embedded or attached to bags made of plastic, fabric or other material suitable for reuse. The sensor (S) can also be placed inside the lining or bag (96), whereby the sensor (S) is not attached to the lining or bag (96). Components and elements of the sensor (S) can be removed before washing or they can be made so that the components or elements do not have to be removed during washing. The present embodiment is particularly relevant to disposable plastic bags used in grocery stores to gather produce. Replacing such disposable bags with reusable/washable bags that have sensors (S) can improve sustainability and lower environmental impact. Placement of the sensors (S) can consider at least two factors including optimal functionality of the monitor/detector (20) and full functionality of transmission of data through communication circuitry (22).

FIG. 10C presents another embodiment in which a monitoring system (16) or sensor (S) or system (SYS) is attached to or embedded in linings or covers (98) of an open-air container (OAC) or semi-enclosed container. Given the open-air nature of the application, the sensor (S) can include an active/passive flow induction (26) for directing air, vapor, liquid or other substance to the monitor/detector (20).

FIG. 10D presents another embodiment in which a lining or other type of wrapping or covering (99) partially covers a surface area of the container (PSA). The portion of a container that is covered can include any part of a container including but not limited to: only the base or the base and one wall or the base and two walls or the base and all walls or one wall or two walls etc.

FIGS. 10A-10D present exemplary embodiments of deploying a monitoring system (16) or sensor (S) or systems (SYS) inside enclosed, partially-enclosed and open-air containers. The FIGS. 10A-10D also present exemplary embodiments for attaching or embedding a monitoring system (16) or sensor (S) or systems (SYS) in coatings or linings or seals of containers. The embodiments also present methods of attaching or embedding a monitoring system (16) or sensor (S) or systems (SYS) to walls or sides of containers. The exemplary embodiments have been described with reference to the preferred embodiments. Obviously, modifications and alterations will occur to others upon reading and understanding the preceding detailed description. It is intended that the exemplary embodiment be construed as including all such modifications and alterations insofar as they come within the scope of the appended claims or the equivalents thereof.

Figure 11A:
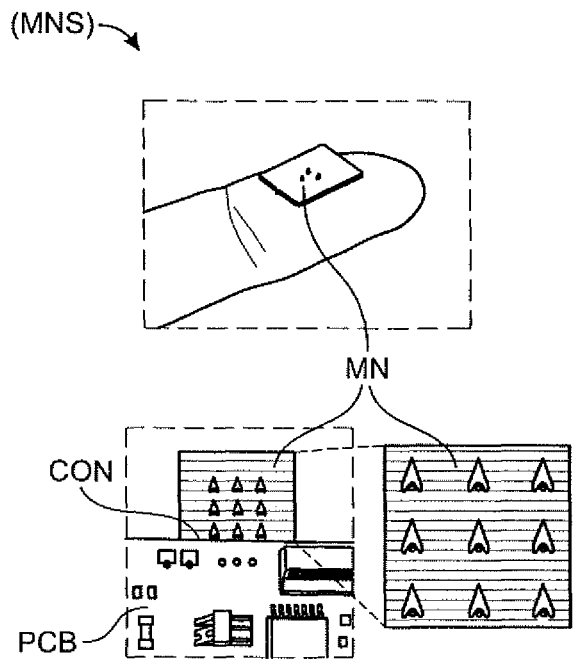
FIGS. 11A-11D present perspectives of units, components and elements for an exemplary sensor in accordance with the present disclosure.
Figure 11B:
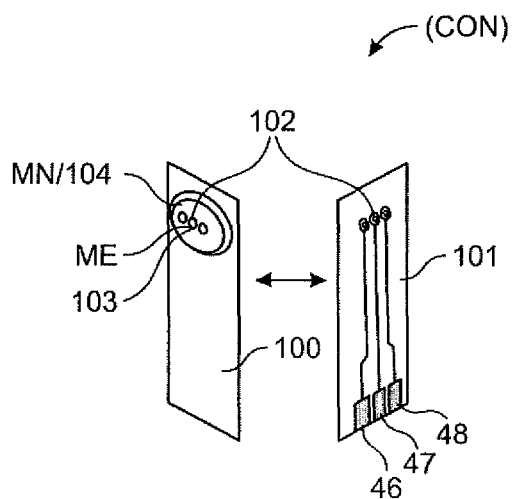
Figure 11C:
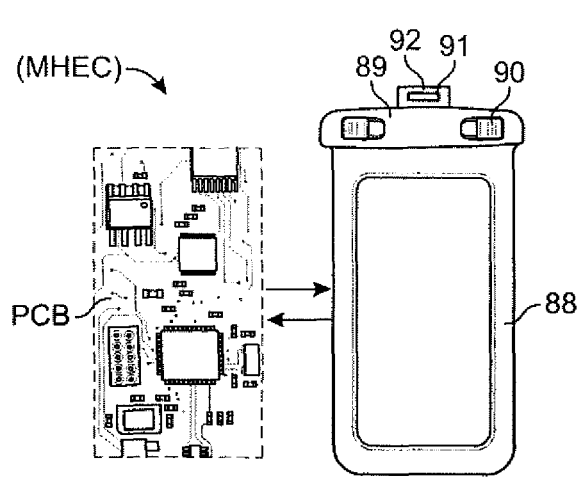
Figure 11D:
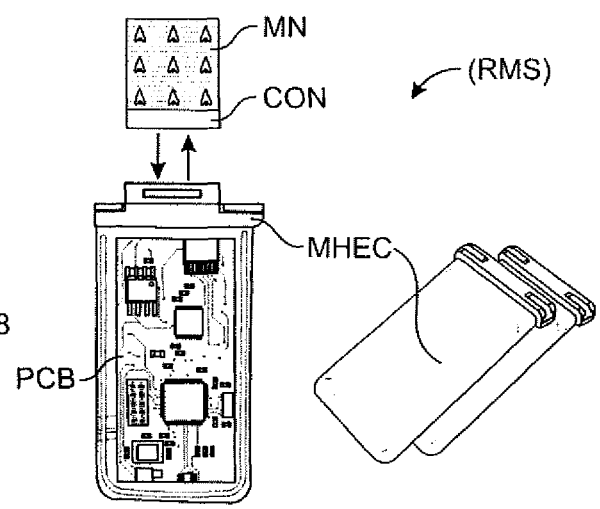

FIGS. 11A-11D provide illustrations of exemplary devices, systems and methods for detecting, monitoring or measuring chemicals, analytes and other factors in food or the environment of food/beverage/drug throughout the supply chain (SYS) as part of Phase (C) in the method (METH=A+B+C+D) disclosed in FIG. 1. FIG. 11A illustrates an exemplary microneedle sensor (MNS), whereby the monitor/detector (20) is in the form of a microneedle (MN), which is joined to a printed circuit board (PCB) through a connector assembly (CON). FIG. 11B presents an exemplary connector assembly (CON) used to join a monitor/detector (20) with other elements and components of the sensor (S). FIG. 11C presents a modified factor-resistant housing for electronics and connectors (MHEC). FIG. 11D presents all the units, components and elements of the exemplary microneedle sensor device that can be reusable (RMS).

FIG. 11A presents an exemplary sensor known as the microneedle sensor (MNS), whereby the monitor/detector (20) is in the form of a microneedle (MN) as disclosed in FIG. 3A. It should be appreciated that other types of monitor/detector (20) could be used, particularly those disclosed in FIGS. 3A-3C. The microneedle (MN) is operatively coupled to at least one of an active/passive power source (24) or communication circuitry (22) or other components or elements of the sensor (S) disclosed in FIG. 2 or the printed circuit board (PCB) disclosed in FIG. 4. It should be appreciated that the active/passive power source (24) and communication circuitry (22) can be of printed elements and be part of the monitor/detector (20). The connector assembly (CON) is also of a printed element and can be printed as part of the monitor/detector component (20).

A flexible connector assembly (CON) can be used to relieve pressure in the connection between the microneedle (MN) and the printed circuit board (PCB). The illustrated embodiment is an array of nine electrodes (e.g. counter electrode (39) a working electrode (40) and a reference electrode (41)) or three electrodes for each detector (28), which means there is a total of three detectors (28). The detectors (28) can be programmed to detect, monitor or measure the same chemical, analyte or other factor or programmed to detect, monitor or measure different chemicals, analytes or other factors. It should be appreciated that any number of detectors (28) can be part of a sensor array or any number of electrodes can make up a detector (28).

FIG. 11B presents an exemplary connector assembly (CON) that joins the microneedle (MN) or various other types of monitor/detectors (20) with other elements or components of the monitoring system (16) or sensor (S), primarily the active/passive power source (24) and communication circuitry (22). In this particular embodiment, the connector assembly (CON) operatively couples or joins the microneedle electrodes (ME) with elements or components of the printed circuit board (PCB). The components, the microneedle (MN), connector assembly (CON) and the printed circuit board (PCB) makeup the microneedle sensor (MNS).

The connector assembly (CON) comprises joining a substrate (100) or base-layer with a printed electronic element (101). The printed electronic element (101) or printed electrodes (e.g. counter electrode (46), a working electrode (47) and a reference electrode (48)) can be produced using any type of precision printing, additive manufacturing method, notably metallic ink-jet, silk-screen or other electrophotography methods. The printed electrodes (101) are joined with the microneedle electrodes (ME) through the electrode connector holes (102). The connection between the microneedle electrodes (ME) and the printed electronic element (101) is secured using a silver-loaded epoxy (103) or other forms of conductive adhesives, which can have biocompatible properties. The adhesive or silver-loaded epoxy (103) fills the electrode connector holes (102) ensuring that the microneedle electrodes (ME) are securely through the electrode connector holes (102) and properly joined or operatively coupled to the printed electronic element (101). The printed electronic element (101) consisting, in one example, of various electrodes (e.g. counter electrode (46), a working electrode (47) and a reference electrode (48)) connects to other components of the monitoring system (16) or printed circuit board (PCB), primarily the active/passive power source (24) and communication circuitry (22).

A modification to the connector assembly (CON) intended to improve the connection between the microneedle electrodes (ME) and the printed element (101) through the connector holes (102) can include adding additional conductive adhesive or silver-loaded epoxy (104) to the back of the microneedle (MN). In the present embodiment, the microneedle (MN) can actually be made of various conductive adhesives or silver-loaded epoxy (103), which can have biocompatible properties. The microneedle (MN) made of conductive adhesives can expand, mold or conform to securely fit within the electrode connector holes (102), making a more secure connection between the microneedle electrodes (ME) and the electronic printed element (101). Furthermore, the connection between the microneedle electrodes (ME) and the electronic printed element (101) through the connector hole (102) is critical because it allows continuous transmission of power and data to flow from a microneedle electrode (ME) or various other types of monitor/detector (20) to the other components of the monitoring system (16) or printed circuit board (PCB), primarily the active passive power source (24), communication circuitry (22), antenna (52), microcontroller unit (53) and voltammetry circuit (54). It should be appreciated that other modifications aimed at improving the connection between the microneedle electrodes (ME) and the printed element (101) through the connector holes (102) can be made and should be considered within scope of the present embodiment.

FIG. 11C presents modifications to the factor-resistant housing for electronics and connectors (MHEC) disclosed in FIG. 8C. The modifications are intended to protect the microneedle sensor (MNS) and its components, particularly the printed circuit board (PCB) and the connector assembly (CON) from unwanted factors such as fluid, moisture, humidity, temperature, pH, corrosive chemicals, ionization, pressure, radiation, shock, stress, impact, explosion etc. The disclosed features of the modified housing for electronics and connectors (MHEC) include coatings such as adhesives, rubber mesh, gaskets among other materials that can be approved by the International Electrotechnical Commission (IEC) to be resistant to fluid, dirt, dust among other unwanted factors. Other types of related coatings can include those with hydrophobic properties or nano properties or both. Such coatings can be applied to the primary housing (88) or secondary housing (92) or directly to the printed circuit board (PCB) as well as other units, components or elements of the sensor (S) or system (SYS). In instances where all components or elements of the sensor (S) are precision-printed the coatings can be applied to the entire sensor (S) except for the area of the monitor/detector used for detection (139), wherein air, fluid or other substance is required to interact with components or elements the monitor/detector (20).

Other features of the modified housing (MHEC) can also include padding or other suitable material, which provides further protection from the environment, particularly shock or pressure. The case or housing (MHEC) can be removable and/or replaceable. The case or housing (MHEC) can also have features allowing it to be easily cleaned, refurbished and reused. The case or housing (MHEC) can also be of a printed element or component, which allows for single-use or multiple use.

It should be appreciated that modifications to the case or housing can be made for improving operability of the microneedle sensor (MNS) or other monitor/detector (20) by protecting its components from unwanted elements or conditions such as moisture, humidity, temperature, pH, explosion among other operating environment conditions. It should also be appreciated that further modifications to not only the case or housing, but all the other components of the microneedle sensor (MNS) can be made for lowering costs or making more durable in order to withstand reuse.

With reference to FIG. 11D, the various units, components or elements of an exemplary microneedle sensor that can be reusable (RMS) are illustrated. The reusable sensor device comprises major components, a microneedle sensor (MN) enclosed in a protective housing in the form of a connector assembly (CON) and a printed circuit board (PCB) enclosed in a protective housing for associated electronics and connectors modified for further resistance from unwanted factors (MHEC). Each of the major components of the microneedle sensor that can be reusable (RMS) can be removed and replaced as individual major components. Individual elements of the major components can also be removed and replaced.

Figure 12B:
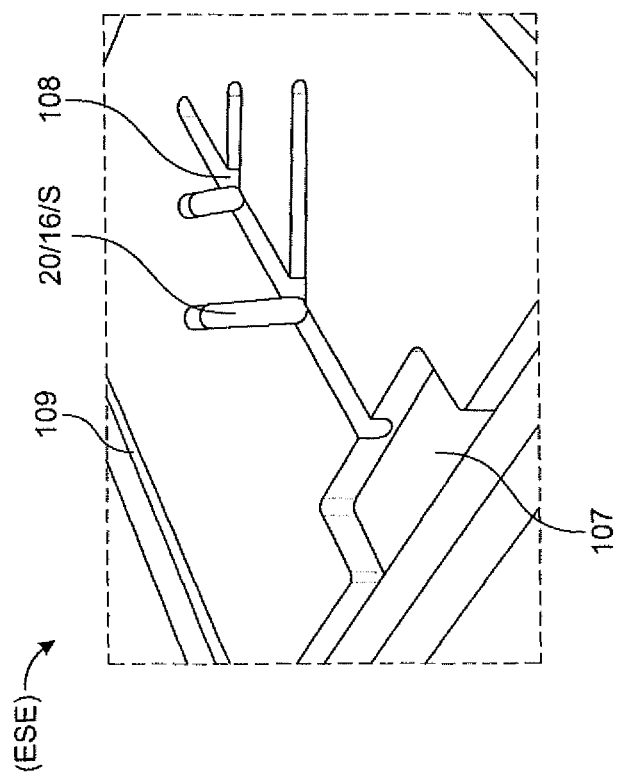
FIGS. 12A-12B illustrate exemplary deployments of sensors inside of boxes.
Figure 12A:
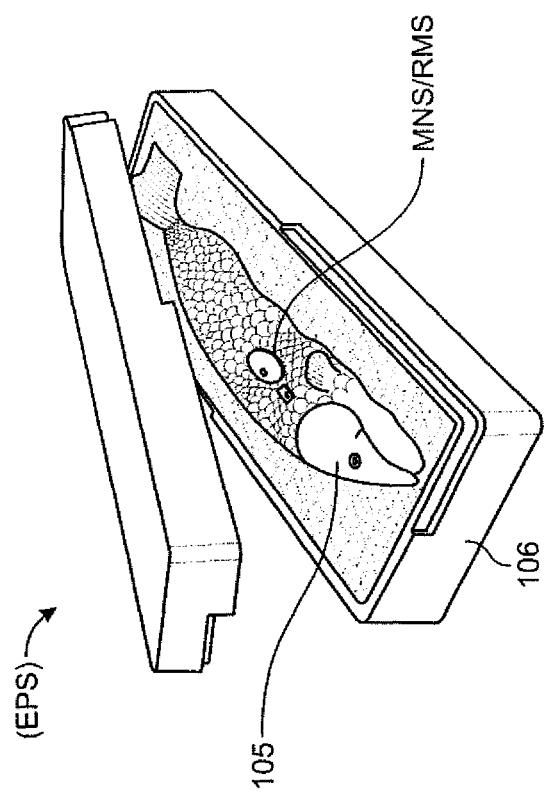

FIGS. 12A-12B provide illustrations of exemplary devices, systems and methods for detecting, monitoring or measuring chemicals, analytes and other factors in food/beverage/drug or the environment of food/beverage/drug throughout the supply chain (SYS) as part of Phase (C) in the method (METH=A+B+C+D) disclosed in FIG. 1. FIG. 12A illustrates an exemplary application of the microneedle sensor in a box (EPS). FIG. 12B illustrates an exemplary embodiment, whereby sensors (S) and electronics are embedded in or attached to the box (ESE).

FIG. 12A illustrates an exemplary application for the microneedle sensor (MNS) or reusable microneedle sensor (RMS) on a whole fish (105) in a box (106). It should be appreciated that a sensor (S) can be deployed on other foods, particularly seafood, meat, poultry and produce. The microneedle sensors (MNS) or reusable microneedle sensor (RMS) detects, monitors and measures the presence and levels of various chemicals, analytes and other factors related to spoilage and contamination. Temperature, moisture, humidity, pH, nutrient availability and location are among the other factors that the microneedle sensor (MNS) is capable of monitoring and measuring. The microneedle sensor (MNS) can be placed at any location on the fish (105)

inside of the box (106). Sensors (S) can also be placed apart from the fish (105) inside the box (106), whereby the sensor (S) is attached or embedded to a carried material (126) inside the box (106) or attached or embedded in part of the box (106).

It should be appreciated that modifications to the way the microneedle sensor (MNS) or reusable microneedle sensor (RMS) is applied to the fish (105) or host can be made. For example, the microneedle sensor (MNS) ability to function optimally is highly dependent on continuous contact between fluid or substance from the fish and the microneedle electrodes (ME) disclosed in FIG. 3A(ii). The microneedle sensor (MNS) can be designed to be invasive (e.g. deeply penetrate the fish by more than 1 millimeter) or minimally invasive (e.g. penetrate the fish by 1 millimeter or less) or non-invasive (e.g. not penetrate the fish). Various types of adhesives, glues, pastes or pins or clamps can be used to hold the microneedle sensor (MNS) in place. Other considerations in this exemplary embodiment is fabricating the microneedle sensor (MNS) of biocompatible materials as these materials pose lower health risk and are approved by the U.S. Food and Drug Administration (FDA).

The microneedle (MN) can be capable of detecting hypoxanthine, uric acid among other chemicals, analytes or biogenic amines. A particular exemplary embodiment includes a hypoxanthine sensor that can be prepared from xanthine oxidase immobilized by covalent binding on a Prussian Blue modified electrode among other approaches disclosed in this embodiment. Other methods can include assembling nickel nanosheets as hollow spheres synthesized by a facile precipitation method using silicon dioxide spheres as hard template, and the iron can be doped into Nickel (II) oxide to improve sensing of triethylamine.

These exemplary sensing methods along with others accommodate for the environment within the boxes, which often range in temperature of between 4 c and 10 c and a relative humidity range of 30 to 100 percent while in cold storage. The conditions are maintained using cooling equipment such as ice, cold packs, dry ice, fluid and other forms of temperature cooling agents. Due to the environment, special features exist to protect the sensor (S), particularly the electronics and other components from getting wet or damaged from the environment.

FIG. 12B illustrates an exemplary box that leverages operating conditions such as high levels or moisture or humidity using sensors and electronics embedded in or attached to the box (ESE). The exemplary embodiment includes embedding units or components or elements of the monitoring system (16) or sensor (S) or system (SYS) in a side, top or lid or bottom of box (ESE), Additional embedded or attached components or elements could include an active/passive flow induction (26), primarily for ensuring liquid or other flowable material reaches the monitor/detector (20) for rapid measuring and monitoring. Parts of the box (ESE) can have areas cut out (107) for units or components or elements of the sensor (S) or system (SYS), primarily electronics or printed circuit board (PCB). The box (ESE) can also have channels or flow conduits (108) where fluid or other flowable substance collects for rapid detection and measurement by monitor/detector (20) or more broadly the sensor (S). Active/passive flow induction devices or components (26) can be placed in the channel or conduits in order to aid the monitor/detector (20). The channels or flow conduits can span the perimeter of the box (109) or the channels or conduits can make a tree-like figure (108) at the base of the box such that a maximum or desired area is covered by channels and conduits (108).

In this exemplary embodiment, the monitor/detector (20) or more broadly the sensor (S) can be placed in the channels or flow conduits and can be powered by battery (lithium or other including solar cell) among other sources including antenna or other type of active/passive power source (24). In addition to traditional power sources, the sensors (S) placed in the channels could be connected using wires that connect back to the active/passive power source (24) and communication circuitry (22) of a monitoring system (16) or printed circuit board (PCB) located in the cut out areas (107). Other features of the present embodiment include an area where elements and components of the monitoring system (16) or sensor (S), including a printed circuit board (PCB) can be embedded in the box. Similar to previous disclosures in FIG. 11C, a modified housing or pouch (MHEC) can be used to protect all elements and components of the of the monitoring system (16) or sensors (S) from unwanted factors such as fluid, moisture, humidity, temperature, pH, corrosive chemicals, ionization, pressure, radiation, shock, stress, impact, explosion etc.

The exemplary embodiments have been described with reference to the preferred embodiments of deploying sensors (S) inside of boxes that are used to transport, store, display and sell food/beverage/drug. It can be expected that conditions such as temperature, moisture, humidity, pH, location etc. . . . within the boxes can vary, prompting alterations. Obviously, modifications and alterations will occur to others upon reading and understanding the preceding detailed description. It is intended that the exemplary embodiment be construed as including all such modifications and alterations insofar as they come within the scope of the appended claims or the equivalents thereof.

Figure 13A:
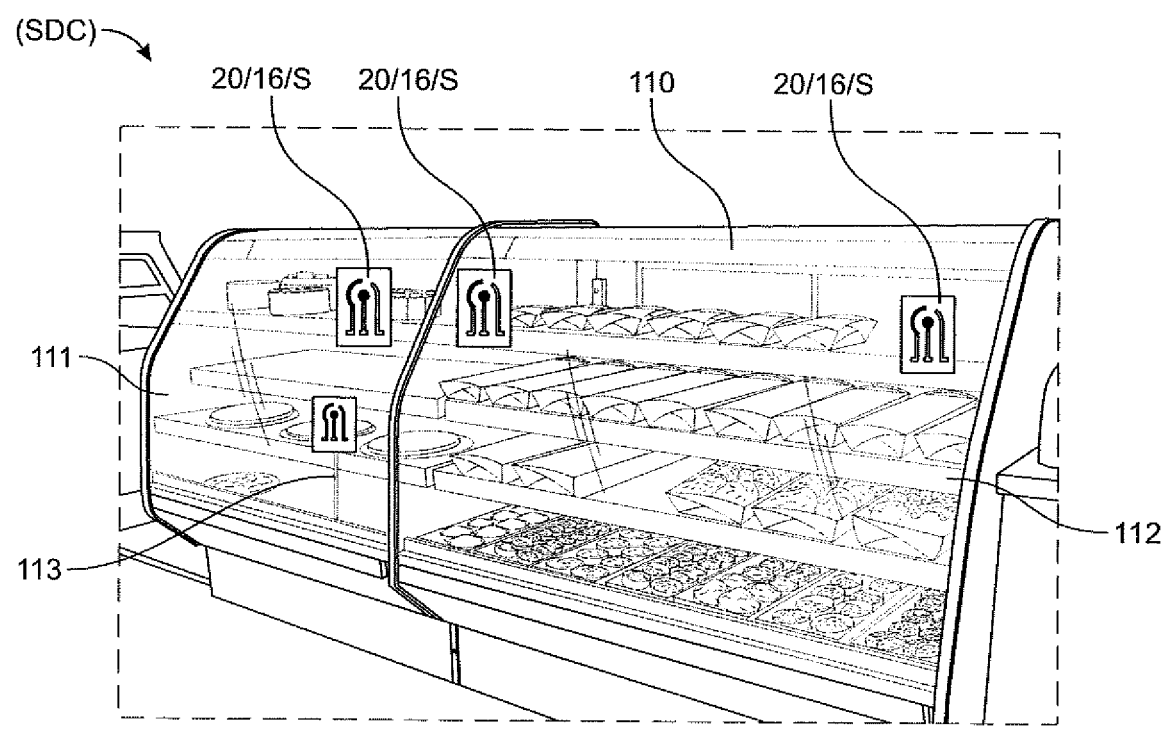
FIGS. 13A-13B illustrate exemplary deployments of sensors for enclosed areas in accordance with the present disclosure.

FIGS. 13A-15D provide illustrations of exemplary devices, systems and methods for detecting, monitoring or measuring chemicals, analytes and other factors in food/beverage/drug or the environment of food/beverage/drug throughout the supply chain (SYS) as part of Phase (D) in the method (METH=A+B+C+D) disclosed in FIG. 1. FIGS. 13A-13B present applications for enclosed areas or cases that can be open and closed with mechanisms or components such as doors, lids, latches, covers, caps, seals etc. The enclosed areas can be temperature controlled. FIGS. 14A-13B find particular application for various types of semi-enclosed display areas or storage cases that can be temperature controlled. FIGS. 15A-15D present applications for various types of open-air racks, stands, service cases and display cases that can be temperature controlled.

With further reference to FIG. 13A, the exemplary embodiment illustrates monitor/detector (20) or monitoring system (16) or sensors (S) deployed inside of a service display case (SDC). The exemplary embodiment has the sensors (S) attached to or embedded in the inner walls or linings of the case (110). The sensors (S) are attached to or embedded in the covering of the display cases (111). The position of the sensor(S) is in a manner in which the sensor receives air flow within the case (110). In some instances, concentrators including fans, pumps, vents and flow channels among other active/passive flow induction mechanisms (26) are used to enhance functionality of the monitor/detector (20). Within the exemplary food case (110), various approaches to chemical detection can be utilized, including placing sensors (S) on surface areas within the food case, including trays (112), racks, stands (113) and signs among types of equipment, smart infrastructure, smart equipment or surface areas within a food case (110). In some instances, the sensor (S) can be printed directly on or attached to the material or equipment such as trays (112) or stands (113)

within the case (110). In situations where the cases are used to display perishable foods with ice or other types of cooling agents, sensor (S) capable of detecting chemicals in liquid are deployed in areas where liquid collects within the case (110). Sensors (S) can also be attached or embedded in the cooling agents themselves among other various suitable sensor deployments.

Figure 13B:
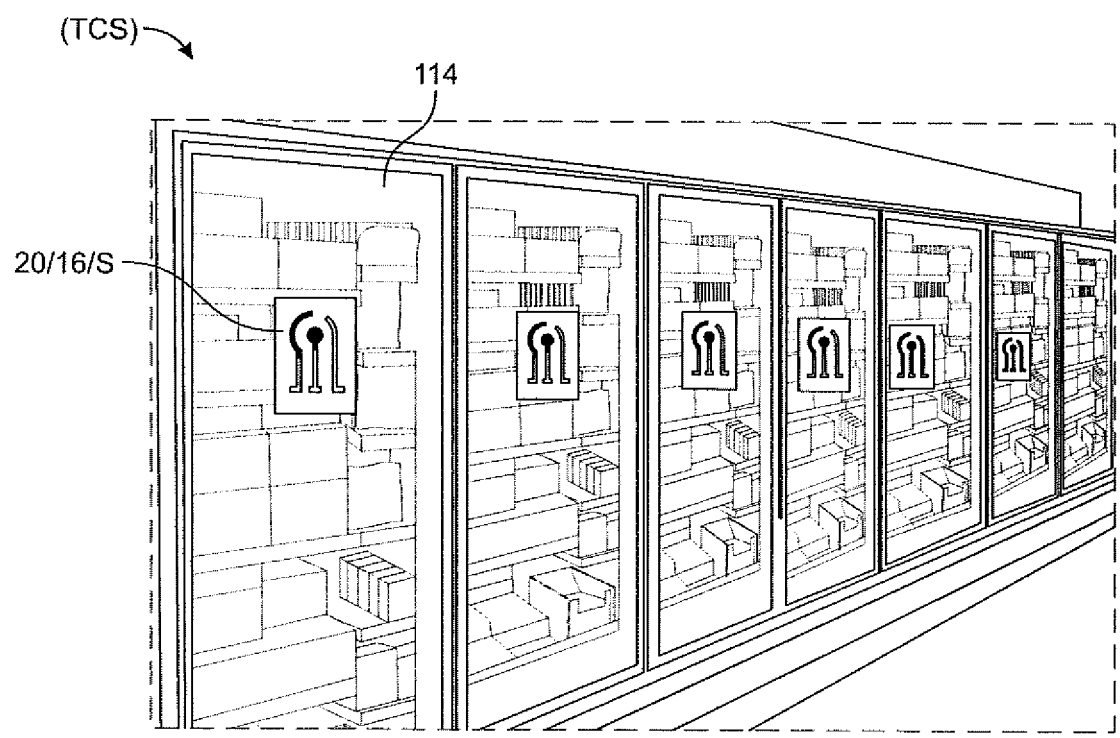

FIG. 13B illustrates monitor/detectors (20) or monitoring systems (16) or sensors (S) deployed in temperature-controlled storage (TCS). Modifications to the sensors (S) can be made to ensure proper functionality in the cold or various harsh environments. Such modifications can include temperature-resistant coatings and gels applied to a monitor/detector (20) as well as other modifications made to other components and elements of the sensors (S). Such modifications could include using a flow induction (26) to sample air or liquid or other substance from an extreme environment, while the other components of the sensor (S) are located in areas of more moderate conditions. The induction device (26) or sampler can be located apart from other components and elements of the sensor (S) and system (SYS). If necessary, the temperature of the sample (e.g. air, liquid, vapor or other substance) can be adjusted using a heating or cooling component, which can be part of the sensor (S) or selectively attachable to the sensor (S) or separate from the sensor (S). The heating/cooling component can be separately replaceable within the monitoring system (16) and can include its own power supply. Alternatively, the heating/cooling component can be configured to receive power from power supply (24). The sample can travel through a flow conduit or similar material or equipment from the induction device (26) to the heating/cooling component and then onto the monitor/detector component (20) for detection, monitoring or measuring of chemical concentration. The sensors (S) or induction devices (26) can be placed in or on doors of freezers, refrigerators as well as other components of the temperature-controlled storage (TCS).

The exemplary embodiment has been described with reference to the preferred embodiment of detecting, monitoring or measuring chemical concentrations in harsh environments using induction devices or samplers (26) remote from other components of the sensor (S) or connected to the sensor components through a flow conduit that can have a temperature control component. Obviously, modifications and alterations will occur to others upon reading and understanding the preceding detailed description. It is intended that the exemplary embodiment be construed as including all such modifications and alterations insofar as they come within the scope of the appended claims or the equivalents thereof.

Figure 14A:
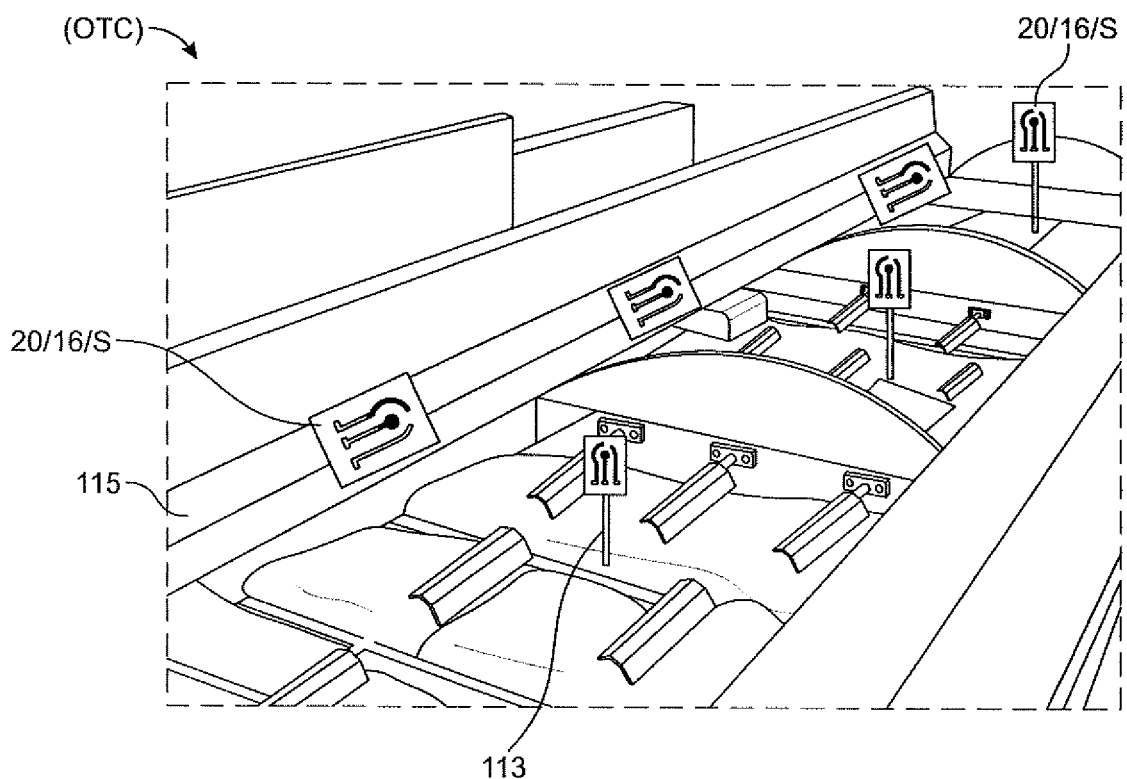
FIGS. 14A-14B illustrate exemplary deployments of sensors for semi-enclosed areas in accordance with the present disclosure.
Figure 14B:
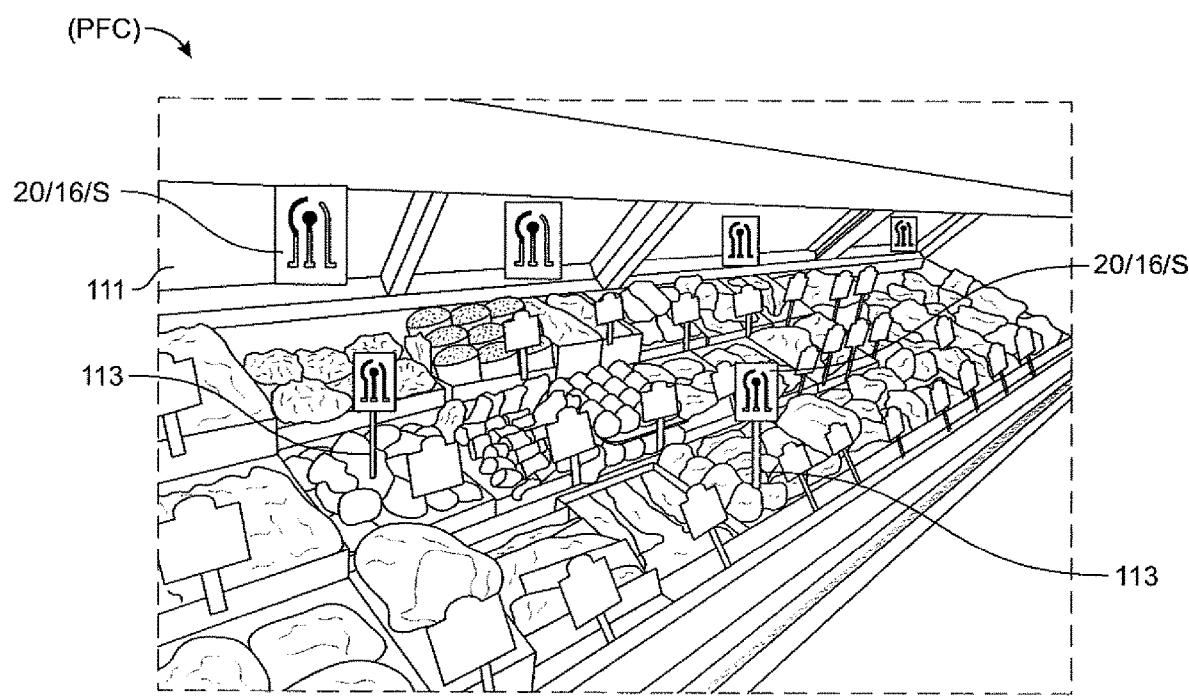

FIGS. 14A-14B illustrate exemplary embodiments where monitors/detectors (20) or monitoring systems (16) or sensors (S) are deployed in semi-enclosed areas. FIG. 14A illustrates monitors/detectors (20) or monitoring systems (16) or sensors deployed in temperature-controlled storage (OTC). FIG. 14B illustrates monitors/detectors (20) or monitoring systems (16) or sensors (S) deployed in semi-enclosed prepared food cases (PFC). With further reference to FIG. 14A, sensors (S) are deployed inside and outside of open-air, temperature-controlled storage (OTC). The sensors (S) are placed in locations conducive to flow of air, liquid or other substance, specifically along the back of the storage case (115) where the environment can be less harsh and air flow is greatest. Sensors (S) can also be placed on stands (113) or signs or other smart infrastructure or smart equipment, ensuring that vapor or gas or air or other substance comes into contact with the monitor/detector (20). Similar to previous disclosures, sensors (S) are strategically placed to optimize the flow of air or other substance across the sensors (S), leveraging active/passive air flow induction mechanisms (26) or samplers. Certain types of cold storage (e.g. freezers or refrigerators), often have air flow mechanisms to keep warm air from entering the cooling region. These designs work especially well with the active/passive air flow induction mechanisms (26) that are part of the sensor (S) as disclosed in FIG. 13B.

With further reference to FIG. 14B, sensors (S) are deployed throughout semi-enclosed prepared food cases (PFC). The sensors (S) can be attached or embedded in covering or linings or wrapping (111) of the prepared food cases (PFC). The sensors (S) can be deployed in areas above the food/beverage/drug. Such deployment location is advantageous in that it takes advantage the properties of gases that make them rise (e.g. less dense gases rise relative to the denser air around it). The sensors (S) can also be attached to stands (113), which are placed throughout the prepared food case (PFC). In this embodiment as well as others, various elements and components of the sensor (S) can be built into the stand (113) in such a way that the monitor/detector (20) can be easily removed and replaced. As such the stands (113) can serve as "smart equipment", whereby the stand (113) contains sources of power and communication etc.

Figure 15A:
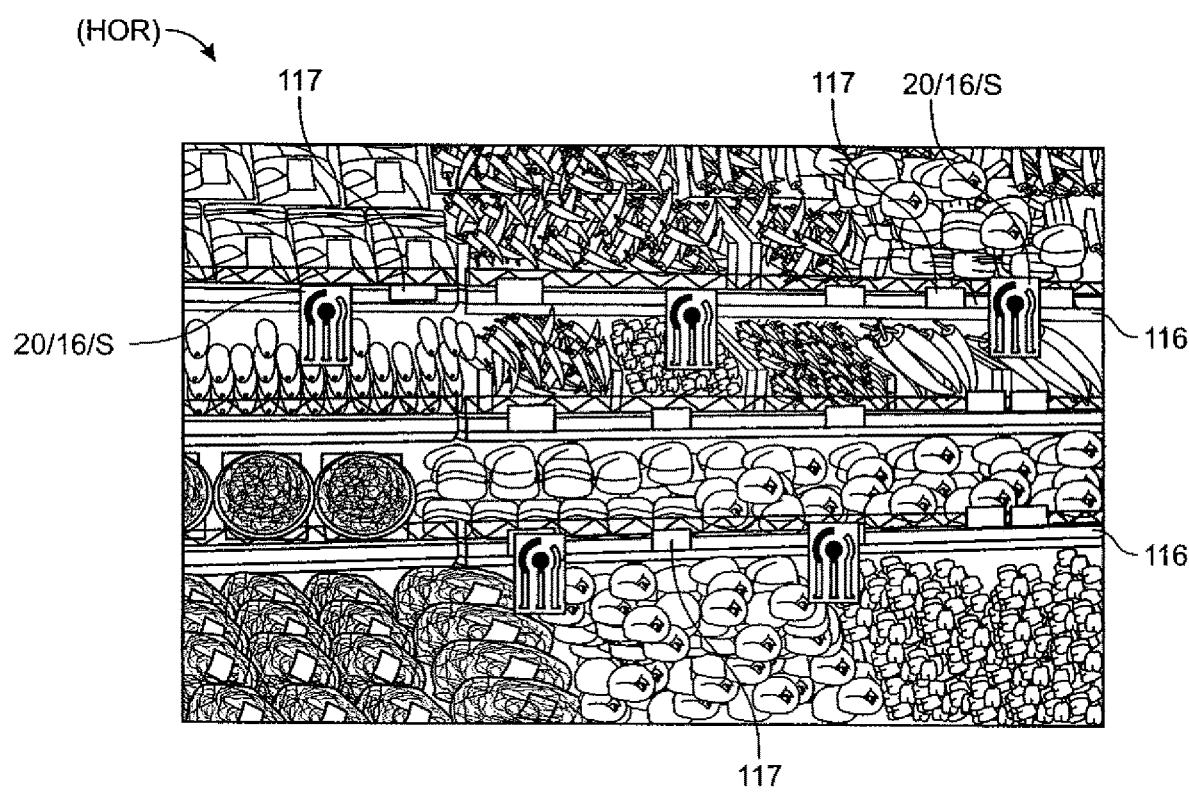
FIGS. 15A-15D illustrate exemplary deployments of sensors for open-air areas in accordance with the present disclosure.

FIGS. 15A-15D illustrate exemplary embodiments for various types of open-air racks, stands, cooling cases, service cases or display cases. FIG. 15A presents an application whereby monitor/detectors (20) or monitoring system (16) or sensor (S) can be hung on racks (HOR). The monitor/detector (20) connects with other components and elements of the sensor (S) that are built into the racks (116). The built-in components and elements of the sensor (117), include components and elements of the sensor (S) (e.g. communication circuitry (22), active/passive power source (24) or active/passive flow induction (26) etc.) or components and elements of the printed circuit board (PCB) (e.g. antenna (52), microcontroller unit (53), voltammetry circuit (54) and connector (55) etc.) The built-in components or elements (117) can be such that a monitor/detector (20) can be easily connected or removed from the built-in components or elements (117). The connection can be made simply by hanging the monitor/detector (20) on the rack (116). It should be appreciated and understood that more conventional methods of connecting the monitor/detector (20) to the built-in components or elements (117) of the rack (116) could also be used. Such methods can include those connections disclosed in FIGS. 8A-8D and FIGS. 11A-11D.

It should also be appreciated and understood that this feature of offloading components and elements of the sensor (S), which are typically the most expensive components or elements allows for a reduction of cost, by allowing the most expensive components and elements of the sensors to be used repeatedly and continuously. Such built-in components and elements (117) can have additional features such as rechargeable power supplies and units, components and elements that are removeable and replaceable. The built-in components and elements (117) can also be stationary or mobile within a location in a facility or store. The built-in components (117) can be located near food/beverage/drug or located remotely from food/beverage/drug. The built-in components and elements (117) can also be deemed "smart infrastructure" or "smart equipment" and can be applied to other disclosed embodiments. As previously disclosed in FIG. 2 the "smart infrastructure" or "smart equipment" can contain not only elements and components of the sensor (S), but also components and elements of the associated receiver (AR). As such, the monitor/detector (20) can be easily removed from the "smart infrastructure" or "smart equipment" and replaced as needed.

Figure 15B:
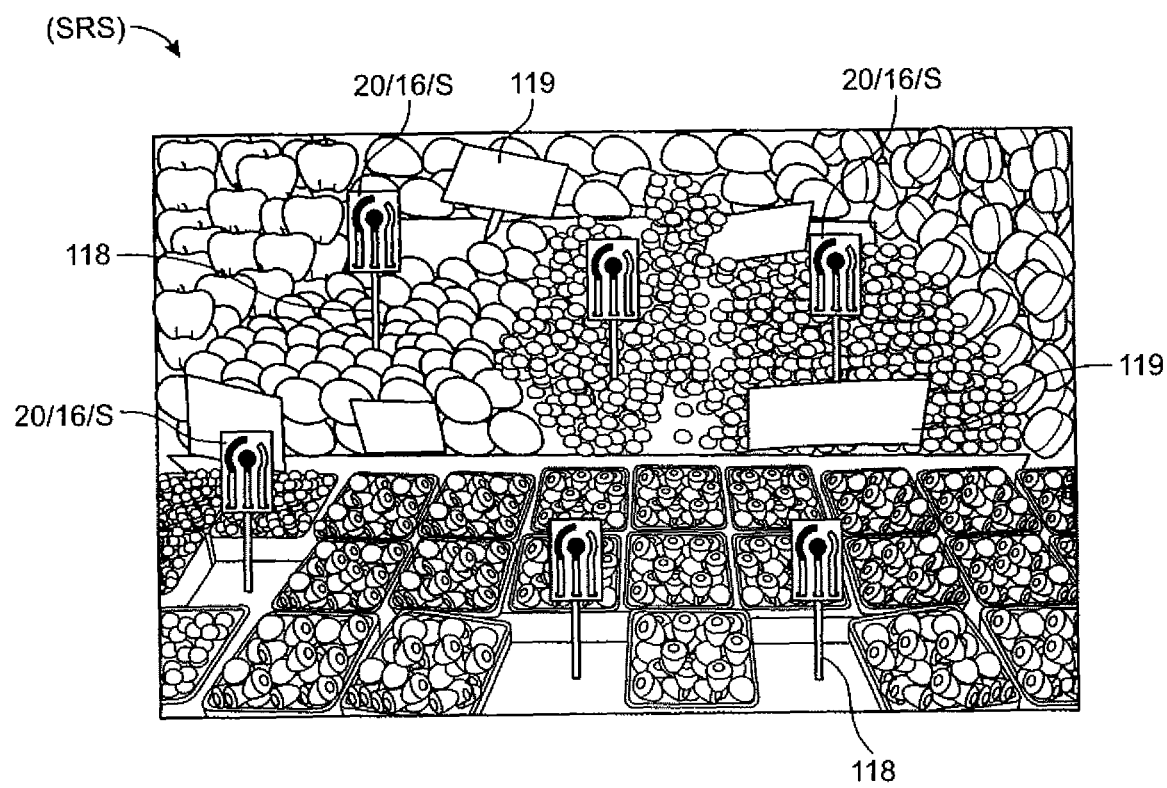

FIG. 15B presents an application whereby monitor/detectors (20) or monitoring systems (16) or sensors (S) are placed on rechargeable stands (SRS) in a produce display. The stands (118) known as "smart equipment" supply wireless connectivity and power that is rechargeable. The stands (118) are placed strategically throughout a food display. The display can also contain digital displays or signs (119) also known as "smart equipment". The digital displays (119) can convey information not only about the price of the food item or other helpful information, but also the quality and state of freshness of the food item. The displays or signs (119) have integrated Bluetooth radio, wifi or other suitable radio as well as power supply that can be recharged. The features allow the displays to be updated in real-time and sync in real-time with the associated sensors (S) or systems (SYS). In this present embodiment as well as others, it should be appreciated and understood that a digital shelf or sign (119) can be considered an associated receiver (AR) and part of the monitoring system (SYS). In addition to conveying data related to food safety, security and quality, the digital shelves or signs (119) improve the effectiveness of marketing, deliver an enhanced shopping experience to the consumer and create operational efficiency by streamlined restocking and dynamic price adjustment factoring discounts and promotions.

The sensors (S) and broader monitoring system (SYS) deployed inside food stores or retail facilities creates a digital experience for customers in that they can receiver data or information in real-time on their smartphones (P) or through "smart equipment" such digital shelf or sign (119) related to food they consider purchasing. The data or information could relate to food freshness or it could relate to where the food came from as well as other information.

The exemplary embodiment has been described with reference to the preferred embodiments of smart infrastructure or smart equipment serving as the associated receiver (AR) of the system (SYS). Obviously, modifications and alterations will occur to others upon reading and understanding the preceding detailed description. It is intended that the exemplary embodiments be construed as including all such modifications and alterations insofar as they come within the scope of the appended claims or the equivalents thereof.

Figure 15C:
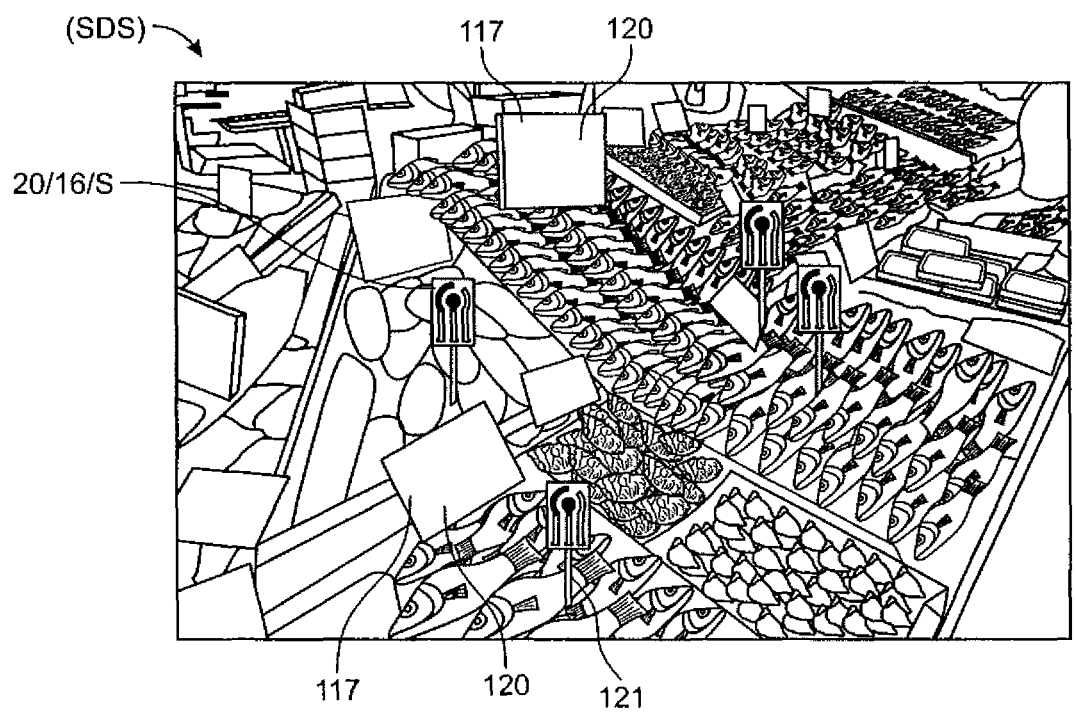

FIG. 15C presents an application whereby monitors/detectors (20) or monitoring systems (16) or sensors are placed on display signs and stands (SDS) located near cooling agents used in a seafood display. The exemplary embodiment includes sensors (S) that can detect chemicals, analytes and other factors in liquid. The sensors are attached or embedded in the base of the display signs (120) and stands (121) among other infrastructure or equipment that can be outfitted with associated receivers (AR). The sensors (S) are able to interact with liquids or other run-off from cooling agents directly in contact or indirectly in contact with food/bevarage/drug. Similar with previous disclosures, the display signs (120) and stands (121) can contain supplies of power and connectivity (117) so that they are not required on the actual sensor (S). The supplies last a long time, are rechargeable and can be stationary or mobile throughout the facility. It should be appreciated and understood that the present embodiment is similar to other disclosures from FIGS. 13A-15B, however the unique feature of the present disclosure has to do with using liquid sensor (S) to detect chemicals in fluids (e.g. ice or water or other forms of fluid). The embodiment is suitable for food/beverage/drug displayed over ice or other forms of cooling agents.

Figure 15D:
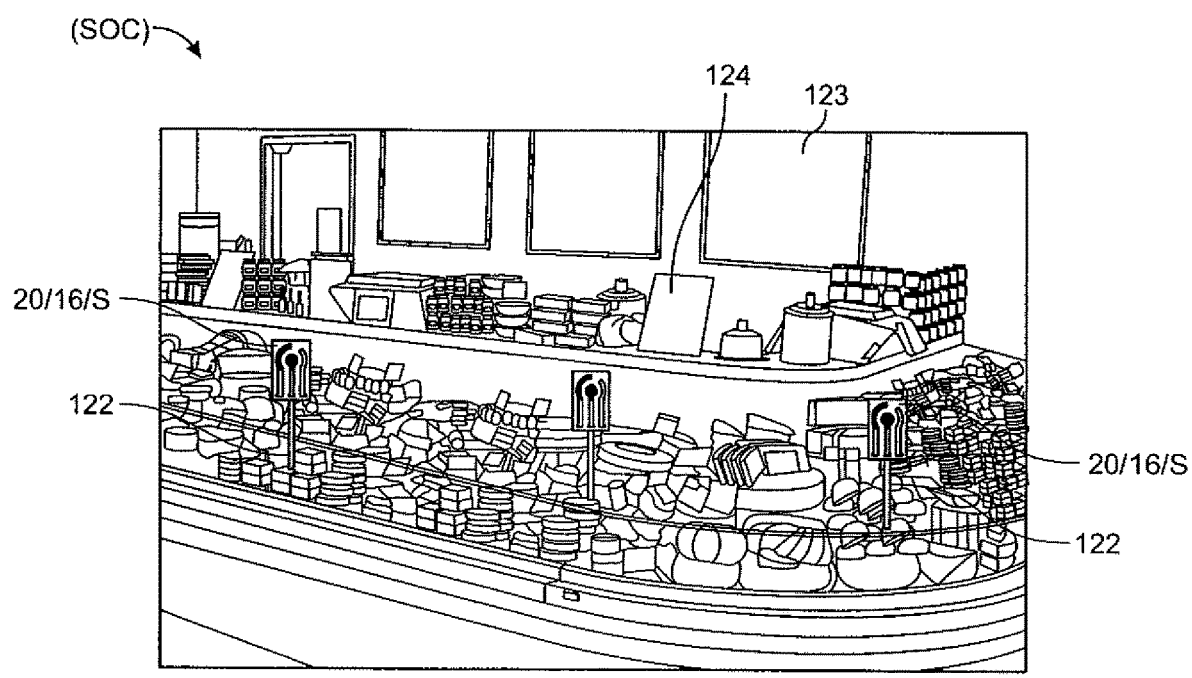

FIG. 15D presents an application whereby monitors/detectors (20) or monitoring systems (16) or sensors (S) are placed in or on stands in open-air cases displaying dairy and bake good or other food/beverage/drug products (SOC). Similar to other disclosures, sensors (S) can leverage supplies of power and wireless connectivity from "smart equipment" such as stands (122) built-in supplies (117) on racks (116) etc. The stands (122) can also include temperature sensors among other plurality of detectors (28) for detecting, monitoring and measuring chemicals, analytes or other factors in food/beverage/drug or the environment of food/beverage/drug. The sensors (S) and stands (122) transmit data and information that a consumer would want to know. The data or information can be transmitted to a consumer's phone (P) or to large display signs (123) or small display signs (124). The data and information can relate to freshness, ingredients or any other factors related to food/beverage/drug. The data and information can also be shared with store clerks, stockers and other personnel. Such data and information can help improve operational efficiency by streamlining restocking and dynamically adjusted pricing to accommodate promotions and in-store marketing. The data and information can also feed algorithms, machine learning or artificial intelligence that compose dinner plans for a shopper. For example, a shopper can use their personal communication device to interact with items and the automated shopping assistant can suggest what other items to purchase for particular meals along with other helpful information such as nutritional value, food expiration date, promotions etc. The shopping assistant can plan meals based in-part from sensor data, automatically populating a meal planning calendar. Essentially, the automated shopping assistant can guide the shopper in creating a meal schedule and getting all the items necessary for all the meals.

The exemplary embodiments have been described with reference to the preferred embodiments of using data from the sensor (S) or system (SYS) to drive or train an automated shopping assistant. Obviously, modifications and alterations will occur to others upon reading and understanding the preceding detailed description. It is intended that the exemplary embodiment be construed as including all such modifications and alterations insofar as they come within the scope of the appended claims or the equivalents thereof.

Figure 16A:
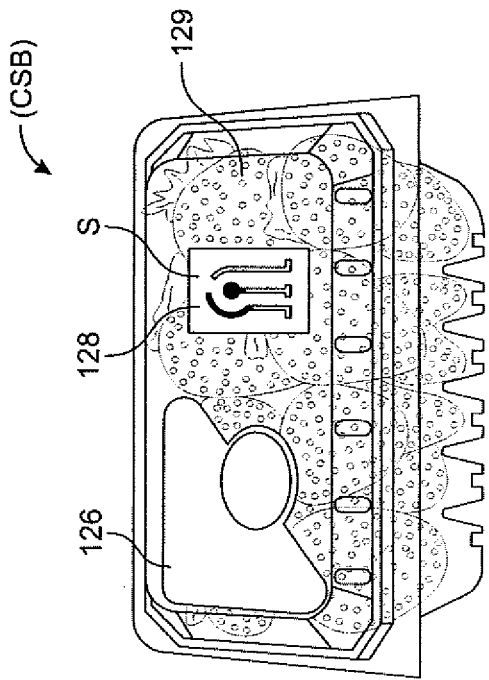
FIGS. 16A-16D illustrate exemplary deployments of sensors for containers and packages in accordance with the present disclosure.
Figure 16B:
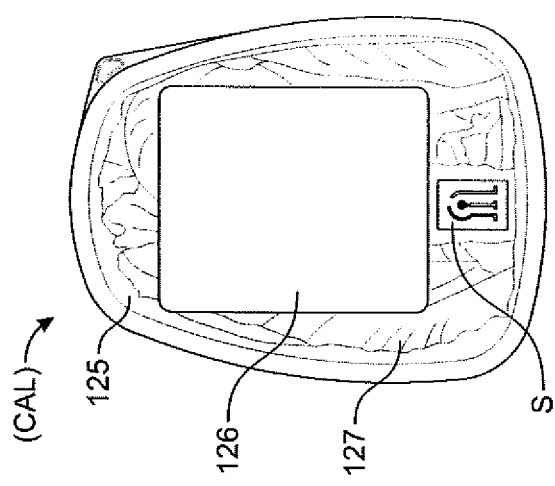
Figure 16C:
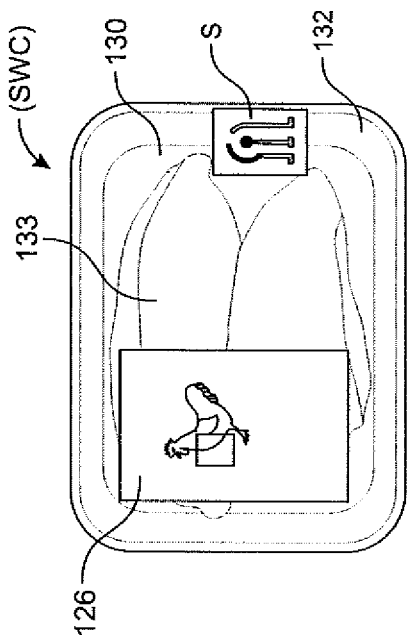
Figure 16D:
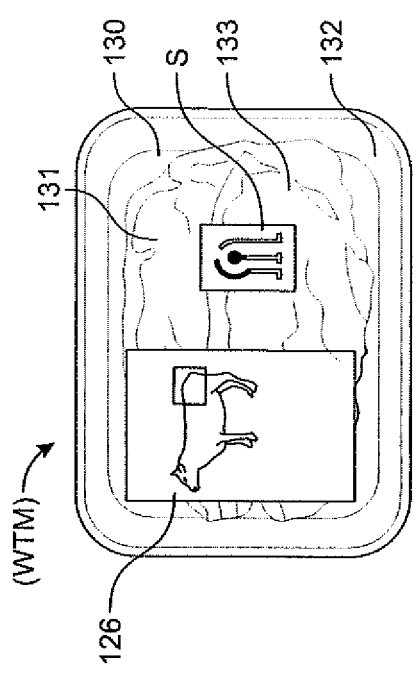

FIGS. 16A-16D illustrate exemplary devices, systems and methods for detecting, monitoring or measuring chemicals, analytes and other factors in food/beverage/drug/beverage or the environment of food/beverage/drug/beverage throughout the supply chain (SYS) as part of Phase (D) in the method (METH=A+B+C+D) disclosed in FIG. 1. FIGS. 16A-16D present embodiments of deploying sensors (S) inside of packages or containers. FIG. 16A illustrates a sensor (S) in a plastic case of romaine lettuce (CAL). FIG. 16B illustrates a sensor (S) in a clamshell package of berries (CSB). FIG. 16C illustrates a sensor (S) in a wrapped tray holding meat (WTM). FIG. 16D illustrates a sensor (S) in a skin wrapped package of chicken (SWC).

In FIG. 16A, the sensor (S) is attached or embedded in a lid (125) of a plastic case (CAL). Other placements of the sensor (S) can include the sides of the container as well as the base of the container. At least one of the elements or components of the sensor (S) can be embedded or attached to the product label (126) or other types of various packaging or adhesives. Embedding printed electronics, elements and components of the sensor (S) such as communication circuitry (22), active/passive power source (24) and even memory (32) and processor (30) or other element and components of the printed circuit board (PCB) in a product label are especially useful when using low-power monitor/detector (20). In some embodiments the power source (24) of the monitoring device (16) can be an antenna for receiving electromagnetic energy. The illustration presents lettuce (127), however it should be appreciated that other types of food/beverage/drug (e.g. seafood, meat, poultry, vegetables and fruits among other types of food/beverage/drug) can be included in the present embodiment.

FIG. 16B presents another embodiment for deploying sensors (S) in a clamshell package (CSB) using a carrier material (128). The sensor (S) is applied to the carried material (128) and deposited in the clamshell package of berries (CSB). The illustration presents berries (129); however, it should be appreciated that other types of foods (e.g. seafood, meat, poultry, vegetables and other types fruits among other types of food/beverage/drug) can be included in the present embodiment. The carrier material (128) with the sensor (S) attached or embedded, can be mobile within the clamshell of berries (CSB) or it can be tethered to the clamshell (CSB) or pasted directly to the clamshell (CSB). The carried material (128) may sit inside of the clamshell (CSB) above the food or below the food or on either side of the food. Other modifications to the carried material (128) can be made such that the modification help preserve the food in the clamshell (CSB). Such modifications can include making the carried material (128) with properties that control or reduce moisture or humidity or other gases or vapors or factors that are known to preserve or enhance the shelf life of food. In one embodiment the carried material (128) can be of an absorbent pad (ADP) used to control moisture or various gases or various vapors or humidity or pH among other factors inside of a container or clamshell (CSB) as disclosed in FIG. 20B. Additional features of the present disclosure can include anti-bacterial, anti-microbial, ethylene absorbency among other features that limit the potential of spoilage and contamination.

Similar to previous embodiments, at least one component or element of the sensor (S) can be of a printed component or element and can be part of the product label (126) or an added label or other type of adhesive or packaging or material that binds or adheres to a package. A sensor type that is particularly well suited for this embodiment include the sensor unit (SU) and sensor array (SA) disclosed in FIGS. 3B(i) and 3B(ii) and the cellophane sensor (CS) disclosed in FIG. 3C(i) and FIG. 3C(ii). Methods for adhering the sensor (S) to wrapping (130) that are particularly well-suited for purposes of the present disclosure are set forth in U.S. Pat. No. 8,674,827 to Hummer et al., of which are incorporated herein by reference in its entireties. Other types of monitor/detector components (20) can also be used in accordance with the present disclosure.

FIG. 16C presents another embodiment for deploying sensors (S) in a wrapped package or wrapped tray of meat (WTM). The sensor (S) is attached to or embedded in wrapping (130) or covering a piece of meat (131) on a tray (132). In such an embodiment, the sensor (S) can be directly contacting the meat (131) or separated from the meat (131) (e.g. FIGS. 17A-17D disclose various methods of affixing, embedding or placing sensor in wrapping). A liquid or gel-like substance (133) that improves the performance of the sensor (S) and also preserves the meat (131) can be used. FIG. 16C presents a piece of meat (131), however it should be appreciated that other types of food/beverage/drug (e.g. seafood, poultry and fruits among other types of food/beverage/drug) can be included in the present embodiment. Similar to previous embodiments, at least one component or element of the sensor (S) can be of a printed element or component and can be part of the product label (126) or an added label or other type of packaging or adhesive or material that binds or adheres to the food package. A sensor type that is particularly well suited for this embodiment include the sensor unit (SU) and sensor array (SA) disclosed in FIGS. 3B(i) and 3B(ii) and the cellophane sensor (CS) disclosed in FIG. 3C(i) and FIG. 3C(ii). Methods for adhering the sensor (S) to wrapping (130) that are particularly well-suited for purposes of the present disclosure are set forth in U.S. Pat. No. 8,674,827 to Hummer et al., of which are incorporated herein by reference in its entireties. Other types of monitor/detector components (20) can also be used in accordance with the present disclosure.

A modification to this exemplary embodiment could include placing the sensor (S) directly on the meat (131) without adhering the sensor to the wrapping (130). Another modification to this embodiment could include a wrapping (130) without a tray (132). In such an exemplary embodiment the sensor (S) would be attached or embedded directly in the wrapping (130). These types of packages are commonly referred to as skin wrapping or vacuum wrapping or vacuum packing. Other methods can remove air, but also add other vapors or gases that act to preserve the food/beverage/drug.

FIG. 16D illustrates another exemplary embodiment of deploying sensors (S) in a food container or package or wrapping by attaching or embedding the sensor (S) to a tray (132) or similar material designed for carrying, protecting and storing food. The illustration presents a piece of chicken (133), however it should be appreciated that other types of food/beverage/drug (e.g. seafood, poultry, vegetables and fruits among other types of food/beverage/drug) can be included in the present embodiment. Similar to previous embodiments, at least one component or element of the sensor (S) can be of a printed element or component and can be part of the product label (126) or an added label or other type of packaging or adhesive or material that binds or adheres to the food package. Such printed elements or components can also be printed on or attached to any carried material inside or outside the food package. Such carried material can include: a tray (132), an adsorbent pad (147), an absorbent pad (148), protective pads, among any other type of material related to a food container or package.

FIGS. 17A-17D present illustrations of exemplary devices, systems and methods for detecting, monitoring or measuring chemicals, analytes and other factors in food/beverage/drug or the environment of food/beverage/drug throughout the supply chain (SYS) as part of Phase (D) in the method (METH=A+B+C+D) disclosed in FIG. 1. FIG. 17A illustrates a sensor (S) applied to the outside of a cover or wrapping or packaging (SOP). FIG. 17B illustrates a sensor (S) embedded in a cover or wrapping or packaging (SEC). FIG. 17C illustrates a sensor (S) deployed inside of a cover or wrapping or packaging, whereby the sensor (S) is not touching the food/beverage/drug (SNF). FIG. 17D illustrates a sensor (S) deployed inside of a cover or wrapping or packaging, whereby the sensor (S) is touching the food/beverage/drug (STF). It should be appreciated that the embodiments presented in FIGS. 17A-17D do not have to include the adsorption/absorption pad (134) or the tray (132). The embodiments could be food/beverage/drug (134) in packaging (130) of various types including container, bottle, can, carton, bag among other materials used to store, transport and sell food/beverage/drug.

FIG. 17A presents an exemplary embodiment whereby sensors (S) are applied to the outside of a cover or wrapping or packaging (SOP). While it is not optimal for a sensor (S) to puncture or protrude through a cover or wrapping or packaging (130), the method of deploying sensors (S) from outside a package is beneficial in that the sensors (S) can be easily added or removed from the package without having to unpack items. Such methods of deploying sensors (S) can be used in conjunction with covers or wrappings or packaging (130) that have self-healing properties or other mechanisms for fixing a puncture in packaging (130). The sensors (S) could also be capable of functioning from outside the packaging or wrapping (130), whereby no puncture needs to be made. A label (126) or other type of covering, can be used to cover the puncture. The present embodiment can also include a pad for adsorbing fluid or absorbing gases (135).

FIG. 17B presents an exemplary embodiment where the sensor (S) is embedded in a cover or wrapping or packaging (130) that can have self-healing properties and/or adsorption/absorption capabilities (SEC). A sensor (S) particularly well suited is the cellophane sensor (CS) disclosed in FIGS. 3C(i) and 3C(ii). In the exemplary embodiment, the cellophane sensor (CS) would be embedded in the cover or wrapping or packaging (130) that can have self-healing and/or adsorption/absorption properties. The embedded sensor (S) could span only part of the covering (130) or the entire covering (130). For bottles or cans, the covering (130) can serve as a seal between the bottle or can and the top or lid of the bottle or can. The present embodiment can also include a pad for adsorbing fluid or absorbing gases (135).

It should be appreciated that at least one or all elements and components of the sensor (S) can be of printed elements or components. Such printed elements or components can be in the form of seals, labels, stickers or other types of markings, adhesives, wrappings or various packaging. The self-healing, adsorbent/absorbent cover or wrapping or packaging (130) with the embedded sensor (S), could detect unwanted factors in the environment of food/beverage/drug such as a change in temperature, change in humidity, change in moisture, change in pH, change in composition of ambient air of enclosed packaging, change in chemical composition (e.g. bacteria, spoilage, contamination etc.) among other factors and take corrective action through the self-healing properties of the wrapping (130) with embedded sensor.

An exemplary form of corrective action could include absorbing gases in order to minimize or slow ripening, spoiling, decay or rotting. Such gases can include ethylene, ethylene oxide, calcium carbide, acetylene, iodine, oxygen, nitrogen among other chemicals or gases. The absorbing of gases associated with ripening or decay can be performed by the packaging or wrapping (130) or it could be performed by the sensor (S) or the adsorption/absorption pad (135). Absorbing gasses can be done for packages containing food, but also drugs, like cannabis.

The wrapping (130) can comprise of linear low-density polyethylene plastic film along with additives for absorption of ethylene or other gases or vapors. An exemplary wrapping (130) for food and drugs like cannabis can comprise of an anti-fog additive to reduce water droplets and moisture as well as other elements for controlling humidity, moisture, temperature, pH, various vapors or gases and nutrient availability. Such wrappings can be in the form of package wrappings, pallet covers, carton liners among other types of bags, packaging or wrapping (130).

While this particular disclosure relates to combining chemical sensing with covers or packaging or wrapping (130) that can remove, add or adjust levels of chemicals or gases or vapors associated with decay and contamination, thus extending the shelf life of food/beverage/drug and helping to prevent the growth of bacteria, particularly anaerobic bacteria, it should be appreciated that these properties can be applied to other disclosed devices, systems and methods. For example, such methods include incorporating the properties of ethylene absorption and ethylene detection on a carried material (128) that can be deposited into a food/beverage/drug container or package. Other examples include red meat, which requires high levels of oxygen in order to maintain its red color and bread, which requires low oxygen to avoid mold and vegetables, which require a mix of oxygen, carbon dioxide and nitrogen. Drugs such as cannabis is frequently tested for fungus, mold, pesticide among other unwanted adulterants additives or factors. A comprehensive guide for recommended gas mixtures in food packages is included in the appendix of this disclosure.

FIG. 17C illustrates a sensor deployed inside a package, whereby the sensor is not touching food (SNF). In the present embodiment, the sensor (S) is attached to the inside of the cover or wrapping or packaging (130). In a typical package, space exists between the top of the package and the food/beverage/drug (134). Since gases like ethylene are lighter than air, the gas would rise to the top of the package. This factor among others will in-part determine the location of the sensor (S) within the package. The attached sensor (S) could span only part of the covering (130) or the entire covering (130). For bottles or cans, the covering (130) can serve as a seal between the bottle or can and another covering such as a top or lid of the bottle or can. The present embodiment can also include a pad for adsorbing fluid or absorbing gases (135).

FIG. 17D illustrates a sensor deployed inside cover or wrapping or packaging, whereby the sensor touches the food/beverage/drug (STF). The sensor (S) can be contacting the food/beverage/drug (134). Methods of contact can include invasive (e.g. deeply penetrate the fish by more than 1 millimeter) or minimally invasive (e.g. penetrate the fish by 1 millimeter or less) or non-invasive (e.g. not penetrate the fish, but touching). The sensor (S) can also be free to move around the package or the sensor (S) can also be applied to a carried material (128) that is either free to move around the food package, tethered to the package with limited ability to move around the package or adhered to the package with no ability to move around the package.

Exemplary embodiments for deploying sensors (S) outside of a cover or wrapping or packaging or inside a cover or wrapping or packaging or embedded in a cover or wrapping or packaging have been disclosed. The embodiments also include cover or wrapping or packaging and pads that are capable of adsorbing gases or absorbing fluid or both. However, modifications and alterations will occur to others upon reading and understanding the preceding detailed description. It is intended that the exemplary embodiments construed as including such modifications and alterations insofar as they come within the scope of the appended claims or the equivalents thereof.

Figure 18:
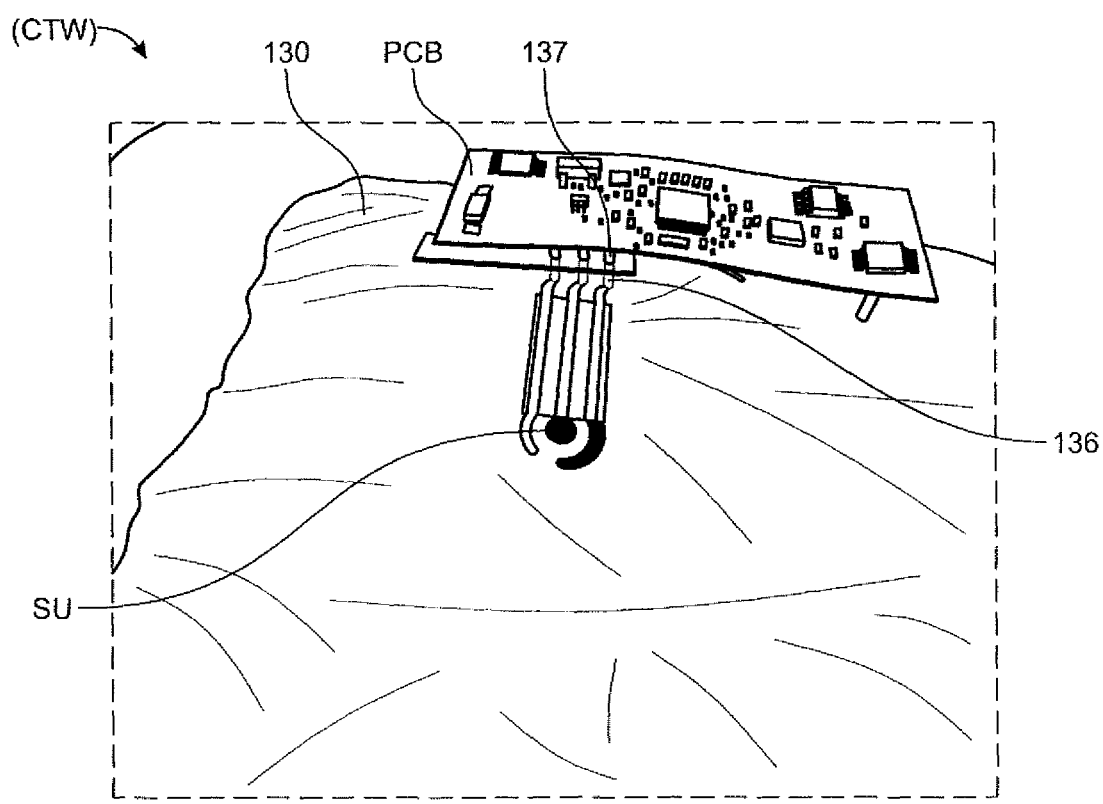
FIG. 18 illustrates exemplary mechanisms and methods for connecting units or components of sensors in accordance with the present disclosure.

Turning to FIG. 18, an embodiment related to mechanisms and methods for connecting a monitor/detector (20) with at least one other component or element of the sensor (S) is disclosed (CTW). FIG. 18 illustrates the electrodes (e.g. reference electrode (46), working electrode (47) and counter electrode (48)) of the sensor unit (SU) being connected to a printed circuit board (PCB) using magnets (136). The connection using magnets can be made directly between electrodes of the sensor unit (SU) and the printed circuit board (PCB) or indirectly whereby a wrapping (130) or similar type of packing comes between the electrodes of the sensor unit (SU) and the printed circuit board (PCB).

In the present embodiment, the electrodes of the sensor unit (SU) can be made of pulverized metals or materials that have magnetic properties, which allow for a secure connection between the electrodes of the sensor unit (SU) and the printed circuit board (PCB). Similarly, elements and components of the printed circuit board (PCB) can be made of pulverized metals or materials that have magnetic properties, particularly elements of various types of connectors (137) that can be used to join the electrodes of the sensor unit (SU) and the printed circuit board (PCB).

It should be appreciated that the printed circuit board (PCB) can be used on multiple packages. This feature offers benefits because typically the costliest components of a sensor (S) are those of a printed circuit board (PCB), primarily the active/passive power source (24) and communication circuitry (22) among other elements and components such as the voltammetry circuit (54), antenna and the microcontroller unit (53) as disclosed in FIG. 4.

Figure 19:
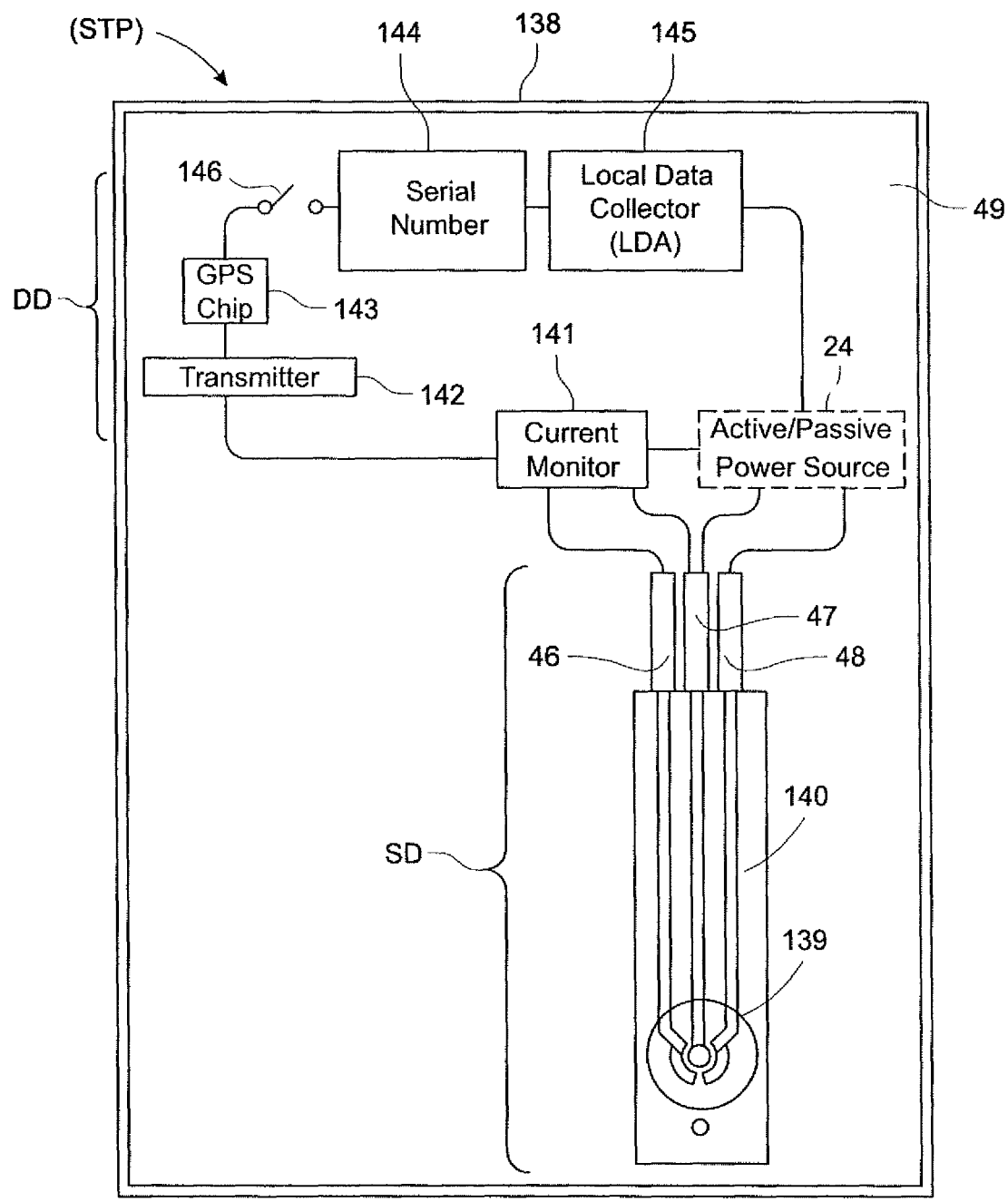
FIG. 19 is a functional block diagram of a sensor strip in accordance with the present disclosure.

FIG. 19 illustrates an exemplary sensor strip (STP) that comprises of one or more printed units, components or elements. The sensor strip (STP) is enclosed in a factor-resistant pouch or envelope (138) and can have removeable and replaceable units, components or elements.

The sensor strip (STP) comprises two major devices, a sensor device (SD) and a detection device (DD). The two major devices can either be part of a single unit that has no removeable and replaceable parts or be part of multiple units that have removeable and replaceable units, components or elements. A unique feature of the factor-resistant pouch or envelope (138) is that it can be sealed or unsealed (e.g. open or closed) in order for units, components or elements to be removed and replaced on the multiple unit version.

The sensor strip (STP) comprises of a common strip or substrate (49), upon which other elements or components of the two major devices, the sensor device (SD) and the detection device (DD) are printed or mounted. The common strip or substrate (49) can be in the form of a printed strip, tag or label that can be made of polyester or other electrically non-conductive material, such as other polymeric materials, alumina, ceramic based materials, metal oxides, glass or a semi-conductive substrate, such as silicon, silicon oxide and other covered substrates. The printed strips can be thick film which utilizes a high temperature production process, or the strips can be printed electronics, which utilizes a low temperature production process. The printed electronics can consist of organic polymers, conductive inks and nanoparticle inks that allow for flexibility, lightweight and durable properties. The substrate (49) can be biocompatible and enclosed in a factor-resistant envelope or pouch (138) that can be biocompatible as well. A printed strip that is particularly well-suited for purposes of the present disclosure is set forth in U.S. Pat. No. 8,674,827 to Hummer et al. Other patents that related to electrophotography printing of sensor devices (SD) and detection devices (DD) include U.S. Pat. No. 7,176,793 to Hummer et al. and U.S. Pat. No. 7,667,593 to Hummer et al. and U.S. Pat. No. 7,667,593 to Hummer et al, all of which are incorporated herein by reference in their entireties.

The sensor device (SD) comprises a monitor/detector (20), which can consist of a plurality of detectors or sensors (28). The plurality of detectors or sensors (28) can detect, monitor or measure chemicals, analytes or other factors such as location, temperature, moisture, humidity, absorption, pH, nutrient availability among other factors. This embodiment presents a sensor device (SD) similar to the sensor unit (SU) disclosed in FIG. 3B(i). The exemplary sensor device (SD) is a three-electrode system including a counter electrode (46), a working electrode (47), and a reference electrode (48). An insulation layer (140) may cover part of the electrodes, leaving tips of the electrodes exposed to the detection environment in region (139).

The sensor device (SD) is operably coupled to the active/passive power source (24) through the working electrode (47) and the reference electrodes (48) and the current monitor (141) is connected to the working electrode (47) and counter electrode (46). The current monitor (141) can be in the form of a voltammetry circuit (54) as disclosed in FIG. 4. Other elements or components of the detection device (DD) include communication circuitry, which can be in the form of a transmitter (142), location circuitry, which can be in the form of a GPS chip (143); a serial number (144), which can be encrypted and a local data adapter or remote data adapter (145), which is capable of multiplexing data which collects signals from the current monitor. The active/passive power source (24) may be disconnected from the elements or components of the sensor strip (STP) by a magnetic switch (146), which completes the circuit with the components (141), (145), (142), (143) and (144) only intermittently. The sensor strip (STP), when activated, may initiate the power source (24) to maintain operation of the detection device (DD). In this way, the power source (24) is not drained two quickly. It should be appreciated that the sensor strips (STP) can also be made without the feature of a magnetic switch (146) that activates the power source (24).

In another embodiment, power is supplied by an antenna configured to receive energy wirelessly and supply the received energy to at least one of the sensor device (SD) or detection device (DD), whereby an active power source may not be required. It should be understood, that when the sensor device (SD) and the detection device (DD) is part of a single unit that a connector assembly (CON) or secure data card (SDC) may not be required. Instead the elements or components of the sensor device (SD) and the detection device (DD) can be printed on the common strip or substrate (49) that is enclosed in a factor-resistant envelope or pouch (138).

Figure 20B:
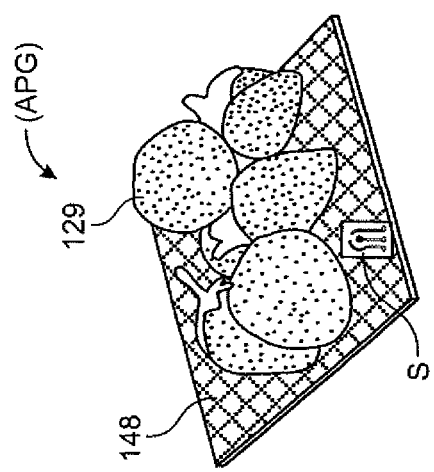
FIGS. 20A-20E illustrate sensor deployments in pads that absorb gas or vapor and adsorb fluid in accordance with the present disclosure.
Figure 20A:
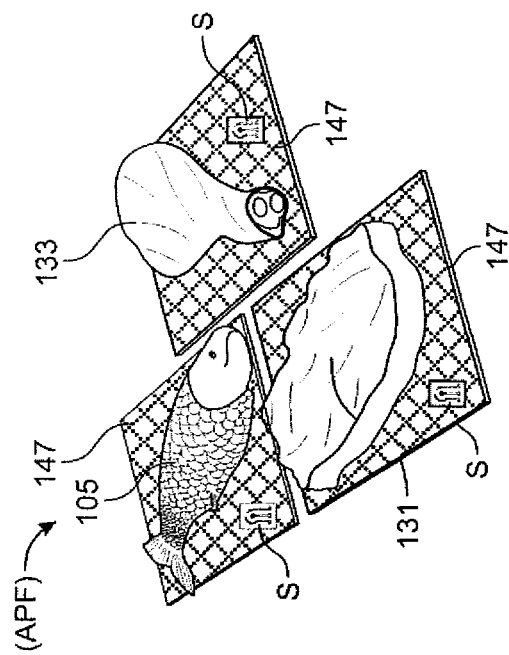
Figure 20C:
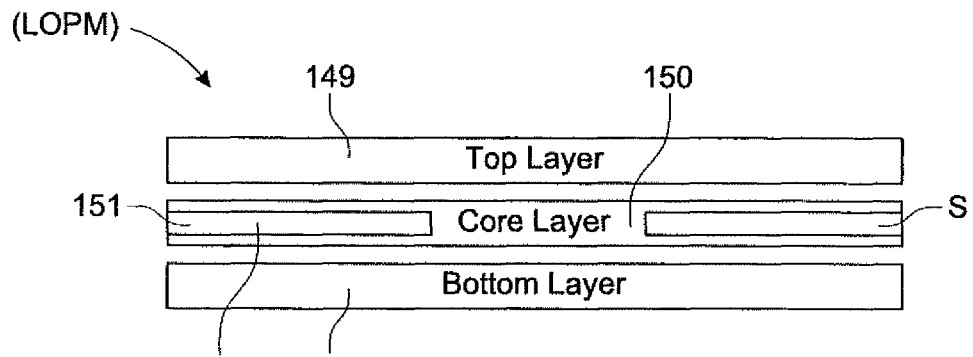
Figure 20D:
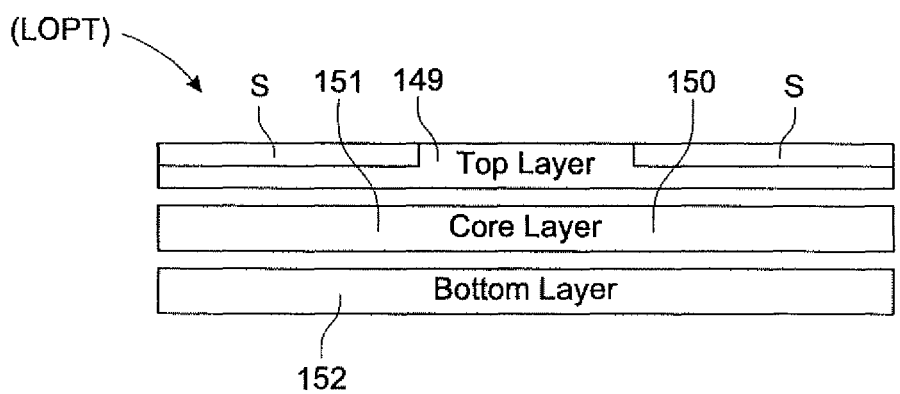
Figure 20E:
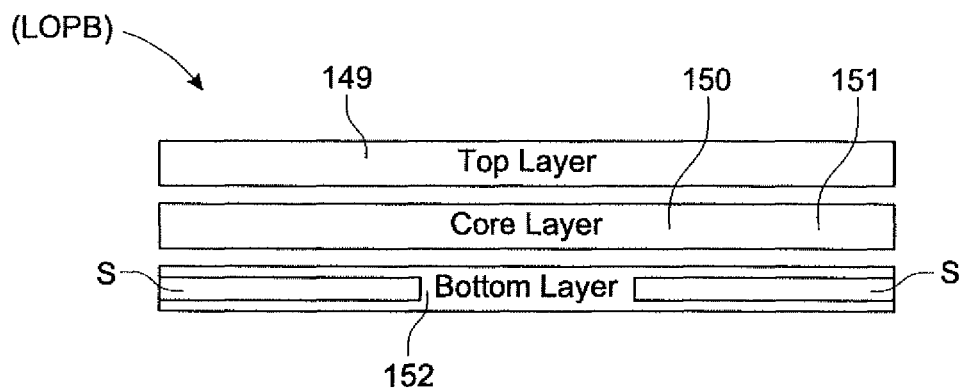

FIGS. 20A-20E present illustrations of exemplary devices, systems and methods for detecting, monitoring or measuring chemicals, analytes and other factors in food/beverage/drug or the environment of food/beverage/drug throughout the supply chain (SYS) as part of Phase (D) in the method (METH=A+B+C+D) disclosed in FIG. 1. FIG. 20A illustrates an exemplary fluid adsorbent pad with sensor (APF). FIG. 20B illustrates an exemplary gas absorbent/fluid absorbent pad with sensor for adjusting or controlling gas, vapor or other factors (APG). FIG. 20C illustrates exemplary layers of gas absorbent/fluid absorbent pad, where sensor is in core layer pf pad (LOPM). FIG. 20D illustrates exemplary layers of gas absorbent/fluid absorbent pad, where sensor is in top layer of pad (LOPT). FIG. 20E illustrates exemplary layers of gas absorbent/fluid absorbent pad, where sensor is in bottom layer (LOPB).

FIG. 13A illustrates an exemplary embodiment where sensors (S) can be deployed in or on a carried material in the form of a pad that adsorbs fluid (APF). The adsorbent pad (147) soaks up liquid that naturally ooze out of fish (105), poultry (133), meat (131) and other food/beverage/drug, preventing the liquids from pooling in the package. Preventing liquids from pooling is especially important because liquid from raw foods, particularly fish (105), poultry (133) and meat (131) can contain active bacteria that is dangerous to human health. By preventing liquids from pooling, the pads (147) also prevent bacteria from breeding and ultimately lowers the risk of foodborne illness. The pads are widely used with cellophane wrapped trays (132) to eliminate excess moisture. Their special pad linings can be made from cellulose fibers and sealed into a polyethylene wrapping. All pads (147) are to be USDA and FDA biocompatible.

The fluid adsorbent pads (147) can be made from one of two adsorptive materials: Silica gel (e.g. a purified sand) or cellulose (e.g. a purified plant fiber), which are then coated in a non-toxic plastic wrapping that's perforated, allowing the liquid to seep in and stay there. These materials can hold up to 40 grams of liquid. The sensors (S) can be embedded in the pad (147) or attached to a surface of the pad.

FIG. 13B present another exemplary embodiment where sensors (S) can be deployed in or on a carried material, in the form of a pad that can adsorbs fluid or moisture or absorbs gas or vapor or can do both (APG). The fluid adsorbent and gas absorbent pad (148) detects and controls factors in the environment of food/beverage/drug. Such factors can include humidity, moisture, chemical concentration, gas concentration vapor concentration among other undesirable factors. For example, the pad (148) can absorb moisture droplets, which prevents fungus from forming. The pad (148) can also absorb ethylene, which is released by food during the ripening and ageing process. Ethylene is the most potent agent of fruit and vegetable aging and its effective absorption has a proven and significant benefit for shelf-life. Another purpose of the pad (148) is to provide cushioning and avoid bruising or damage to the food.

The pad (148) has a perforated or ripped texture as a result of design features related to cushioning food and controlling concentration levels of chemicals, gases or vapors in food packages. The pad (148) can be made mostly from cellulose fibers and tissues and then coated with a non-toxic biodegradable wrap that is perforated, allowing moisture to seep in and stay there. The sensors (S) can be embedded in the pad (148) or attached to a surface of the pad (148).

FIG. 20C presents an exemplary structure or layers pads, where the sensor is placed in the core or second layer (LOPM). In the exemplary embodiment, the fluid adsorbent pad/gas absorbent pad (147/148) can consist of three layers. The top layer (149) can comprise of a waterproof polyethylene film. The second layer or core layer (150) can comprise of superabsorbent polymer also called a slush powder, which is classified as a hydrogel (151). The polymer hydrogel (151) can retain extremely large amounts of a liquid relative to its own mass. The bottom layer (152) can comprise of a perforated polyethylene film or non-woven fabrics.

The second layer or core layer (150) consisting, in one example, of the polymer hydrogel (151) is especially important because the superabsorbent polymer (151) collects aqueous solution through hydrogen bonding with water molecules. The total absorbency and swelling capacity are controlled by the type and degree of cross-linkers used to make the hydrogel. Low-density cross-linked hydrogels (151) generally have a higher absorbent capacity and swell to a larger degree. These types of superabsorbent polymers (151) also have a softer and stickier gel formation. High cross-link density polymer gels (151) exhibit lower absorbent capacity and swell, but the gel strength is firmer and can maintain particle shape even under modest pressure.

The superabsorbent properties of the hydrogel (151) make for an optimal sensing environment for monitor/detectors (20), particularly those disclosed in FIGS. 3A-3C as well as other types of sensors. The hydrogel itself can even function as a monitor/detector (20) in that hydrogels are hydrophilic and highly water swellable polymer networks capable of converting chemical energy into mechanical energy and integrated into micro systems such as those disclosed within. For example, the chemical energy of a hydrogel can transpire into mechanical energy, which is measured in various ways such as units of pressure, size, swelling, weight among others. It should be appreciated and assumed that the environment of the present disclosure is highly conducive for any type chemical sensor, including those not included in this disclosure. As such, a plurality of detectors or sensors (28) or monitor/detector (20) or a monitoring device (16) or a sensor (S) can be attached to or embedded in the hydrogel (151).

In one embodiment, the entire sensor (S) is attached or embedded in the core layer (150) of the layers adsorbent pads (LOPM) such that the monitor/detector (20) is in continuous contact with the superabsorbent polymers (151) ensuring continuous flow of liquid to the monitor/detector (20). This exemplary embodiment can include an active/passive flow induction (26) as part of the sensor (S). As previously stated, the induction device (26) helps ensure a continuous flow of liquid to the monitor/detector (20) and can be included as part of the sensor (S) only when necessary. The flow induction (26) can be in the form of a housing (HEC/MHEC) or envelope (138). The housing can be designed such that it encloses at least one element or component of the sensor (S) (e.g. active/passive power source (24), communication circuitry (22), connector assembly (CON), active/passive induction (26) and even portions or the monitor/detector (20)).

In another embodiment the entire monitoring device (16) is attached or embedded in the core layer (150) of the layers adsorbent pads (LOPM) such that the monitor/detector (20) is in continuous contact with the superabsorbent polymers (151) ensuring continuous flow of liquid to the monitor/detector (20). In another embodiment, only the monitor/detector (20) is attached or embedded in the core layer (150) of the layers adsorbent pads (LOPM) such that the monitor/detector (20) is in continuous contact with the superabsorbent polymers (151) ensuring continuous flow of liquid to the monitor/detector (20).

In another embodiment, only the plurality of detectors or sensors (28) are attached or embedded in the core layer (150) of the layers adsorbent pads (LOPM) such that the monitor/detector (20) is in continuous contact with the superabsorbent polymers (151) ensuring continuous flow of liquid to the monitor/detector (20).

In another embodiment, no components of the monitoring system (16) are attached or embedded in the core layer (150) of the layers adsorbent pads (LOPM), however fluid is sampled from the superabsorbent polymers (151) and transmitted to the monitor/detector (20) for detection, measuring and monitoring. Another embodiment relates to FIG. 19 that illustrates an exemplary sensor strip (STP) that comprises of printed elements or components. The sensor strip (STP) can be attached or embedded in the pads (147/148), including the core layer (150) or top layer (149) or bottom layer (152). Similar to previously disclosed embodiments, the monitor/detector (20) could be in continuous contact with the superabsorbent polymers (151) ensuring continuous flow of liquid to the monitor/detector (20).

FIG. 20D presents an exemplary structure or layers pads used for packages or containers (LOPT). In the exemplary embodiment, the sensor (S) is placed in the top layer (149) of the fluid adsorbent pad/gas absorbent pad (147/148).

FIG. 20E presents an exemplary structure or layers pads used for packages or containers (LOPB). In the exemplary embodiment, the sensor (S) is placed in the bottom layer (152) of the fluid adsorbent pad/gas absorbent pad (147/148).

Figure 21:
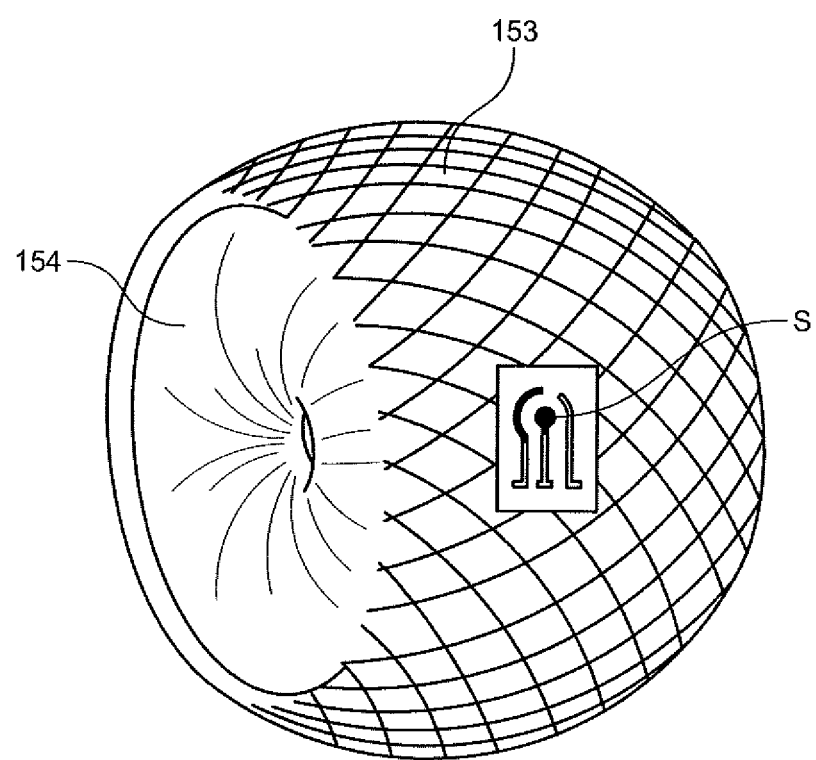
FIG. 21 illustrates an exemplary sensor deployment on a carried material in the form of a covering or sticker or label and in accordance with the present disclosure.

FIG. 21 illustrates exemplary devices, systems and methods for detecting, monitoring or measuring chemicals, analytes and other factors in food/beverage/drug or the environment of food/beverage/drug throughout the supply chain (SYS) as part of Phase (D) in the method (METH=A+B+C+D) disclosed in FIG. 1. FIG. 21 illustrates an exemplary sensor (S) printed or mounted on a carrier material (126) such as a strip or covering or label or sticker. The exemplary embodiment presents a sensor (S) on a protective covering (153), but it should be appreciated that applications can include any material placed on or adhered directly to food/beverage/drug such as stickers or labels or bands or clips or caps or seals etc. The covering (153) is adhered to an apple (154).

The invention claimed is:

1. A system for detecting or monitoring or measuring chemicals or concentration levels of chemicals in a product intended for consumption or an environment of a product intended for consumption, the system comprising:
a sensor including a monitor/detector component, communication circuitry and a power source operatively coupled to the detector component and the communication circuitry for supplying power thereto, and wherein the communication circuitry is configured to transmit data to an associated receiver;
wherein the system further determines at least one of a location or operating status of the sensor, the communication circuitry configured to transmit the location and operating status to the associated receiver;
a protective housing enclosing one or more of the sensor, power source or communication circuitry wherein the protective housing is a biocompatible housing resistant to factors in an environment; and
wherein the biocompatible factor resistant housing comprises a seal and coating that resist factors in the environment that affect operability of the sensor;
wherein at least one of the detector component, communication circuitry, power source or housing is part of a removable/replaceable module; and
wherein the sensor includes a flexible connector assembly for operatively coupling the monitor/detector component, with the communication circuitry and power source;
wherein the flexible connector assembly is biocompatible and suitable for use in products intended for consumption; and
wherein the monitor/detector is programmed with algorithms downloaded from a central source; and
wherein the monitor/detector is an electrochemical sensor; and
wherein the electrochemical sensor is in contact with the product.

2. The system of claim 1, wherein the monitor/detector component includes a plurality of detectors for monitoring at least one of location, speed, temperature, humidity, moisture, flow, pH, nutrients, light, radiation, pressure, vibration, authenticity and shock.

3. The system of claim 1, wherein an environment of the product intended for consumption includes an environment internal to the product intended for consumption or an environment external to the product intended for consumption.

4. The system of claim 3, wherein the environment external to the product intended for consumption includes at least one of enclosed areas, semi-enclosed areas, open-air areas or surface areas that comes into contact with the product intended for consumption or come into contact with the environment of the product intended for consumption.

5. The system of claim 4, wherein the environment external to the product intended for consumption includes at least one of a absorbent material, box, bag, band, bin, bowl, bottle, bucket, case, can, carton, cover, chiller, crate, container, countertop, conveyor, cup, drawer, dumpster, display, freezer, jar, label, mixer, package, pad, paper, plastic, plate, processor, pan, pallet cover, pallet wrap, pouch, rack, refrigerator, seal, strip, shaker, shelf, stand, strainer, stirrer, slicer, separator, sticker, tray, tape, wrapping or other material or equipment or component or infrastructure used to harness, hold, process, package, display, store, transport or control the product intended for consumption.

6. The system of claim 4, wherein one or more component or element of the system is fixed to, adhered to, embedded in or printed on a surface or lining or layer or cover or portion of the environment external to the product intended for consumption.

7. The system of claim 1, wherein at least one component or element of the system is mobile within an environment.

8. The system of claim 1, wherein the detector is entirely embedded in the product intended for consumption or partially embedded in the product intended for consumption or attached to a surface of the product intended for consumption or remote from the product intended for consumption, and wherein the flexible connector includes a silver-loaded epoxy.

9. The system of claim 1, wherein the system includes a flow induction device including at least one of concentrators, heating or cooling components, fans, flow paths, pumps, mixers, valves, conduits, channels, or housings.

10. The system of claim 1, wherein the power source includes an antenna configured to receive energy wirelessly and supply the received energy to at least one of the detector components or the communication circuitry.

11. The system of claim 1, wherein at least one of the monitor/detector component, communication circuitry or power source is a printed element or printed component.

12. A system for detecting or monitoring or measuring chemicals or concentration levels of chemicals in a product intended for consumption or an environment of a product intended for consumption, the system comprising:
a container or box used to transport, store and sell consumables;
a monitor/detector component for measuring chemicals or concentration levels of chemicals, communication circuitry and a power source operatively coupled to the detector component and the communication circuitry for supplying power thereto, and wherein the communication circuitry is configured to transmit data to an associated receiver;
wherein the monitor/detector component includes a plurality of detectors for monitoring at least one of location, speed, temperature, humidity, moisture, flow, pH, nutrients, light, radiation, pressure, vibration and shock;
wherein the monitoring system further includes a protective housing enclosing one or more of the monitor/detector component, power source or communication circuitry;
wherein the protective housing is a biocompatible housing resistant to factors in an environment;

wherein the biocompatible factor resistant housing comprises a seal and coating that resist contaminants in the environment and factors that affect operability of the sensor;

wherein the monitoring system further comprises a flexible connector assembly for operatively coupling the monitor/detector component with the communication circuitry and power source;

wherein the flexible connector assembly is biocompatible and suitable for use in products intended for consumption;

wherein the monitor/detector is programmed with algorithms downloaded from a central source; and wherein the monitor/detector is an electrochemical sensor;

wherein the electrochemical sensor is in contact with the product; and wherein at least one of the monitor/detector component, communication circuitry, power source, connector assembly or housing is part of removable/replaceable modules.

13. A method of monitoring a product intended for consumption or an area that comes into contact with a product intended for consumption or an environment of a product intended for consumption for the presence or absence of one or more chemicals or concentration level of one or more chemicals, the method comprising:

providing a plurality of sensors, each sensor including a detector component for measuring chemicals or concentration level of chemicals operative to generate data in response to the presence or absence of one or more chemicals, communication circuitry and a power source operatively coupled to the detector component and the communication circuitry for supplying power thereto, a protective housing enclosing one or more of the detector component, power source or communication circuitry, and a flexible connector assembly for operatively coupling the monitor/detector component with the communication circuitry and power source, the communication circuitry configured to transmit data generated by the detector component corresponding to the presence or absence of one or more chemicals to an associated receiver;

wherein the flexible connector assembly is biocompatible and suitable for use in products intended for consumption;

wherein the monitor/detector is programmed with algorithms downloaded from a central source; and wherein the plurality of sensors are electrochemical sensors;

wherein the electrochemical sensors are in contact with the product; and associating each sensor with a location or a location within an area to be monitored;

monitoring each location or location within an area with its associated sensor over a period of time; tracking that location or location within an area over a period of time and transmitting data generated by each sensor to a receiver.

14. The method of claim 13, further comprising a plurality of sensors for measuring or monitoring or tracking at least one of location, speed, temperature, humidity, moisture, flow, pH, nutrients, light, radiation, pressure, vibration or shock over a period of time.

15. The method of claim 13, wherein the power source includes an antenna configured to receive energy wirelessly and supply the received energy to at least one of the detector components or the communication circuitry.

16. The method of claim 13, further comprising approximating conditions prompting the ingress of the one or more chemicals based at least in part on data generated by one or more sensors the conditions including at least one of day, time, location, speed, temperature, humidity, moisture, flow, pH, nutrients, light, radiation, pressure, vibration, or shock.

17. The method of claim 13, wherein each sensor is configured to sense a concentration of the one or more chemicals and generate data indicative of the sensed concentration.

18. The method of claim 17, wherein each sensor is configured to periodically report a sensed concentration over a period of time to an associated receiver.

19. The method of claim 17, further comprising comparing the sensed concentration to a threshold concentration and generating an alert if the sensed concentration exceeds the threshold concentration.

20. A system for detecting or monitoring or measuring chemicals or concentration levels of chemicals in a product intended for consumption or an environment of a product intended for consumption, the system comprising:

a sensor including a monitor/detector component, communication circuitry and a power source operatively coupled to the detector component and the communication circuitry for supplying power thereto, and wherein the communication circuitry is configured to transmit data to an associated receiver;

wherein the system further determines at least one of a location or operating status of the sensor, the communication circuitry configured to transmit the location and operating status to the associated receiver; and wherein the power source includes an antenna configured to receive energy wirelessly and supply the received energy to at least one of the detector components or the communication circuitry; and wherein the sensor is attached to packaging of product intended for consumption;

a protective housing enclosing one or more of the sensor, power source or communication circuitry wherein the protective housing is a biocompatible housing resistant to factors in an environment; and wherein the biocompatible factor resistant housing comprises a seal and coating that resist factors in the environment that affect operability of the sensor; and wherein the at least one the detector component, communication circuitry, power source or housing is part of a removeable/replaceable module;

wherein the sensor includes a flexible connector assembly is biocompatible and is for operatively coupling the monitor/detector component, with the communication circuitry of power source; and wherein the monitor/detector is programmed with algorithms downloaded from a central source;

wherein the monitor/detector is an electrochemical sensor; and wherein the sensor is attached to packaging of a product intended for consumption.

* * * * *